United States Patent
Aronov et al.

(10) Patent No.: US 8,268,999 B2
(45) Date of Patent: Sep. 18, 2012

(54) TRI-CYCLIC PYRAZOLOPYRIDINE KINASE INHIBITORS

(75) Inventors: Alex Aronov, Newton, MA (US); Jon H. Come, Cambridge, MA (US); Kevin Michael Cottrell, Cambridge, MA (US); Arnaud Le Tiran, Croissy sur Seine (FR); Valerie Marone, Waltham, MA (US); Gabriel Martinez Botella, Wayland, MA (US); David Messersmith, Somerville, MA (US); Emilie Porter Huck, Sudbury, MA (US); Ronald Lee Grey, Jr., Mansfield, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 13/216,606

(22) Filed: Aug. 24, 2011

(65) Prior Publication Data

US 2012/0053187 A1    Mar. 1, 2012

Related U.S. Application Data

(63) Continuation of application No. PCT/US2010/025343, filed on Feb. 25, 2010.

(60) Provisional application No. 61/156,139, filed on Feb. 27, 2009.

(51) Int. Cl.
*C07D 401/10* (2006.01)
*A61K 31/497* (2006.01)

(52) U.S. Cl. .................................. 544/238; 514/255.05

(58) Field of Classification Search .................. 544/238; 514/255.05

See application file for complete search history.

(56) References Cited

U.S. PATENT DOCUMENTS

2005/0203146 A1*   9/2005   Herpin et al. ................. 514/338

FOREIGN PATENT DOCUMENTS

| WO | 2005070920 A1 | 8/2005 |
| WO | 2007095588 A1 | 8/2007 |
| WO | 2009017822 A2 | 2/2009 |
| WO | 2009129211 A1 | 10/2009 |
| WO | 2009133127 A1 | 11/2009 |

OTHER PUBLICATIONS

PCT/US2010/025343 International Search Report dated Jul. 7, 2010.

* cited by examiner

*Primary Examiner* — Robert Havlin
(74) *Attorney, Agent, or Firm* — Daniel A. Pearson

(57) ABSTRACT

The present invention relates to compounds useful as inhibitors of PI3K, particularly of PI3Kγ. The invention also provides pharmaceutically acceptable compositions comprising said compounds and methods of using the compositions in the treatment of various disease, conditions, or disorders.

11 Claims, No Drawings

TRI-CYCLIC PYRAZOLOPYRIDINE KINASE INHIBITORS

CROSS REFERENCE TO RELATED APPLICATIONS

This application is a continuation of International Patent Application No. PCT/US2010/025343, filed Feb. 25, 2010, which claims benefit, under 35 U.S.C. §119, to U.S. Provisional Application No. 61/156,139 filed Feb. 27, 2009, the entire disclosures of which are incorporated herein by reference.

TECHNICAL FIELD OF THE INVENTION

The present invention relates to compounds useful as inhibitors of phosphatidylinositol 3-kinase (PI3K). The invention also provides pharmaceutically acceptable compositions comprising the compounds of the invention and methods of using the compositions in the treatment of various disorders.

BACKGROUND OF THE INVENTION

PI3Ks are a family of lipid kinases that catalyze the phosphorylation of the membrane lipid phosphatidylinositol (PI) on the 3'-OH of the inositol ring to produce PI 3-phosphate [PI(3)P, PIP], PI 3,4-bisphosphate [PI(3,4)$P_2$, PIP2] and PI 3,4,5-trisphosphate [PI(3,4,5)$P_3$, PIP3]. PI(3,4)$P_2$ and PI(3, 4,5)$P_3$ act as recruitment sites for various intracellular signaling proteins, which in turn form signaling complexes to relay extracellular signals to the cytoplasmic face of the plasma membrane.

Eight mammalian PI3Ks have been identified so far, including four class I PI3Ks. Class Ia includes PI3Kα, PI3Kβ and PI3Kδ. All of the class Ia enzymes are heterodimeric complexes comprising a catalytic subunit (p110α, p110β or p110δ) associated with an SH2 domain-containing p85 adapter subunit. Class Ia PI3Ks are activated through tyrosine kinase signaling and are involved in cell proliferation and survival. PI3Kα and PI3Kβ have also been implicated in tumorigenesis in a variety of human cancers. Thus, pharmacological inhibitors of PI3Kα and PI3Kβ are useful for treating various types of cancer.

PI3Kγ, the only member of the Class Ib PI3Ks, consists of a catalytic subunit p110γ, which is associated with a p101 regulatory subunit. PI3Kγ is regulated by G protein-coupled receptors (GPCRs) via association with (3γ subunits of heterotrimeric G proteins. PI3Kγ is expressed primarily in hematopoietic cells and cardiomyocytes and is involved in inflammation and mast cell function. Thus, pharmacological inhibitors of PI3Kγ are useful for treating a variety of inflammatory diseases, allergies and cardiovascular diseases.

Although a number of PI3K inhibitors have been developed, there is a need for additional compounds to inhibit PI3Ks for treating various disorders and diseases, such as autoimmune diseases, inflammatory diseases, cancer, allergic diseases, asthma, and respiratory diseases. Accordingly, it would be desirable to develop additional compounds that are useful as inhibitors of PI3K.

SUMMARY OF THE INVENTION

It has been found that compounds of this invention, and pharmaceutically acceptable compositions thereof, are effective as inhibitors of PI3K, particularly PI3Kγ. Accordingly, the invention features compounds having the general formula:

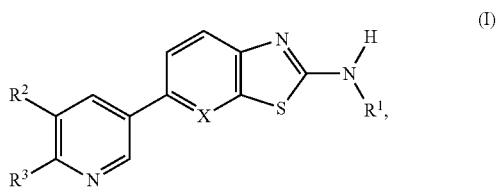

(I)

or a pharmaceutically acceptable salt thereof, where each of $R^1$, $R^2$, $R^3$, and X is as defined herein.

The invention also provides pharmaceutical compositions that include a compound of formula I and a pharmaceutically acceptable carrier, adjuvant, or vehicle. These compounds and pharmaceutical compositions are useful for treating or lessening the severity of a variety of disorders, including autoimmune diseases and inflammatory diseases of the CNS.

The compounds and compositions provided by this invention are also useful for the study of PI3K in biological and pathological phenomena; the study of intracellular signal transduction pathways mediated by such kinases; and the comparative evaluation of new kinase inhibitors.

DETAILED DESCRIPTION OF THE INVENTION

Definitions and General Terminology

As used herein, the following definitions shall apply unless otherwise indicated. For purposes of this invention, the chemical elements are identified in accordance with the Periodic Table of the Elements, CAS version, and the Handbook of Chemistry and Physics, 75th Ed. 1994. Additionally, general principles of organic chemistry are described in "Organic Chemistry," Thomas Sorrell, University Science Books, Sausalito: 1999, and "March's Advanced Organic Chemistry," 5th Ed., Smith, M. B. and March, J., eds. John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted," whether preceded by the term "optionally" or not, refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position.

As described herein, when the term "optionally substituted" precedes a list, said term refers to all of the subsequent substitutable groups in that list. For example, if X is halogen; optionally substituted $C_{1-3}$ alkyl or phenyl; X may be either optionally substituted alkyl or optionally substituted phenyl. Likewise, if the term "optionally substituted" follows a list, said term also refers to all of the substitutable groups in the prior list unless otherwise indicated. For example: if X is halogen, $C_{1-3}$ alkyl, or phenyl, wherein X is optionally substituted by $J^X$, then both $C_{1-3}$ alkyl and phenyl may be optionally substituted by J^X. As is apparent to one having ordinary skill in the art, groups such as H, halogen, $NO_2$, CN, $NH_2$, OH, or $OCF_3$ would not be included because they are not substitutable groups. If a substituent radical or structure is not identified or defined as "optionally substituted," the substituent radical or structure is unsubstituted.

Combinations of substituents envisioned by this invention are preferably those that result in the formation of stable or chemically feasible compounds. The term "stable," as used herein, refers to compounds that are not substantially altered when subjected to conditions to allow for their production, detection, and, preferably, their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group," as used herein, means a straight-chain (i.e., unbranched) or branched, substituted or unsubstituted hydrocarbon chain that is completely saturated or that contains one or more units of unsaturation. Unless otherwise specified, aliphatic groups contain 1-20 carbon atoms. In some embodiments, aliphatic groups contain 1-10 carbon atoms. In other embodiments, aliphatic groups contain 1-8 carbon atoms. In still other embodiments, aliphatic groups contain 1-6 carbon atoms, and in yet other embodiments, aliphatic groups contain 1-4 carbon atoms. Suitable aliphatic groups include, but are not limited to, linear or branched, substituted or unsubstituted alkyl, alkenyl, or alkynyl groups. Further examples of aliphatic groups include methyl, ethyl, propyl, butyl, isopropyl, isobutyl, vinyl, and sec-butyl. The terms "alkyl" and the prefix "alk-," as used herein, are inclusive of both straight chain and branched saturated carbon chain. The term "alkylene," as used herein, represents a saturated divalent straight or branched chain hydrocarbon group and is exemplified by methylene, ethylene, isopropylene and the like. The term "alkylidene," as used herein, represents a divalent straight chain alkyl linking group. The term "alkenyl," as used herein, represents monovalent straight or branched chain hydrocarbon group containing one or more carbon-carbon double bonds. The term "alkynyl," as used herein, represents a monovalent straight or branched chain hydrocarbon group containing one or more carbon-carbon triple bonds.

The term "cycloaliphatic" (or "carbocycle") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule, and wherein any individual ring in said bicyclic ring system has 3-7 members. Suitable cycloaliphatic groups include, but are not limited to, cycloalkyl, cycloalkenyl, and cycloalkynyl. Further examples of aliphatic groups include cyclopentyl, cyclopentenyl, cyclohexyl, cyclohexenyl, cycloheptyl, and cycloheptenyl.

The term "heterocycle," "heterocyclyl," "heterocycloaliphatic," or "heterocyclic" as used herein refers to a monocyclic, bicyclic, or tricyclic ring system in which at least one ring in the system contains one or more heteroatoms, which is the same or different, and that is completely saturated or that contains one or more units of unsaturation, but which is not aromatic, and that has a single point of attachment to the rest of the molecule. In some embodiments, the "heterocycle," "heterocyclyl," "heterocycloaliphatic," or "heterocyclic" group has three to fourteen ring members in which one or more ring members is a heteroatom independently selected from oxygen, sulfur, nitrogen, or phosphorus, and each ring in the system contains 3 to 8 ring members.

Examples of heterocyclic rings include, but are not limited to, the following monocycles: 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl; and the following bicycles: 3-1H-benzimidazol-2-one, 3-(1-alkyl)-benzimidazol-2-one, indolinyl, tetrahydroquinolinyl, tetrahydroisoquinolinyl, benzothiolane, benzodithiane, and 1,3-dihydroimidazol-2-one.

The term "heteroatom" means one or more of oxygen, sulfur, nitrogen, phosphorus, or silicon, including any oxidized form of nitrogen, sulfur, or phosphorus; the quaternized form of any basic nitrogen; or a substitutable nitrogen of a heterocyclic ring, for example N (as in 3,4-dihydro-2H-pyrrolyl), NH (as in pyrrolidinyl) or $NR^+$ (as in N-substituted pyrrolidinyl).

The term "unsaturated," as used herein, means that a moiety has one or more units of unsaturation.

The term "alkoxy," or "thioalkyl," as used herein, refers to an alkyl group, as previously defined, attached to the principal carbon chain through an oxygen ("alkoxy") or sulfur ("thioalkyl") atom.

The terms "haloalkyl," "haloalkenyl," and "haloalkoxy" mean alkyl, alkenyl, or alkoxy, as the case may be, substituted with one or more halogen atoms. The term "halogen" means F, Cl, Br, or I.

The term "aryl" used alone or as part of a larger moiety as in "aralkyl," "aralkoxy," or "aryloxyalkyl," refers to a monocyclic, bicyclic, or tricyclic carbocyclic ring system having a total of six to fourteen ring members, wherein said ring system has a single point of attachment to the rest of the molecule, at least one ring in the system is aromatic and wherein each ring in the system contains 3 to 7 ring members. The term "aryl" may be used interchangeably with the term "aryl ring." Examples of aryl rings include phenyl, naphthyl, and anthracene.

The term "heteroaryl," used alone or as part of a larger moiety as in "heteroaralkyl," or "heteroarylalkoxy," refers to a monocyclic, bicyclic, and tricyclic ring system having a total of five to fourteen ring members, wherein said ring system has a single point of attachment to the rest of the molecule, at least one ring in the system is aromatic, at least one ring in the system contains one or more heteroatoms independently selected from nitrogen, oxygen, sulfur or phosphorus, and wherein each ring in the system contains 3 to 7 ring members. The term "heteroaryl" may be used interchangeably with the term "heteroaryl ring" or the term "heteroaromatic."

Further examples of heteroaryl rings include the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles: benzimidazolyl, benzofuryl, benzothiophenyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

In some embodiments, an aryl (including aralkyl, aralkoxy, aryloxyalkyl, and the like) or heteroaryl (including heteroaralkyl, heteroarylalkoxy, and the like) group may contain one or more substituents. Suitable substituents on the unsaturated carbon atom of an aryl or heteroaryl group include: halogen; —R°; —OR°; —SR°; 1,2-methylenedioxy; 1,2-ethylenedioxy; phenyl (Ph), optionally substituted with R°; —O(Ph), optionally substituted with R°; —(CH$_2$)$_{1-2}$(Ph), optionally substituted with R°; —CH=CH(Ph), optionally substituted with R°; —NO$_2$; —CN; —N(R°)$_2$; —NR°C(O)R°; —NR°C(S)R°; —NR°C(O)N(R°)$_2$; —NR°C(S)N(R°)$_2$; —NR°C(O)OR°; —NR°NR°C(O)R°; —NR°NR°C(O)N(R°)$_2$; —NR°NR°C(O)OR°; —C(O)C(O)R°; —C(O)CH$_2$C(O)R°; —C(O)OR°; —C(O)R°; —C(S)R°; —C(O)N(R°)$_2$; —C(S)N(R°)$_2$; —B(OR°$_2$;) —OC(O)N(R°)$_2$; —OC(O)R°; —C(O)N(OR°)R°; —C(NOR°)R°; —S(O)$_2$R°; —S(O)$_3$R°; —S(O)$_2$N(R°)$_2$; —S(O)R°; —NR°S(O)$_2$N(R°)$_2$; —NR°S(O)$_2$R°; —N(OR°)R°; —C(=NH)—N(R°)$_2$; —(CH$_2$)$_{0-2}$NHC(O)R°; -L-R°; -L-N(R°)$_2$; -L-SR°; -L-OR°; -L-(C$_{3-10}$ cycloaliphatic), -L-(C$_{6-10}$ aryl), -L-(5-10 membered heteroaryl), -L-(5-10 membered heterocyclyl), oxo, C$_{1-4}$ haloalkoxy, C$_{1-4}$ haloalkyl, -L-NO$_2$, -L-CN, -L-OH, -L-CF$_3$; or two substituents, on the same carbon or on different carbons, together with the carbon or intervening carbons to which they are bound, form a 5-7 membered saturated, unsaturated, or partially saturated ring, wherein L is a C$_{1-6}$ alkylene group in which up to three methylene units are replaced by —NH—, —NR°—, —O—, —S—, —C(O)O—, —OC(O)—, —C(O)CO—, —C(O)—, —C(O)NH—, —C(O)NR°—, —C(=N—CN), —NHCO—, —NR°CO—, —NHC(O)O—, —NR°C(O)O—, —S(O)$_2$NH—, —S(O)$_2$NR°—, —NHS(O)$_2$—, —NR°S(O)$_2$—, —NHC(O)NH—, —NR°C(O)NH—, —NHC(O)NR°—, —NR°C(O)NR°, —OC(O)NH—, —OC(O)NR°—, —NHS(O)$_2$NH—, —NR°S(O)$_2$NH—, —NHS(O)$_2$NR°—, —NR°S(O)$_2$NR°—, —S(O)—, or —S(O)$_2$—, and wherein each occurrence of R° is independently selected from hydrogen, optionally substituted C$_{1-6}$ aliphatic, an unsubstituted 5 to 6 membered heteroaryl or heterocyclic ring, phenyl, or —CH$_2$(Ph), or, two independent occurrences of R°, on the same substituent or different substituents, taken together with the atom(s) to which each R° group is bound, form a 5-8-membered heterocyclyl, aryl, or heteroaryl ring or a 3- to 8-membered cycloalkyl ring, wherein said heteroaryl or heterocyclyl ring has 1 to 3 heteroatoms independently selected from nitrogen, oxygen, or sulfur. Non-limiting optional substituents on the aliphatic group of R° include —NH$_2$, —NH(C$_{1-4}$ aliphatic), —N(C$_{1-4}$ aliphatic)$_2$, halogen, C$_{1-4}$ aliphatic, —OH, —O(C$_{1-4}$ aliphatic), —NO$_2$, —CN, —C(O)OH, —C(O)O(C$_{1-4}$ aliphatic), —O(haloC$_{1-4}$ aliphatic), or haloC$_{1-4}$ aliphatic, wherein each of the foregoing C$_{1-4}$ aliphatic groups of R° is unsubstituted.

In some embodiments, an aliphatic or heteroaliphatic group, or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHC(O)O(alkyl), =NNHS(O)$_2$(alkyl), or =NR*, where each R* is independently selected from hydrogen or an optionally substituted C$_{1-8}$ aliphatic. Optional substituents on the aliphatic group of R* are selected from —NH$_2$, —NH(C$_{1-4}$ aliphatic), —N(C$_{1-4}$ aliphatic)$_2$, halogen, C$_{1-4}$ aliphatic, —OH, —O(C$_{1-4}$ aliphatic), —NO$_2$, —CN, —C(O)OH, —C(O)O(C$_{1-4}$ aliphatic), —C(O)NH$_2$, —C(O)NH(C$_{1-4}$ aliphatic), —C(O)N(C$_{1-4}$ aliphatic)$_2$, —O(halo-C$_{1-4}$ aliphatic), and halo(C$_{1-4}$ aliphatic), where each of the foregoing C$_{1-4}$ aliphatic groups of R* is unsubstituted; or two R* on the same nitrogen are taken together with the nitrogen to form a 5-8 membered heterocyclyl or heteroaryl ring having 1-3 heteroatoms independently selected from nitrogen, oxygen, and sulfur.

In some embodiments, optional substituents on the nitrogen of a non-aromatic heterocyclic ring include —R$^+$, —N(R$^+$)$_2$, —C(O)R$^+$, —C(O)OR$^+$, —C(O)C(O)R$^+$, —C(O)CH$_2$C(O)R$^+$, —S(O)$_2$R$^+$, —S(O)$_2$N(R$^+$)$_2$, —C(=S)N(R$^+$)$_2$, —C(=NH)—N(R$^+$)$_2$, or —NR$^+$S(O)$_2$R$^+$; wherein R$^+$ is hydrogen, an optionally substituted C$_{1-6}$ aliphatic, optionally substituted phenyl, optionally substituted —O(Ph), optionally substituted —CH$_2$(Ph), optionally substituted —(CH$_2$)$_{1-2}$(Ph); optionally substituted —CH=CH(Ph); or an unsubstituted 5-6 membered heteroaryl or heterocyclic ring having one to four heteroatoms independently selected from oxygen, nitrogen, or sulfur, or, two independent occurrences of R$^+$, on the same substituent or different substituents, taken together with the atom(s) to which each R$^+$ group is bound, form a 5-8-membered heterocyclyl, aryl, or heteroaryl ring or a 3-8 membered cycloalkyl ring, wherein said heteroaryl or heterocyclyl ring has 1-3 heteroatoms independently selected from nitrogen, oxygen, or sulfur. Optional substituents on the aliphatic group or the phenyl ring of R$^+$ are selected from —NH$_2$, —NH(C$_{1-4}$ aliphatic), —N(C$_{1-4}$ aliphatic)$_2$, halogen, C$_{1-4}$ aliphatic, —OH, —O(C$_{1-4}$ aliphatic), —NO$_2$, —CN, —C(O)OH, —C(O)O(C$_{1-4}$ aliphatic), —O(halo(C$_{1-4}$ aliphatic)), or halo(C$_{1-4}$ aliphatic), wherein each of the foregoing C$_{1-4}$ aliphatic groups of R$^+$ is unsubstituted.

As detailed above, in some embodiments, two independent occurrences of R° (or R$^+$, or any other variable similarly defined herein), may be taken together with the atom(s) to which each variable is bound to form a 5-8-membered heterocyclyl, aryl, or heteroaryl ring or a 3-8-membered cycloalkyl ring. Exemplary rings that are formed when two independent occurrences of R° (or R$^+$, or any other variable similarly defined herein) are taken together with the atom(s) to which each variable is bound include, but are not limited to the following: a) two independent occurrences of R° (or R$^+$, or any other variable similarly defined herein) that are bound to the same atom and are taken together with that atom to form a ring, for example, N(R°)$_2$, where both occurrences of R° are taken together with the nitrogen atom to form a piperidin-1-yl, piperazin-1-yl, or morpholin-4-yl group; and b) two independent occurrences of R° (or R$^+$, or any other variable similarly defined herein) that are bound to different atoms and are taken together with both of those atoms to form a ring, for example where a phenyl group is substituted with two occurrences of OR°

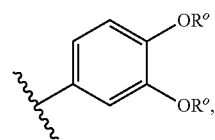

these two occurrences of R° are taken together with the oxygen atoms to which they are bound to form a fused 6-membered oxygen containing ring:

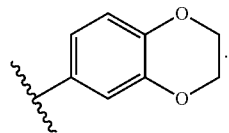

It will be appreciated that a variety of other rings can be formed when two independent occurrences of R° (or R⁺, or any other variable similarly defined herein) are taken together with the atom(s) to which each variable is bound and that the examples detailed above are not intended to be limiting.

In some embodiments, a methylene unit of the alkyl or aliphatic chain is optionally replaced with another atom or group. Examples of such atoms or groups would include, but are not limited to, —NR°—, —O—, —S—, —C(O)O—, —OC(O)—, —C(O)CO—, —C(O)—, —C(O)NR°—, —C(=N—CN), —NR°CO—, —NR°C(O)O—, —S(O)₂NR°—, —NR°S(O)₂—, —NR°C(O)NR°—, —OC(O)NR°—, —NR°S(O)₂NR°—, —S(O)—, or —S(O)₂—, wherein R° is defined herein. Unless otherwise specified, the optional replacements form a chemically stable compound. Optional atom or group replacements can occur both within the chain and at either end of the chain; i.e. both at the point of attachment and/or also at the terminal end. Two optional replacements can also be adjacent to each other within a chain so long as it results in a chemically stable compound. Unless otherwise specified, if the replacement occurs at the terminal end, the replacement atom is bound to an H on the terminal end. For example, if one methylene unit of —CH₂CH₂CH₃ was optionally replaced with —O—, the resulting compound could be —OCH₂CH₃, —CH₂OCH₃, or —CH₂CH₂OH.

As described herein, a bond drawn from a substituent to the center of one ring within a multiple-ring system (as shown below) represents substitution of the substituent at any substitutable position in any of the rings within the multiple ring system. For example, Structure a represents possible substitution in any of the positions shown in Structure b.

Structure a

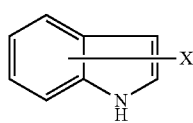

Structure b

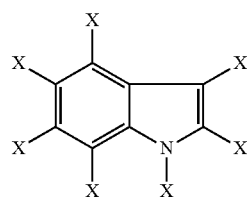

This also applies to multiple ring systems fused to optional ring systems (which would be represented by dotted lines). For example, in Structure c, X is an optional substituent both for ring A and ring B.

Structure c

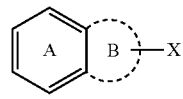

If, however, two rings in a multiple ring system each have different substituents drawn from the center of each ring, then, unless otherwise specified, each substituent only represents substitution on the ring to which it is attached. For example, in Structure d, Y is an optionally substituent for ring A only, and X is an optional substituent for ring B only.

Structure d

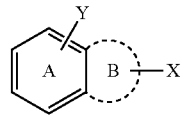

The term "protecting group," as used herein, represent those groups intended to protect a functional group, such as, for example, an alcohol, amine, carboxyl, carbonyl, etc., against undesirable reactions during synthetic procedures. Commonly used protecting groups are disclosed in Greene and Wuts, *Protective Groups In Organic Synthesis*, 3rd Edition (John Wiley & Sons, New York, 1999), which is incorporated herein by reference. Examples of nitrogen protecting groups include acyl, aroyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl and chiral auxiliaries such as protected or unprotected D, L or D, L-amino acids such as alanine, leucine, phenylalanine and the like; sulfonyl groups such as benzenesulfonyl, p-toluenesulfonyl and the like; carbamate groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl and the like, arylalkyl groups such as benzyl, triphenylmethyl, benzyloxymethyl and the like and silyl groups such as trimethylsilyl and the like. Preferred N-protecting groups are formyl, acetyl, benzoyl, pivaloyl, t-butylacetyl, alanyl, phenylsulfonyl, benzyl, t-butyloxycarbonyl (Boc) and benzyloxycarbonyl (Cbz).

The term "prodrug," as used herein, represents a compound that is transformed in vivo into a compound of formula I or a compound listed in Table 1. Such a transformation can be affected, for example, by hydrolysis in blood or enzymatic transformation of the prodrug form to the parent form in blood or tissue. Prodrugs of the compounds of the invention may be, for example, esters. Esters that may be utilized as prodrugs in the present invention are phenyl esters, aliphatic ($C_1$-$C_{24}$) esters, acyloxymethyl esters, carbonates, carbamates, and amino acid esters. For example, a compound of the invention that contains an OH group may be acylated at this position in its prodrug form. Other prodrug forms include phosphates, such as, for example those phosphates resulting from the phosphonation of an OH group on the parent compound. A thorough discussion of prodrugs is provided in T. Higuchi and V. Stella, *Pro-drugs as Novel Delivery Systems*, Vol. 14 of the A.C.S. Symposium Series, Edward B. Roche, ed., *Bioreversible Carriers in Drug Design*, American Pharmaceutical Association and Pergamon Press, 1987, and Judkins et al., *Synthetic Communications* 26(23):4351-4367, 1996, each of which is incorporated herein by reference.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools, probes in biological assays, or as PI3K inhibitors with improved therapeutic profile.

Description of Compounds of the Invention

In one aspect, the present invention features compounds having the formula:

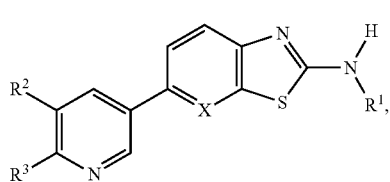

(I)

or a pharmaceutically acceptable salt thereof, wherein:
X is N or CH;
$R^1$ is selected from a phenyl ring, a 5-membered heteroaryl ring, a 6-membered heteroaryl ring, or a 9- or 10-membered fused bicyclic heteroaryl or heterocyclic ring system wherein each of said rings or ring systems is optionally substituted with 1, 2, or 3 independent occurrences of $R^{1a}$ and each of said heteroaryl or heterocyclic rings has 1, 2, or 3 heteroatoms selected from nitrogen, oxygen, or sulfur;
$R^{1a}$ is chloro, fluoro, $C_{1-6}$ aliphatic, $C_{3-6}$ cycloaliphatic, —C(O)$R^{1b}$, —C(O)N($R^{1b}$)$_2$, —C(O)O($R^{1b}$), —S(O)$R^{1b}$, —S(O)$_2$N($R^{1b}$)$_2$, —N($R^{1b}$)$_2$, —N($R^{1b}$)C(O)$R^{1b}$, —N($R^{1b}$)S(O)$_2R^{1b}$, —O$R^{1b}$—S$R^{1b}$, or a 5-6 membered heteroaryl or heterocyclyl having up to 3 atoms selected from nitrogen, oxygen, or sulfur, wherein each of said aliphatic or cycloaliphatic is optionally substituted with 1, 2, 3, or 4 occurrences of $J^R$;
each $J^R$ is independently fluoro, oxo, —C(O)$R^{1b}$, —C(O)N($R^{1b}$)$_2$, —C(O)O($R^{1b}$), —N($R^{1b}$)$_2$, —N($R^{1b}$)C(O)$R^{1b}$, —O$R^{1b}$, —S$R^{1b}$, phenyl, or a 5-6 membered heteroaryl or heterocyclyl having up to 4 atoms selected from nitrogen, oxygen, or sulfur, wherein said phenyl, heteroaryl, or heterocyclyl or $J^R$ is optionally substituted with 1 or 2 $R^{1c}$ groups;
each $R^{1b}$ is independently selected from hydrogen, $C_{1-4}$aliphatic, $C_{3-6}$cycloaliphatic, phenyl, benzyl, wherein each of said aliphatic, cycloaliphatic, phenyl, or benzyl of $J^{R1}$ is optionally substituted with up to three $R^{1c}$ groups;
each $R^{1c}$ is independently selected from chloro, fluoro, oxo, $C_{1-2}$alkyl, $C_{1-2}$alkyl substituted with 1-3 fluorine atoms, $C_{3-6}$cycloalkyl, —OH, —O$C_{1-2}$alkyl, or —O$C_{1-2}$alkyl substituted with 1-3 fluorine atoms;
$R^2$ is hydrogen, fluoro, chloro, $C_{1-6}$aliphatic, —O$C_{1-6}$aliphatic, $C_{3-6}$cycloaliphatic, —O$C_{3-6}$cycloaliphatic, cyano, —NH$_2$, —NH$C_{1-6}$ aliphatic, —NH$C_{3-6}$cycloaliphatic, —NHS(O)$_2C_{1-6}$aliphatic, —NHS(O)$_2C_{3-6}$cycloaliphatic, —NHS(O)$_2$phenyl, —NHS(O)$_2$benzyl, —NHS(O)$_2$heteroaryl, —S(O)$_2C_{1-6}$aliphatic, —S(O)$_2C_{3-6}$cycloaliphatic, —S(O)$_2$phenyl, —S(O)$_2$benzyl, —S(O)$_2$heteroaryl, —S(O)$_2$NH$C_{1-6}$aliphatic, —S(O)$_2$NH$C_{3-6}$cycloaliphatic, —S(O)$_2$NHphenyl, —S(O)$_2$NHbenzyl, or —S(O)$_2$NHheteroaryl, wherein said heteroaryl of $R^2$ is a 5- or 6-membered ring having 1, 2, or 3 atoms selected from N, O, or S, and wherein said aliphatic, cycloaliphatic, phenyl, benzyl, or heteroaryl of $R^2$ is optionally substituted with 1, 2, or 3 $R^{2a}$ groups;
each $R^{2a}$ is selected from chloro, fluoro, oxo, $C_{1-2}$alkyl, $C_{1-2}$alkyl substituted with 1-3 fluorine atoms, $C_{3-6}$cycloalkyl, —OH, —O$C_{1-2}$alkyl, or —O$C_{1-2}$alkyl substituted with 1-3 fluorine atoms; and
$R^3$ is hydrogen, fluoro, chloro, $C_{1-3}$aliphatic, cyclopropyl, —O$C_{1-3}$aliphatic, NH$_2$, or NH$C_{1-3}$aliphatic, wherein said aliphatic of $R^3$ is optionally substituted with up to 3 occurrences of fluoro.

In one embodiment, X is CH. In another embodiment, X is N.

In another embodiment, $R^1$ is a 5- or 6-membered heteroaryl ring having 1-3 heteroatoms selected from N, O, or S and optionally substituted with 1, 2, or 3 $R^{1a}$ groups.

In a further embodiment, $R^1$ is a pyridine, pyrimidine, pyrazine, pyridazine, thiazole, pyrazole, or thiadiazole ring, wherein each of said rings is optionally substituted with 1 or 2 independent occurrences of $R^{1a}$.

In yet another embodiment, $R^1$ is selected from

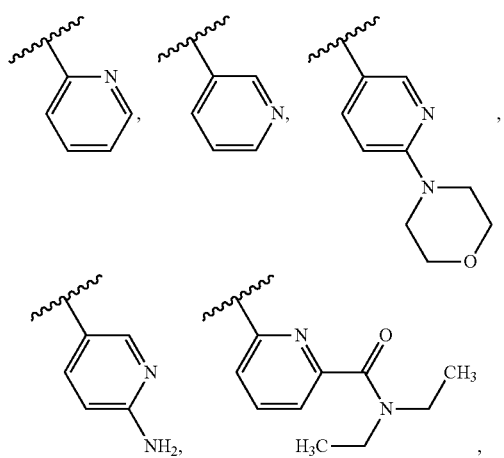

-continued

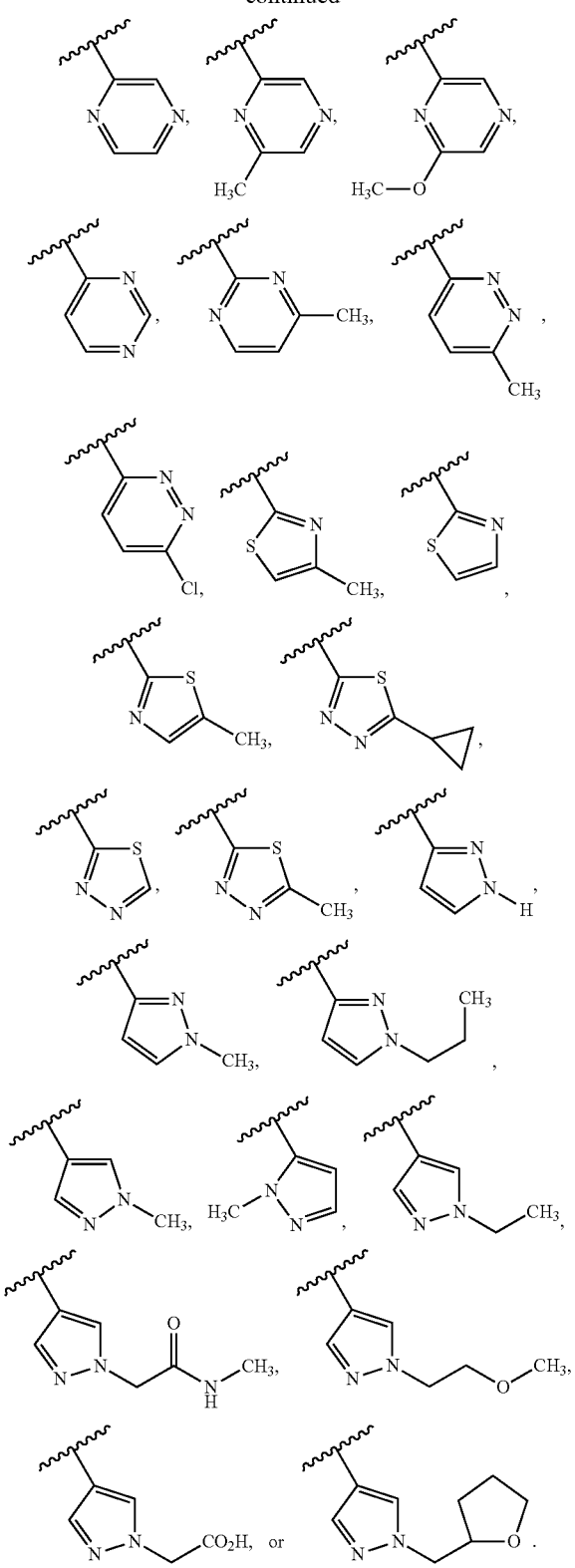

In another embodiment, $R^1$ is selected from a 9- or 10-membered fused bicyclic heteroaryl or heterocyclic ring system having 1, 2, or 3 heteroatoms selected from nitrogen, oxygen, or sulfur and optionally substituted with 1, 2, or 3 independent occurrences of $R^{1a}$.

In a further embodiment, $R^1$ is selected from

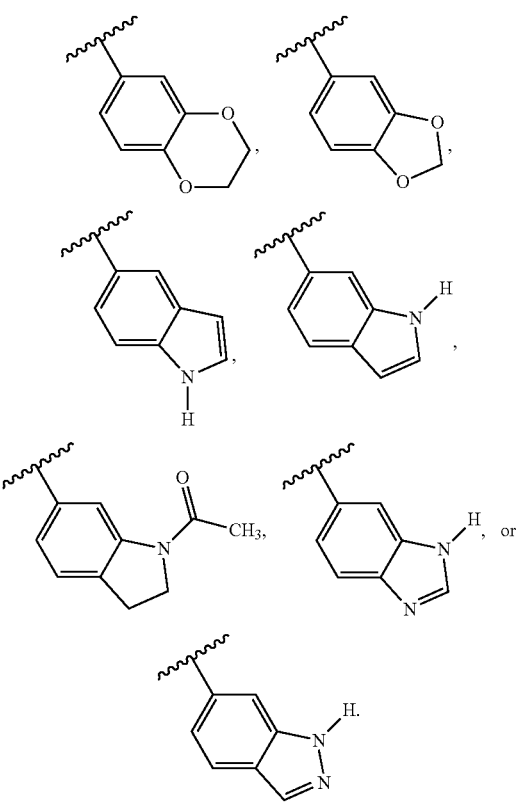

In another embodiment, $R^1$ is a phenyl ring optionally substituted with 1 or 2 independent occurrences of $R^{1a}$.

In a further embodiment, $R^1$ is selected from

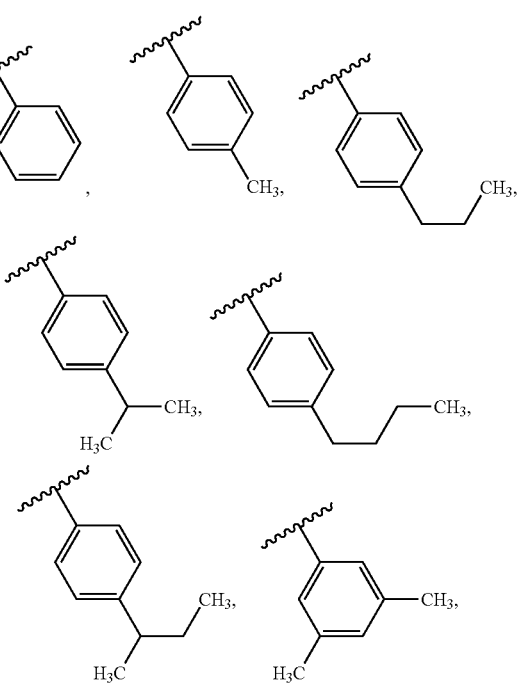

-continued
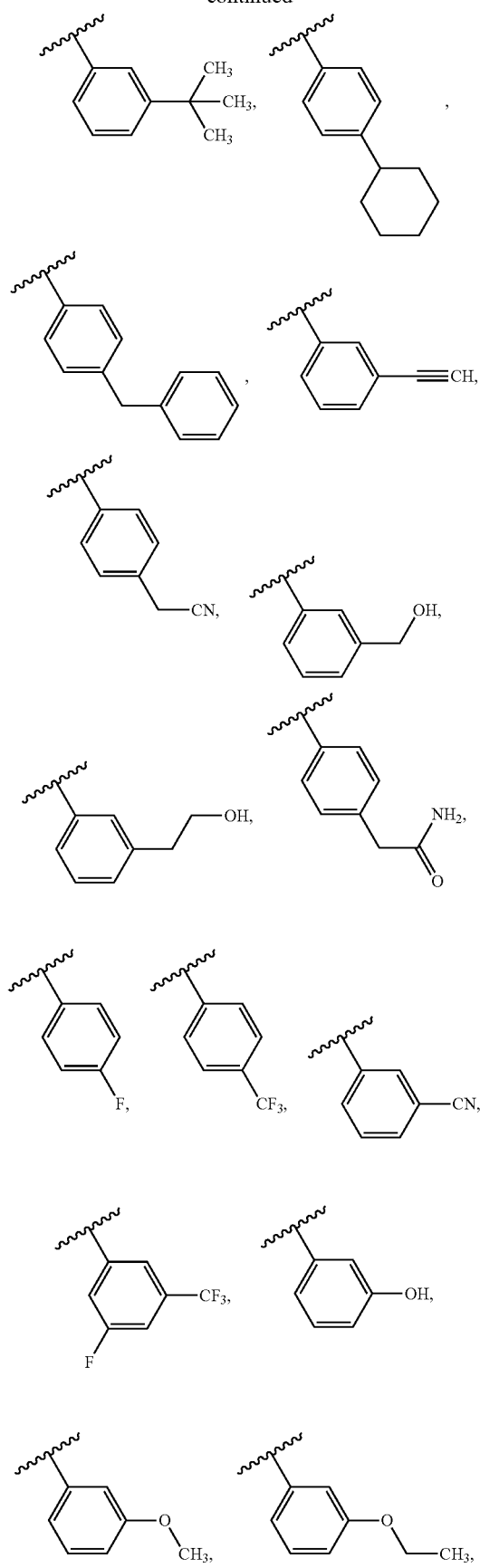
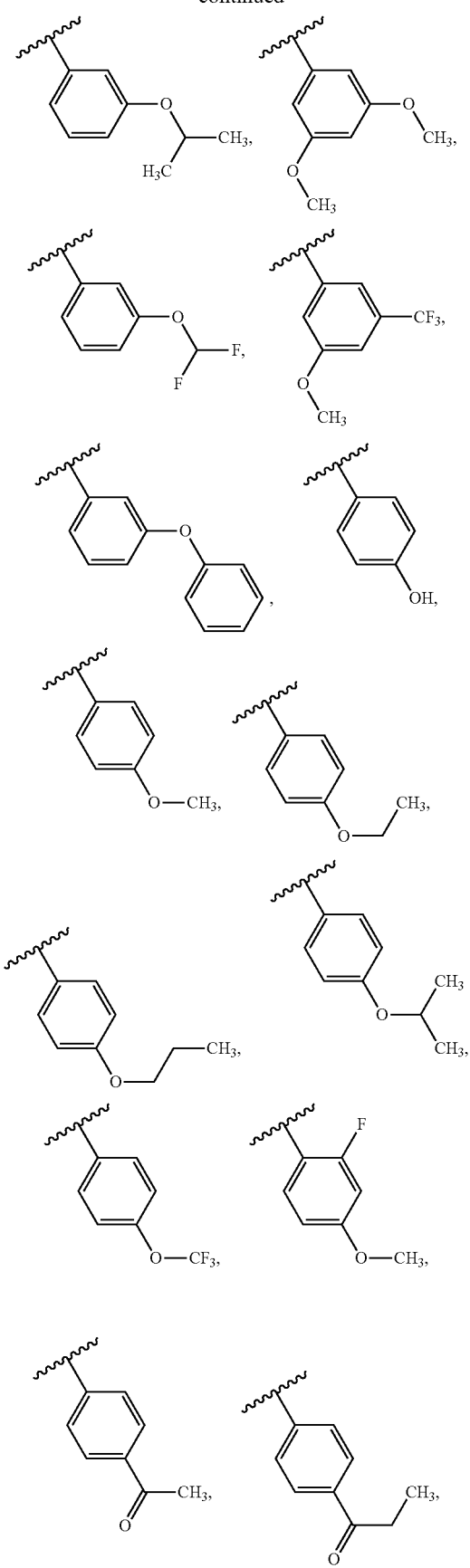

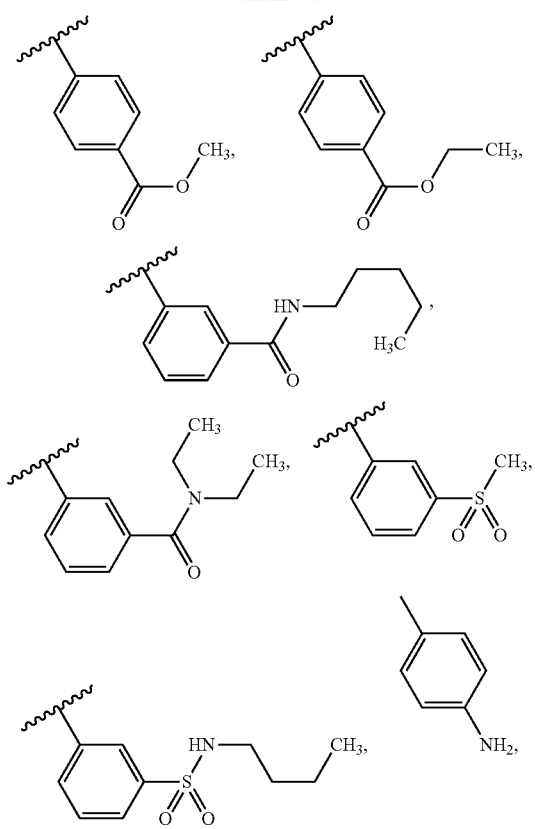

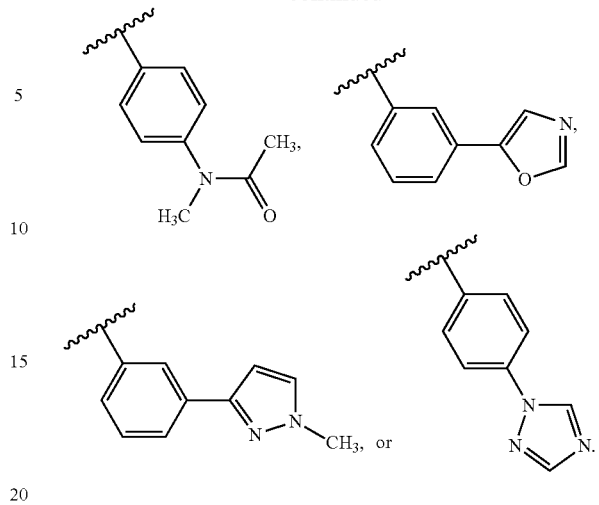

In another embodiment, $R^{1a}$ is chloro, fluoro, $C_{1-6}$ aliphatic, $C_{3-6}$ cycloaliphatic, —C(O)$R^{1b}$, —C(O)N($R^{1b}$)$_2$, —C(O)O($R^{1b}$), —S(O)$R^{1b}$, —S(O)$_2$N($R^{1b}$)$_2$, —N($R^{1b}$)$_2$, —N($R^{1b}$)C(O)$R^{1b}$, —N($R^{1b}$)S(O)$_2R^{1b}$, —O$R^{1b}$, or a 5-6 membered heteroaryl or heterocyclyl having up to 3 atoms selected from nitrogen, oxygen, or sulfur.

In yet another embodiment, each of $R^2$ and $R^3$ is a $C_{1-3}$aliphatic or —O$C_{1-3}$alkyl optionally substituted with up to three $R^{2a}$ groups. In a further embodiment, $R^2$ is —$C_{1-3}$alkyl or —$CF_3$.

In another embodiment,

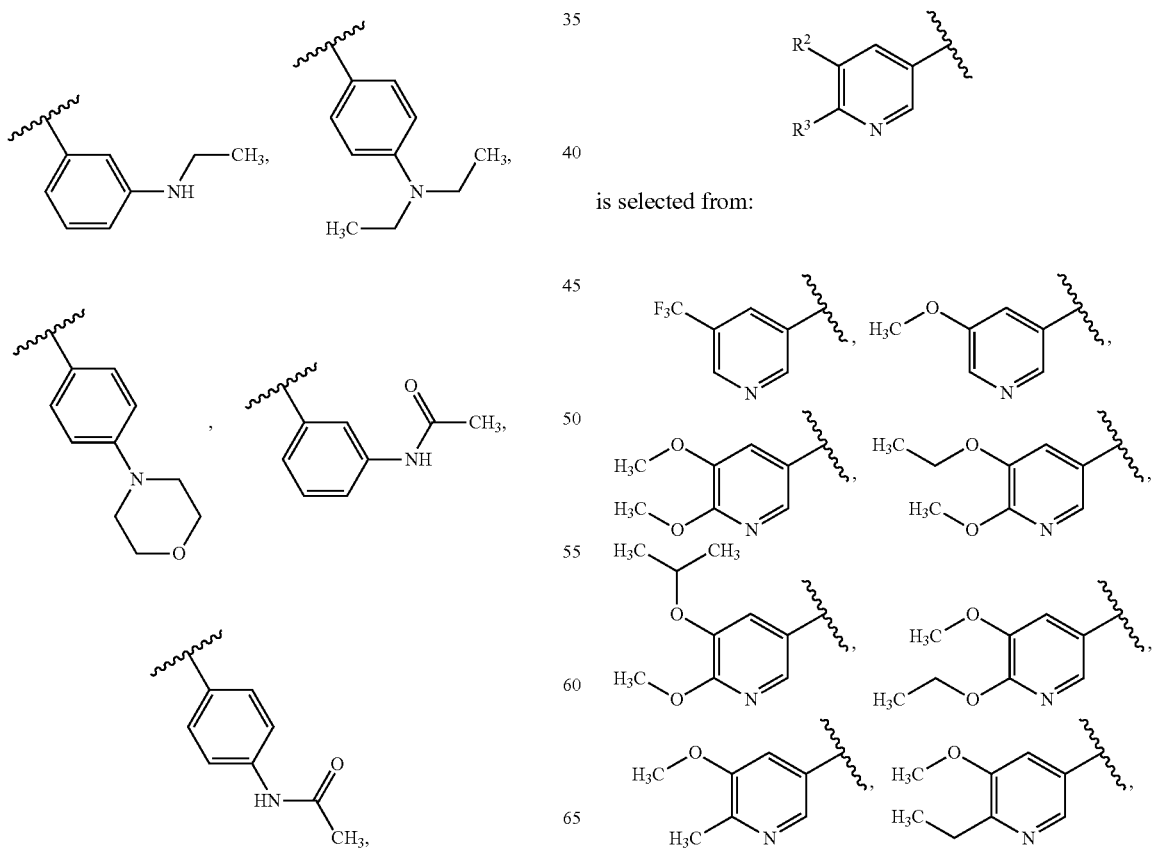

is selected from:

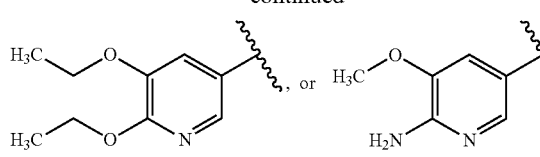
In yet another embodiment, the invention features a compound selected from the group of compounds listed in Table 1.
TABLE 1
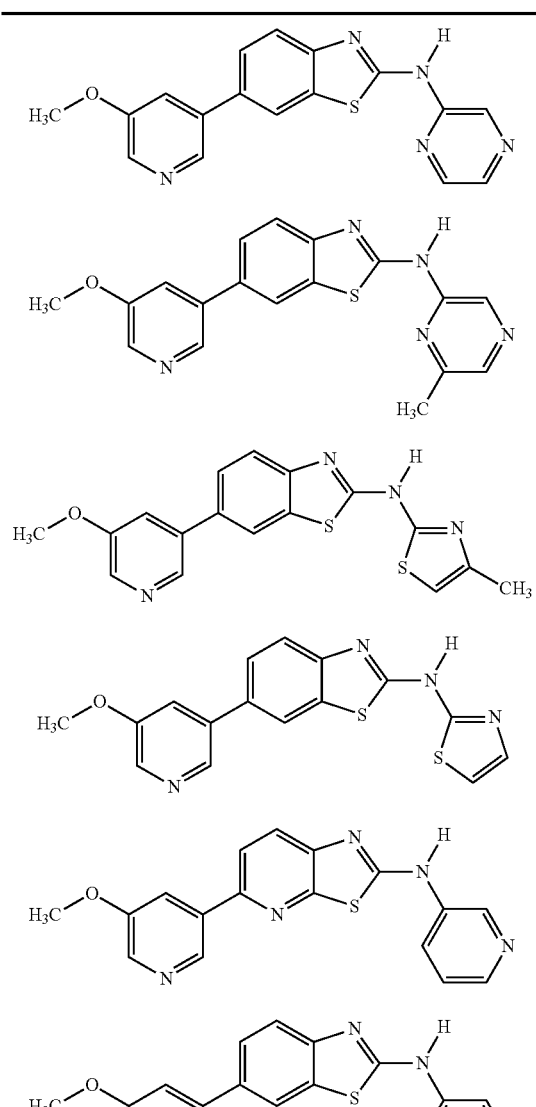
TABLE 1-continued
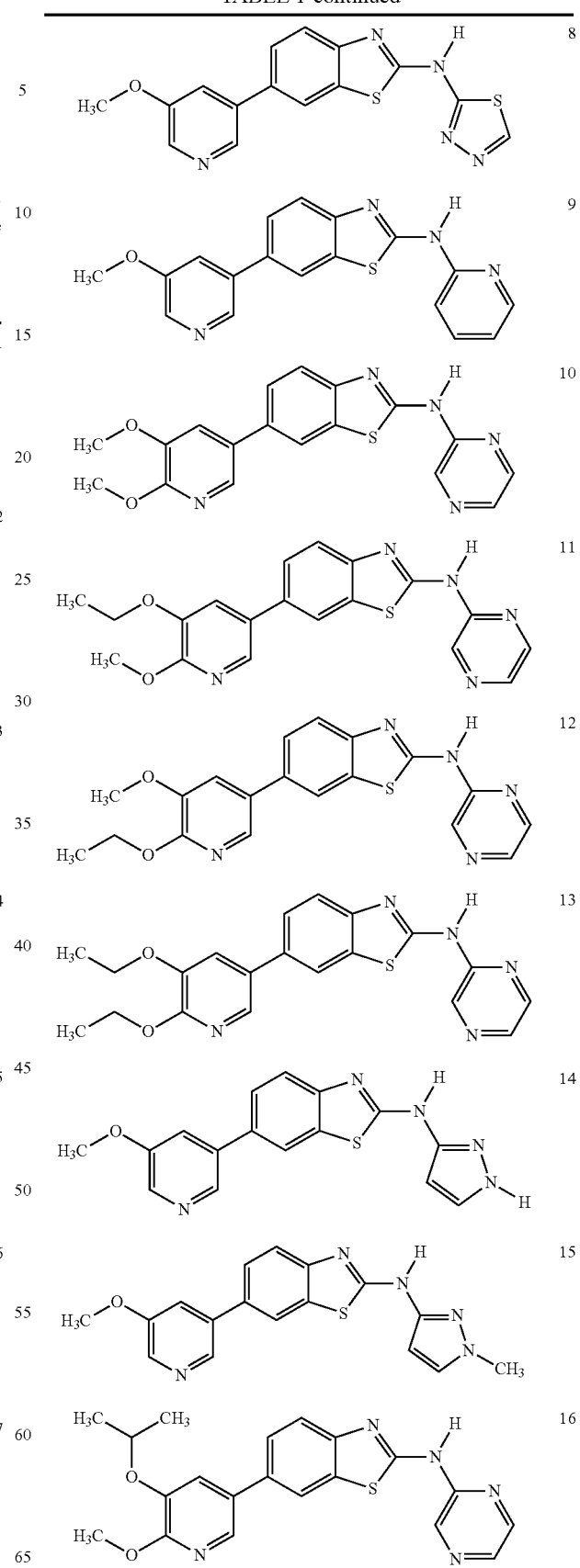

TABLE 1-continued
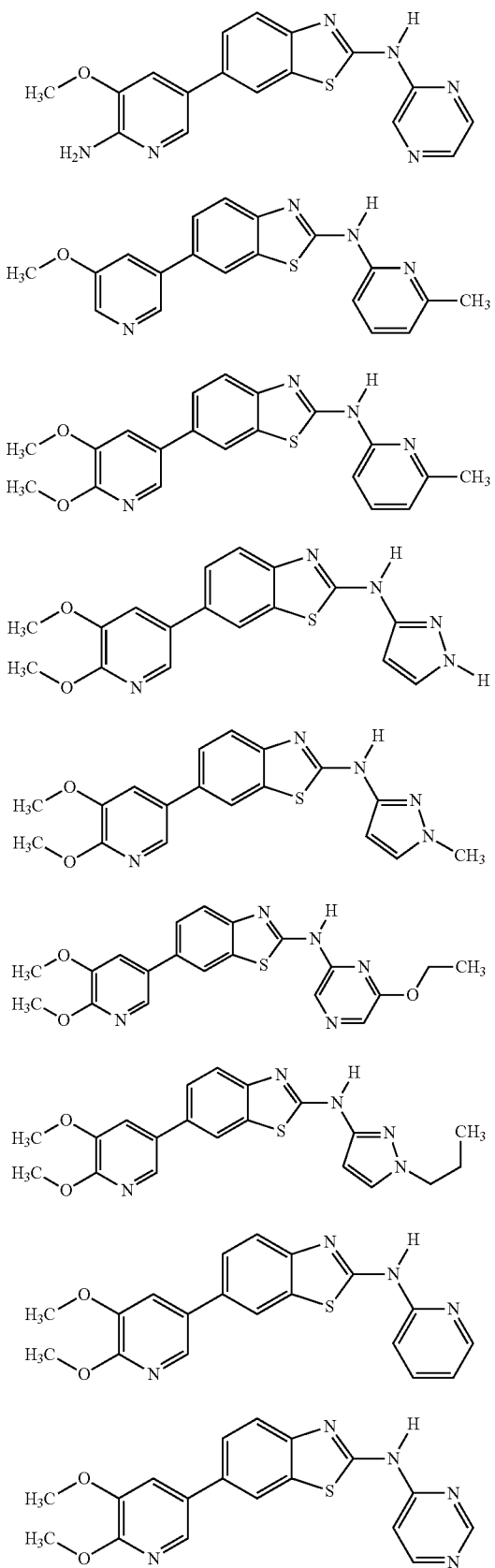
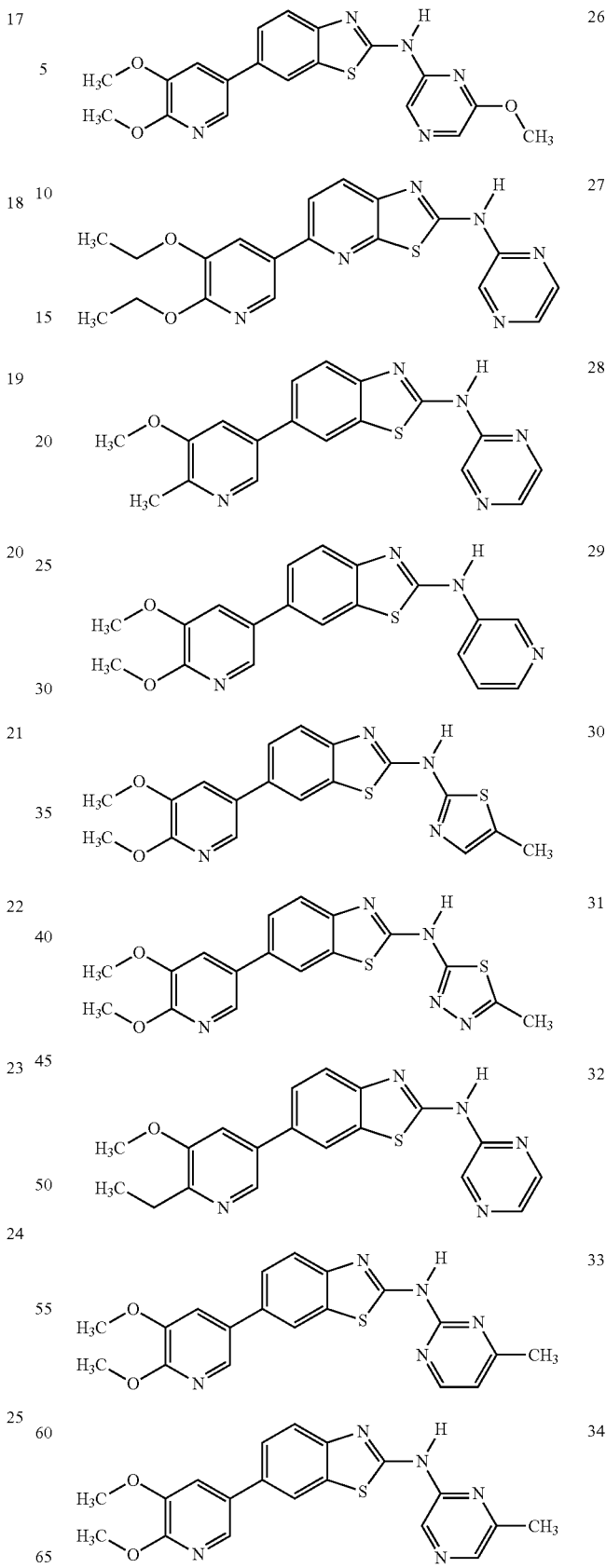

TABLE 1-continued
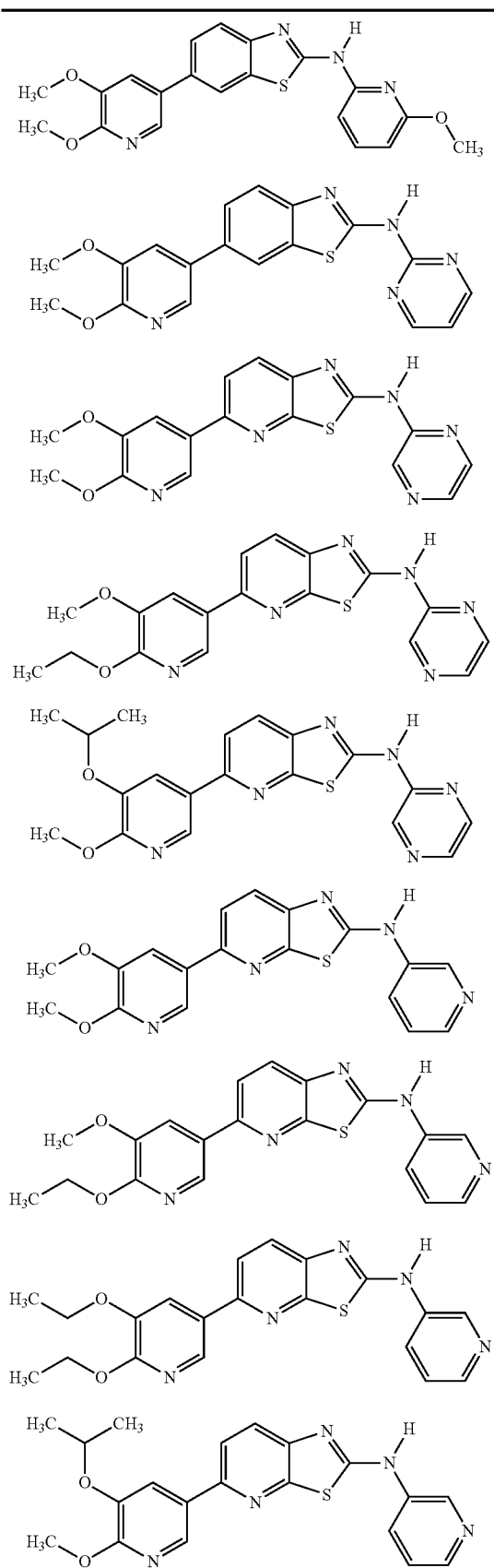
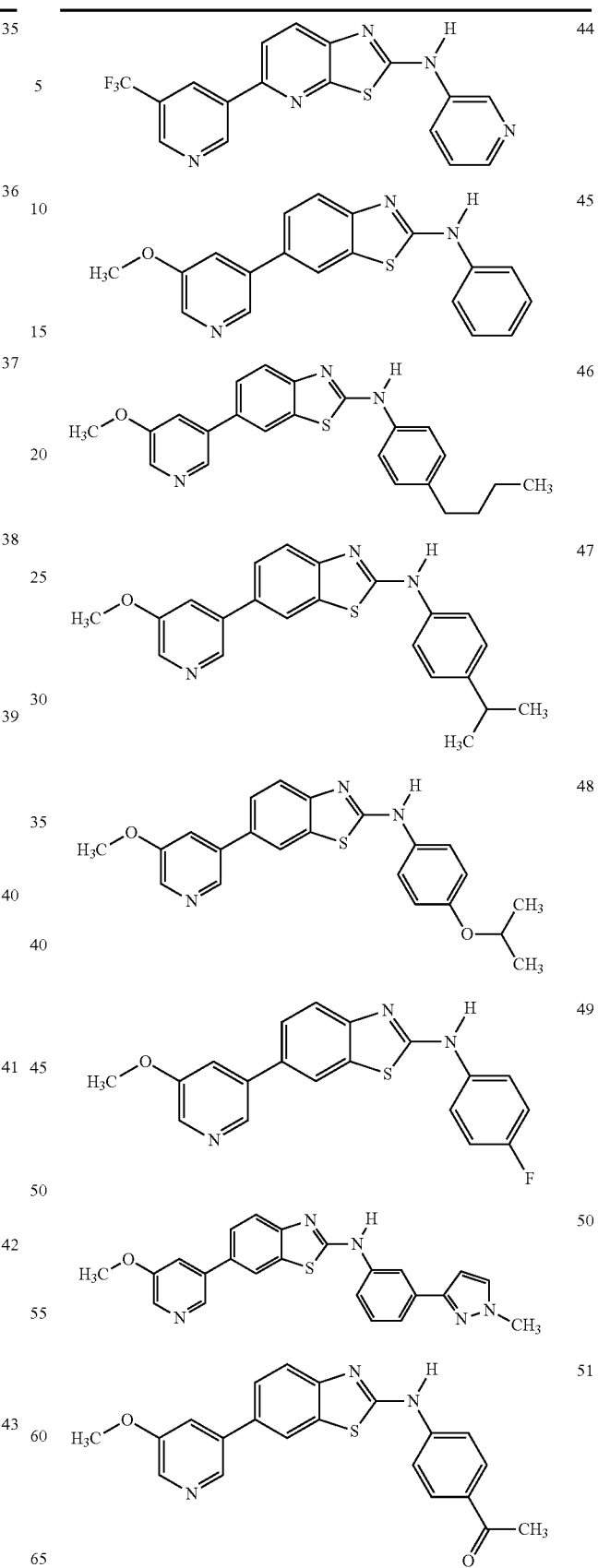

TABLE 1-continued
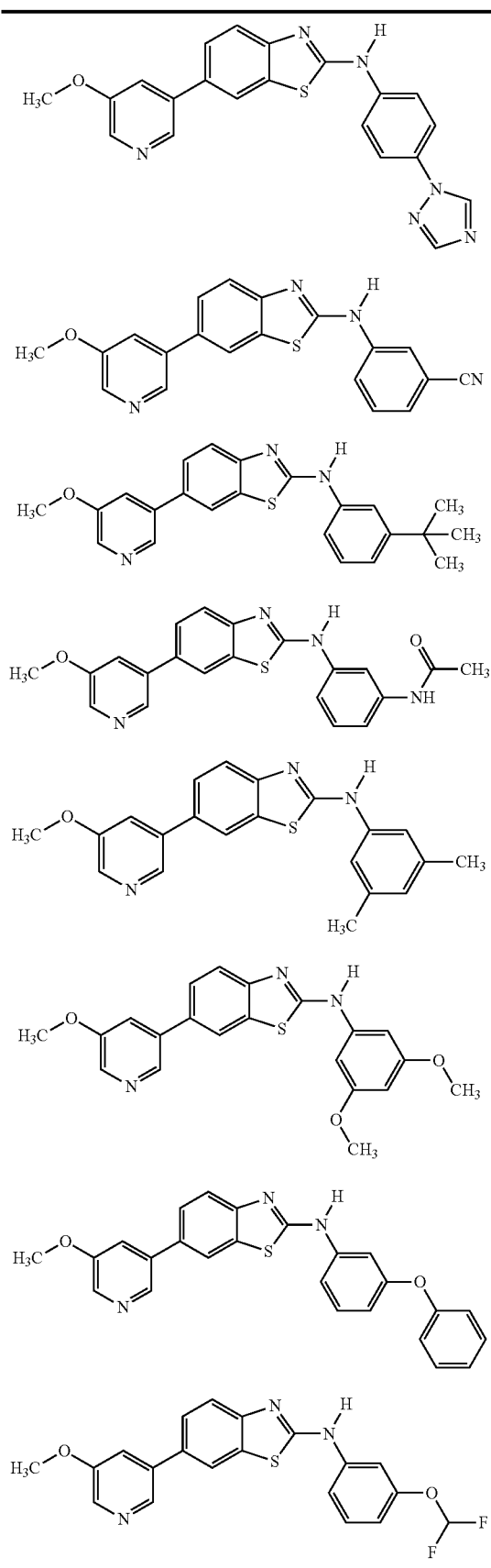
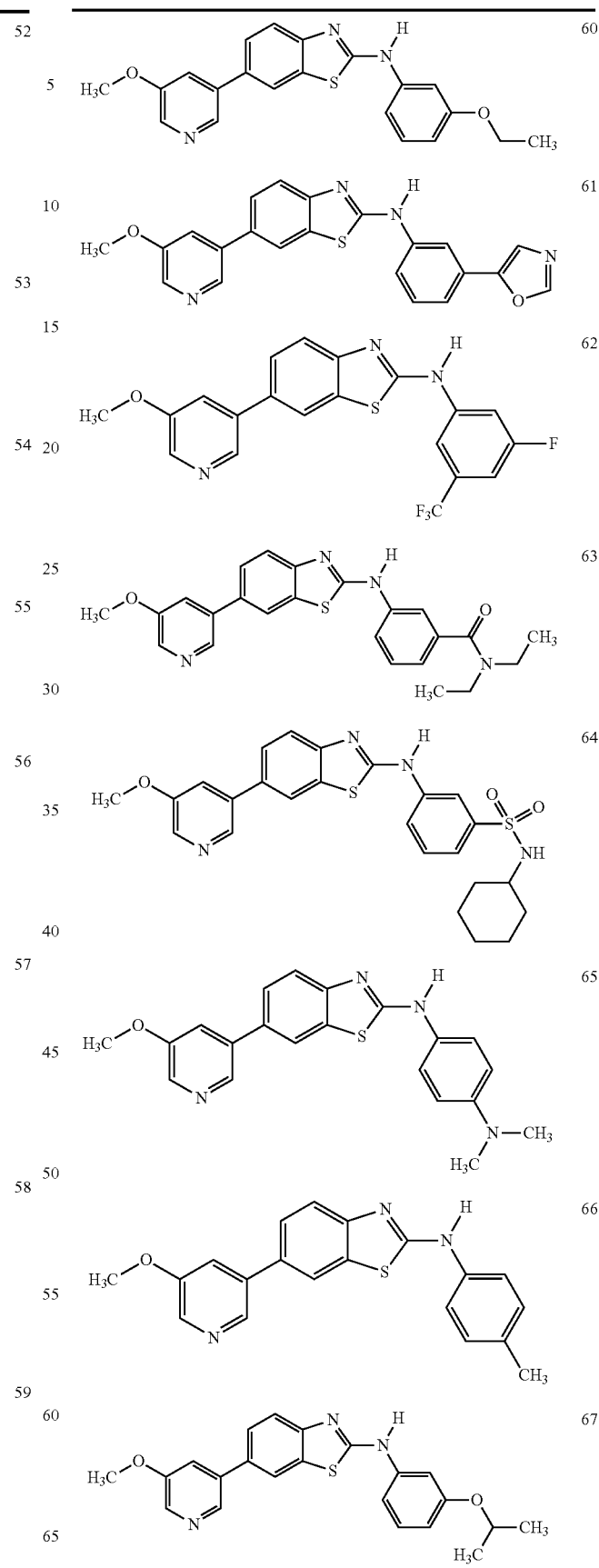

TABLE 1-continued
| | |
|---|---|
| 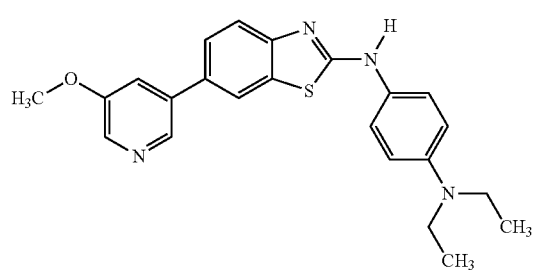 | 68 |
| 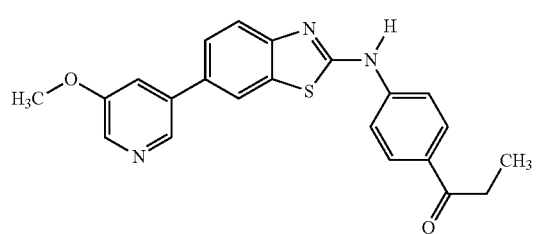 | 69 |
| 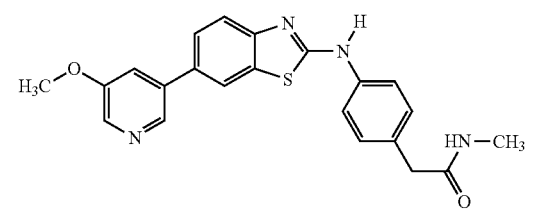 | 70 |
| 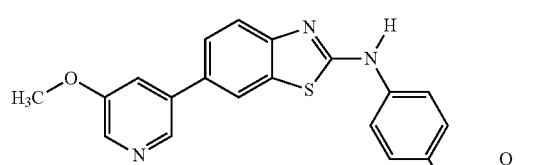 | 71 |
| 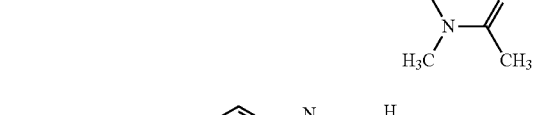 | 72 |
| 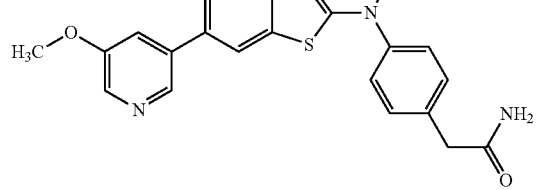 | 73 |
| 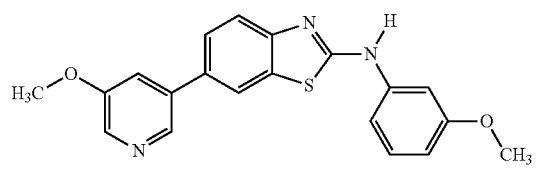 | 74 |
| 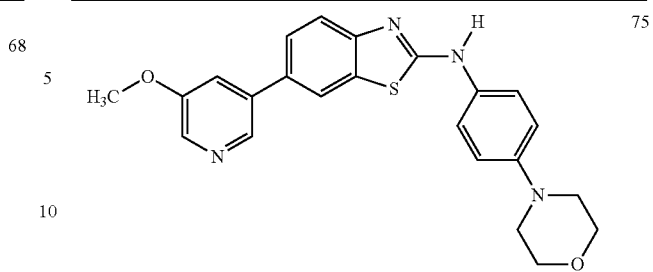 | 75 |
| 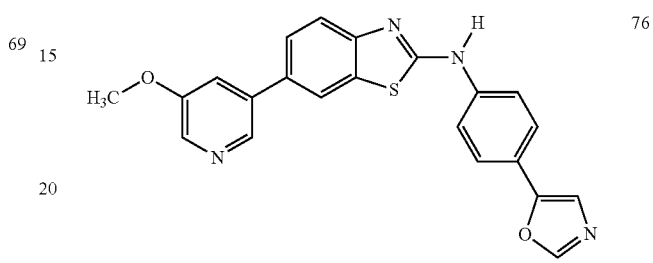 | 76 |
| 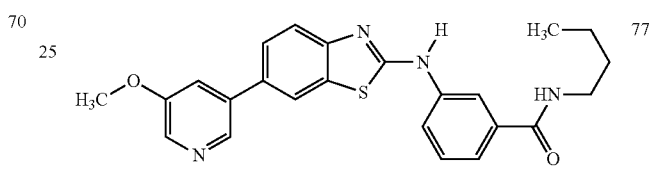 | 77 |
| 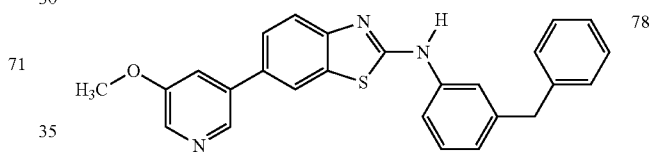 | 78 |
| 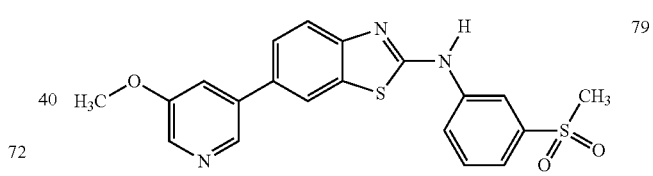 | 79 |
| 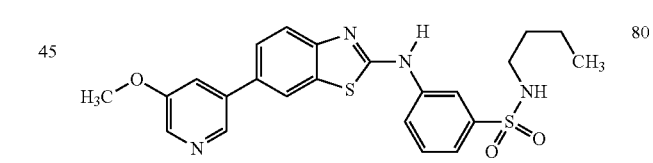 | 80 |
| 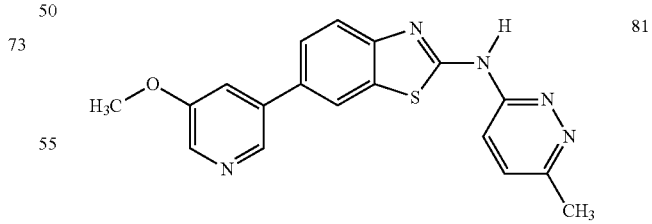 | 81 |
| 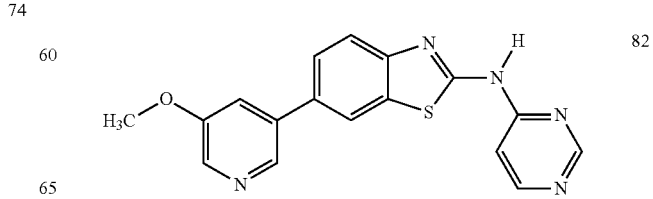 | 82 |

TABLE 1-continued
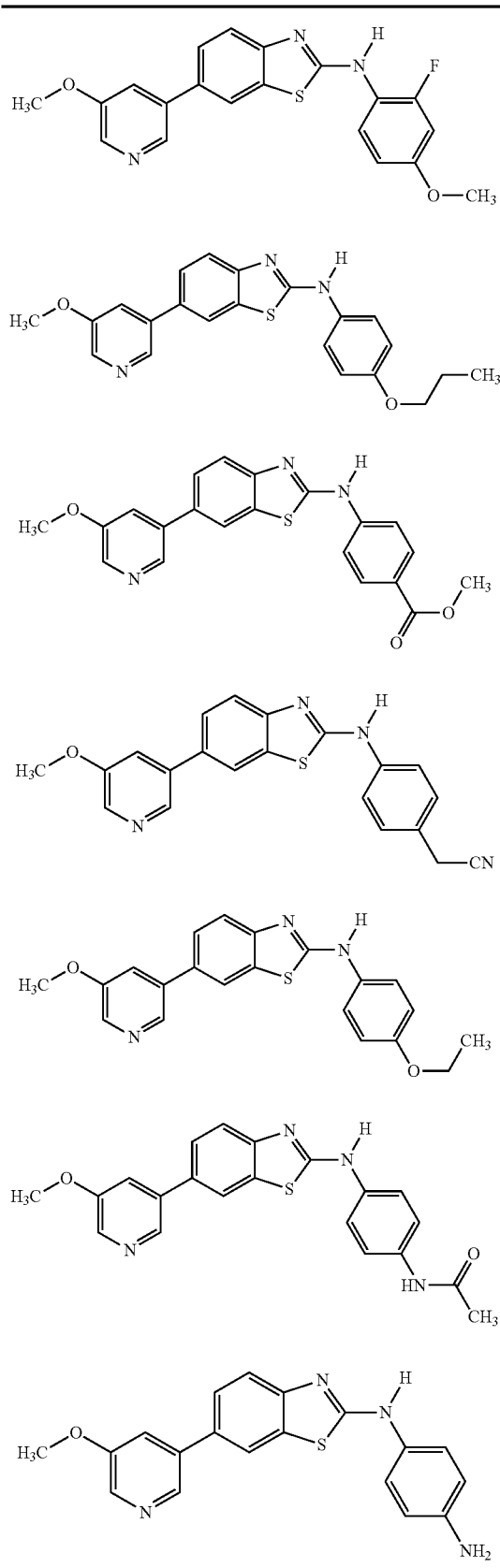
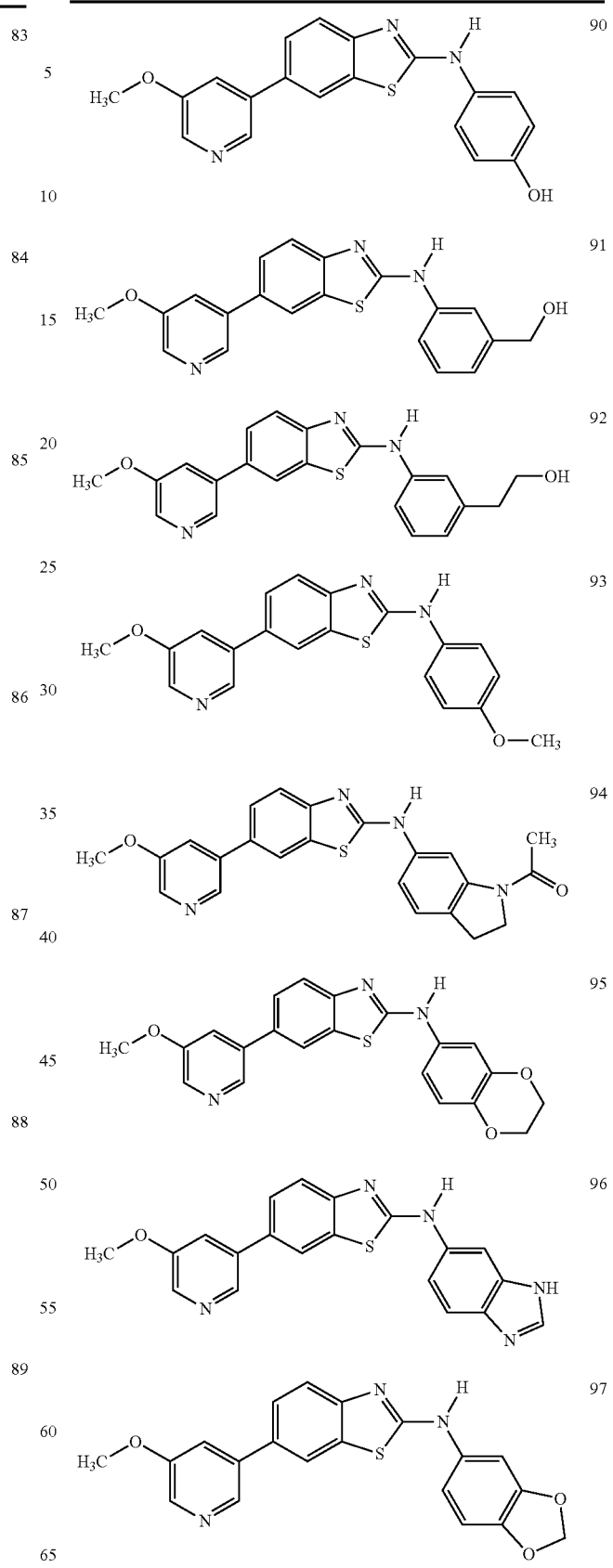

TABLE 1-continued
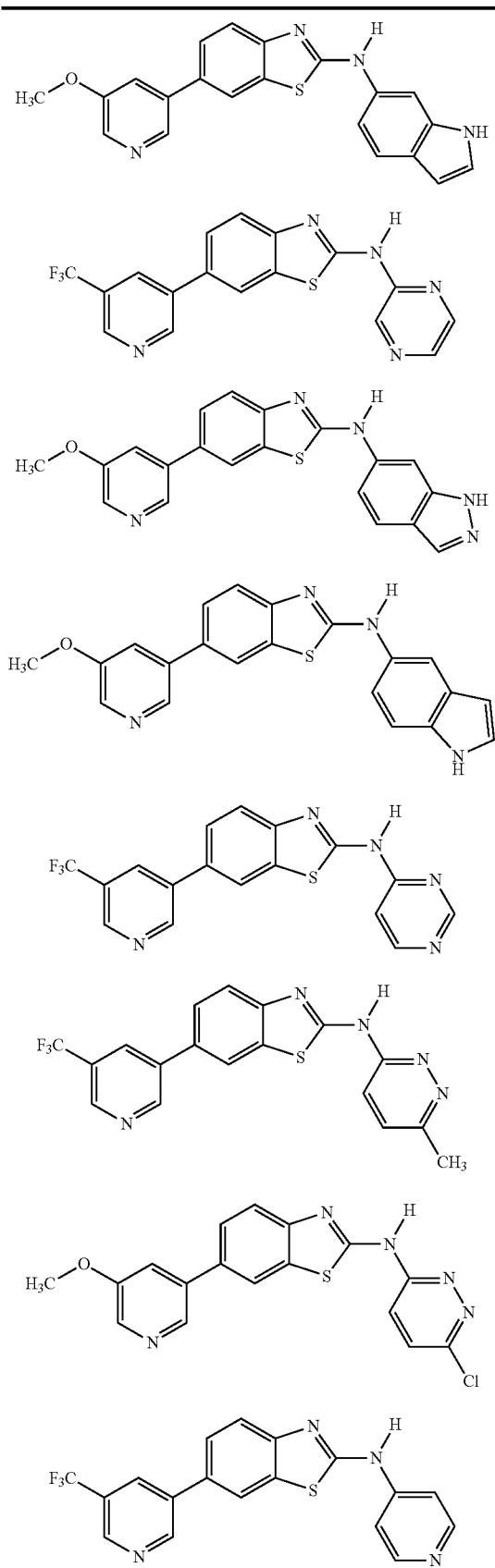
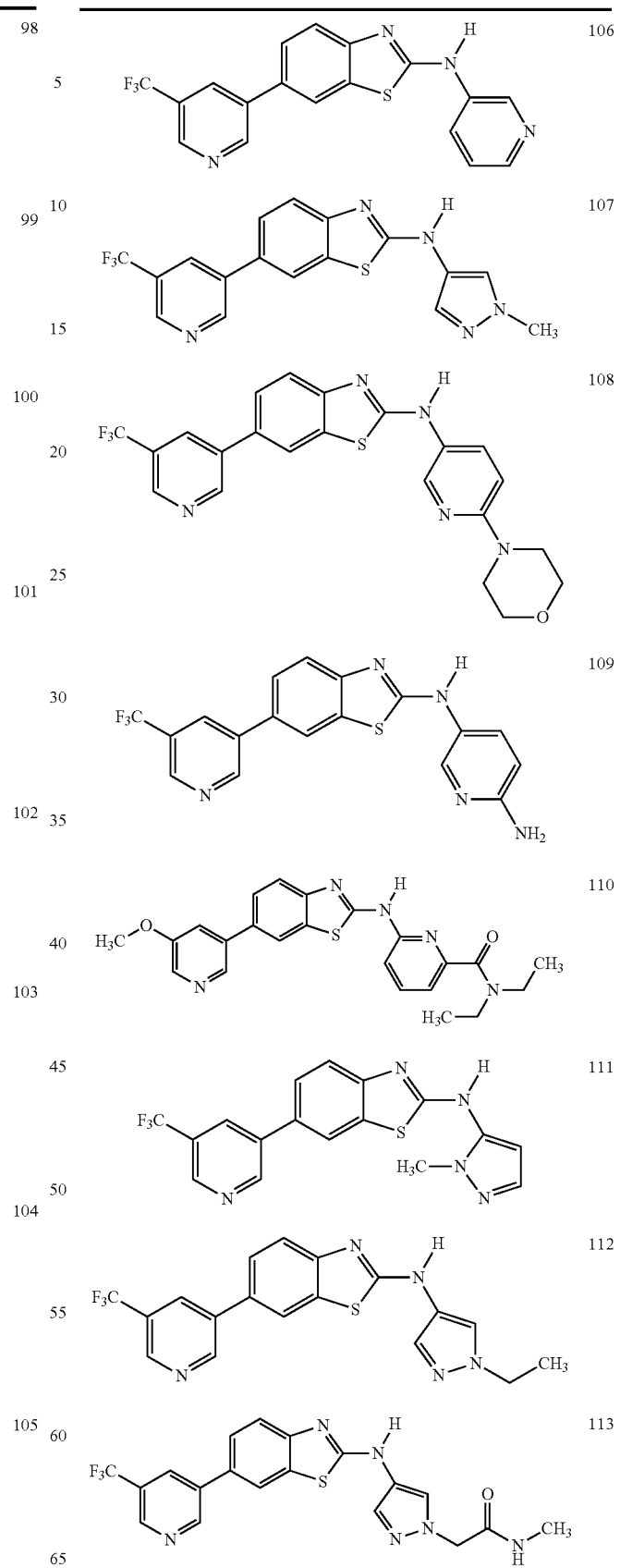

TABLE 1-continued

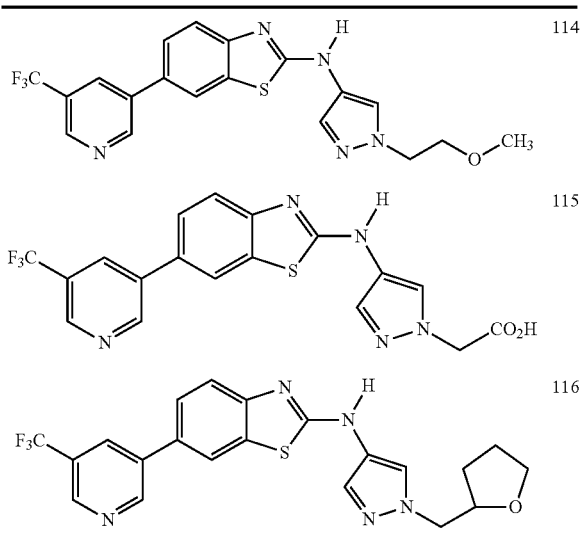

The invention also features a pharmaceutical composition comprising a compound of the invention and a pharmaceutically acceptable carrier, adjuvant, or vehicle.

Compositions, Formulations, and Administration of Compounds of the Invention

In another embodiment, the invention provides a pharmaceutical composition comprising a compound of any of the formulae or classes described herein. In a further embodiment, the invention provides a pharmaceutical composition comprising a compound of Table 1. In a further embodiment, the composition additionally comprises an additional therapeutic agent.

According to another embodiment, the invention provides a composition comprising a compound of this invention or a pharmaceutically acceptable derivative thereof and a pharmaceutically acceptable carrier, adjuvant, or vehicle. In one embodiment, the amount of compound in a composition of this invention is such that is effective to measurably inhibit a PI3K, particularly PI3Kγ, in a biological sample or in a patient. In another embodiment, the amount of compound in the compositions of this invention is such that is effective to measurably inhibit PI3Kα. In one embodiment, the composition of this invention is formulated for administration to a patient in need of such composition. In a further embodiment, the composition of this invention is formulated for oral administration to a patient.

The term "patient," as used herein, means an animal, preferably a mammal, and most preferably a human.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof. As used herein, the term "inhibitory active metabolite or residue thereof" means that a metabolite or residue thereof is also an inhibitor of PI3K.

As used herein, the term "pharmaceutically acceptable salt" refers to those salts which are, within the scope of sound medical judgment, suitable for use in contact with the tissues of humans and lower animals without undue toxicity, irritation, allergic response and the like.

Pharmaceutically acceptable salts are well known in the art. For example, S. M. Berge et al., describe pharmaceutically acceptable salts in detail in *J. Pharmaceutical Sciences*, 66:1-19, 1977, which is incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\ alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. In Remington: *The Science and Practice of Pharmacy*, 21st edition, 2005, ed. D. B. Troy, Lippincott Williams & Wilkins, Philadelphia, and *Encyclopedia of Pharmaceutical Technology*, eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intraocular, intrahepatic, intralesional, epidural, intraspinal, and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically—transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated, e.g., as micronized suspensions in isotonic, pH adjusted sterile saline or other aqueous solution, or, preferably, as solutions in isotonic, pH adjusted sterile saline or other aqueous solution, either with or without a preservative such as benzylalkonium chloride. Alternatively, for ophthalmic uses, the pharmaceutically acceptable compositions may be formulated in an ointment such as petrolatum. The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, dissolving or suspending the compound in an oil vehicle accomplishes delayed absorption of a parenterally administered compound form. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated." Examples of additional therapeutic agents are provided infra.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Uses of the Compounds and Compositions of the Invention

In one embodiment, the invention comprises a method of treating or lessening the severity of a PI3K-mediated condition or disease in a patient. The term "PI3K-mediated disease", as used herein means any disease or other deleterious condition in which a PI3K isoform is known to play a role. In one embodiment, the PI3K isoform is PI3Kγ. In another embodiment, the PI3K isoform is PI3Kα. In a further embodiment, the invention comprises a method of treating a PI3K-mediated disease. Such conditions include, without limitation, autoimmune diseases, inflammatory diseases, thrombolytic diseases, cancer, cardiovascular diseases, diabetes, allergic diseases, asthma and respiratory diseases.

In another embodiment, the invention provides a method of treating or lessening the severity of a PI3K-mediated condition or disease in the brain or spinal cord of a patient, the method comprising administering to said patient a compound or composition of the invention.

In another embodiment, the invention provides a method of treating or lessening the severity of cancer. Examples of cancers that may be treated or ameliorated by a method of the invention include, without limitation, cancer of the breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system. The invention also provides a method of treating or lessening the severity of leukemias, including, without limitation, acute lymphocytic leukemia (ALL), chronic myelogenous leukemia (CML), multiple myeloma and lymphomas. In one embodiment, the invention provides a method of treating or lessening the severity of cancer selected from ovarian cancer, colon cancer, colorectal cancer, breast cancer, brain cancer, and lung cancer.

In another embodiment, the invention provides a method of treating or lessening the severity of an autoimmune disease or disorder. Autoimmune diseases or disorders include, without limitation, rheumatoid arthritis, systemic lupus erythematosus (SLE), multiple sclerosis, glomerulonephritis, scleroderma, chronic thyroiditis, Graves' disease, autoimmune gastritis, type I diabetes, autoimmune hemolytic anemia, autoimmune neutropenia, thrombocytopenia, atopic dermatitis, myasthenia gravis, inflammatory bowel disease, ulcerative colitis, Crohn's disease, psoriasis, Sjogren's syndrome and graft vs. host disease. In one embodiment, the autoimmune disease or disorder is rheumatoid arthritis, SLE or multiple sclerosis. In another embodiment, the disease is multiple sclerosis.

In another embodiment, the invention provides a method of treating or lessening the severity of organ transplantation rejection.

In another embodiment, the invention provides a method of treating or lessening the severity of an inflammatory disease. Inflammatory diseases include, without limitation, chronic obstructive pulmonary disease (COPD), bronchitis, emphysema, farmer's lung and related diseases, eosinophilia, lung fibrosis, osteoarthritis, ankylosing spondylitis, sepsis, septic shock, inflammatory myopathies, meningitis, encephalitis, lacrimal parotid gland syndrome, acute respiratory distress syndrome and pancreatitis. In one embodiment, the inflammatory disease is acute respiratory distress syndrome or lacrimal parotid gland syndrome.

In another embodiment, the invention provides a method of treating or lessening the severity of allergic diseases or asthma. Examples of allergic diseases include, without limitation, perennial and seasonal allergic rhinitis, type I hypersensitivity reactions, atopic dermatitis, contact dermatitis, or eczema.

Compounds or compositions of the invention may be administered with one or more additional therapeutic agents, wherein the additional therapeutic agent is appropriate for the disease being treated and the additional therapeutic agent is administered together with a compound or composition of the invention as a single dosage form or separately from the compound or composition as part of a multiple dosage form. The additional therapeutic agent may be administered at the same time as a compound of the invention or at a different time. In the latter case, administration may be staggered by, for example, 6 hours, 12 hours, 1 day, 2 days, 3 days, 1 week, 2 weeks, 3 weeks, 1 month, or 2 months.

The invention provides a method of inhibiting PI3K kinase activity in a biological sample that includes contacting the biological sample with a compound or composition of the invention. The term "biological sample," as used herein, means a sample outside a living organism and includes, without limitation, cell cultures or extracts thereof; biopsied material obtained from a mammal or extracts thereof; and blood, saliva, urine, feces, semen, tears, or other body fluids or extracts thereof. Inhibition of kinase activity, particularly PI3K kinase activity, in a biological sample is useful for a variety of purposes known to one of skill in the art. Examples of such purposes include, but are not limited to, biological specimen storage and biological assays. In one embodiment, the method of inhibiting PI3K kinase activity in a biological sample is limited to non-therapeutic methods.

Preparation of Compounds of the Invention

As used herein, all abbreviations, symbols and conventions are consistent with those used in the contemporary scientific literature. See, e.g., Janet S. Dodd, ed., *The ACS Style Guide: A Manual for Authors and Editors*, 2nd Ed., Washington, D.C.: American Chemical Society, 1997. The following definitions describe terms and abbreviations used herein:
ATP adenosine triphosphate
Boc t-butoxylcarbonyl
Brine a saturated NaCl solution in water
DCM dichloromethane
DIEA diisopropylethylamine
DMF dimethylformamide
DMSO methylsulfoxide
DTT dithiothreitol
ESMS electrospray mass spectrometry
$Et_2O$ ethyl ether
EtOAc ethyl acetate
EtOH ethyl alcohol
HEPES 4-(2-hydroxyethyl)-1-piperazineethanesulfonic acid
HPLC high performance liquid chromatography
LC-MS liquid chromatography-mass spectrometry
Me methyl
MeOH methanol
NBS N-bromosuccinimide
NMP N-methylpyrrolidone
Ph phenyl
RT or rt room temperature
tBu tertiary butyl
tBuOH tert-butanol
TCA trichloroacetic acid
THF tetrahydrofuran
TEA triethylamine
TFA trifluoacetic acid Unless otherwise indicated, purifications by reversed-phase HPLC were conducted on a Waters 20×100 mm YMC-Pack Pro C18 column using a linear water/acetonitrile (0.1% TFA, 0.2% formic acid, or 5 mmol ammonium formate) gradient at a flow rate of 28 mL/minute.

General Synthetic Procedures

In general, the compounds of this invention may be prepared by methods described herein or by other methods known to those skilled in the art.

EXAMPLE 1

General Preparation of the Compounds of Formula I

The preparation of compounds of formula I, wherein $R^1$ is a phenyl or a heteroaryl ring is shown in Scheme 1. As shown in the scheme, the heteroaryl halide of formula A1, in which the amine is protected, is boronated. Procedures for preparing a boronate or boronic acid from an aryl halide are described in *Boronic Acids*, ISBN: 3-527-30991-8, Wiley-VCH, 2005 (Dennis G. Hall, editor). In one example, the halogen is bromine and a boronate is prepared by reacting the aryl bromide with 4,4,5,5-tetramethyl-2-(4,4,5,5-tetramethyl-1,3,2-dioxaborolan-2-yl)-1,3,2-dioxaborolane to produce a compound of formula A2, where —$B(OR)_2$ is a 4,4,5,5-tetramethyl-1,3,2-dioxaborolan-2-yl moiety. The compound of formula A2 is reacted with a compound of formula A4, where $R^2$ and $R^3$ are as defined for a compound of formula I and halogen represents a chloro, bromo, or iodo group, to produce a compound of formula A5. Alternatively, a compound of formula A4 can be boronated as described above to produce a compound of formula A3, which can subsequently be reacted with a compound of formula A1 to produce a compound of formula A5. Removal of the amine protecting group of a compound of formula A5 provides a compound of formula I.

Another way of providing a compound of formula I is to react a compound of formula A6 with thiophosgene under basic conditions, as shown in Scheme 1, to produce isothiocyanate A7. Subsequent reaction of a compound of formula A7 with an amine provides a compound of formula A9, formed through the thiourea intermediate having formula A8. As described above, reaction of a compound of formula A9 with a boronate of formula A3 provides a compound having formula I.

As shown in Scheme 1, yet another way of providing a compound of formula I is to react a primary amine with a haloheteroaromatic ring of formula A10 in the presence of cesium carbonate to form a compound of formula A11, wherein $R^1$ of the amine is a substituted or unsubstituted phenyl or heteroaryl ring. Reaction of the compound of formula A11 with a boronate of formula A3 provides a compound of formula Ia (a compound of formula I wherein X is CH).

In general, the compounds of this invention may be prepared by methods described herein or known to those skilled in the art for the preparation of analogous compounds. In order that the invention described herein may be more fully understood, the following examples are set forth. It should be understood that these examples are for illustrative purposes only and are not to be construed as limiting this invention in any manner.

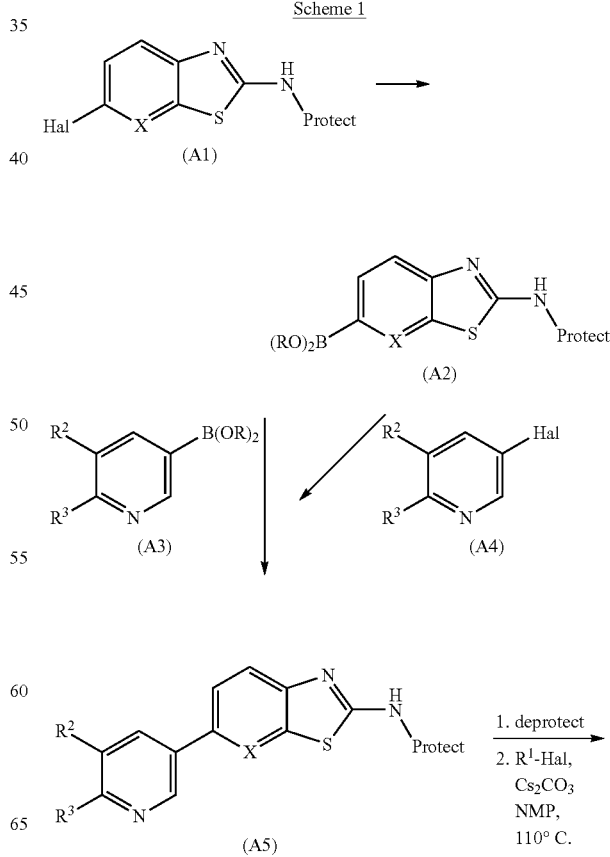

Scheme 1

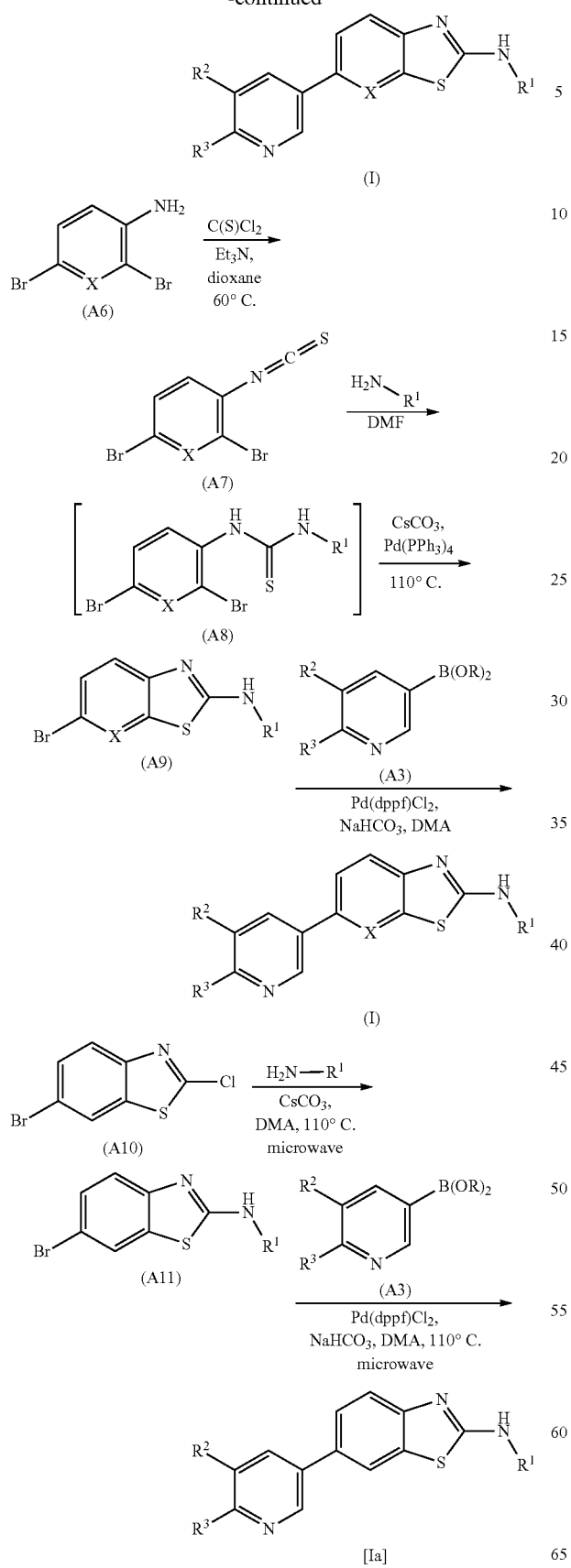

EXAMPLE 2

Preparation of 3-ethoxy-2-methoxy-5-bromopyridine (Compound 1004)

As shown in step 2-i of Scheme 2, to 4.0 g (0.1 mol, 60% in mineral oil) NaH in a 100 mL DMF suspension was added 10 mL of an absolute ethyl alcohol (4.6 g, 0.1 mol)/DMF solution at RT. After the evolution of hydrogen gas, the reaction mixture was stirred at RT for 30 minutes and the resulting ethoxide solution transferred to a solution of 3,5-dibromopyridine (11.84 g, 0.05 mol, obtained from Aldrich Chemical Co.) in 100 mL DMF at 60° C. The reaction was stirred at 60° C. for 4 hours and the mixture was allowed to come to RT. Brine and ethyl acetate were added and the organics were partitioned, dried over MgSO$_4$, filtered, and the volatiles removed under reduced pressure. The resulting crude material was purified by silica chromatography, with the desired product eluting with 20% ethyl acetate/hexanes. 3-Bromo-5-ethoxypyridine (Compound 1001, 4.25 g) was obtained as the pure product (42% yield): $^1$H NMR (CDCl$_3$) δ 8.3 (dd, 2H), 7.4 (d, 1H), 4.12 (q, 2H), 1.45 (t, 3H). 3-Benzyloxy-5-bromopyridine was prepared by an analogous procedure: $^1$H NMR (CDCl$_3$) δ 8.33 (d, 2H), 7.5-7.35 (m, 6H), 5.15 (s, 2H).

Alternatively, as shown in step 2-ii of Scheme 2,3-bromo-5-hydroxypyridine (100 mg, 0.57 mmol, obtained from Aldrich Chemical Co.) was diluted with DMF (3 mL). Potassium carbonate (158.8 mg, 1.15 mmol) was added, followed by the addition of bromoethane (62.6 mg, 42.6 µL, 0.57 mmol). The mixture was warmed to 60° C. and stirred overnight. After cooling, the mixture was dissolved in ethyl acetate and washed with 2 M NaOH, followed by water. The organics were dried over sodium sulfate, filtered, and the volatiles removed under reduced pressure. The resulting crude 3-bromo-5-ethoxypyridine (Compound 1001) was used without further purification. The following compounds were made by an analogous procedure: 3-bromo-5-propoxypyridine, ESMS (M+H) 218.19/216.19; 3-bromo-5-butylpyridine, ESMS (M+H) 230.22/232.22; 3-bromo-5-(cyclohexylmethoxy)pyridine, ESMS (M+H) 270.2/272.22; 3-(2-fluoroexthoxy)-5-bromopyridine, ESMS (M+H) 220.14/222.14; 3-(2,2-difluoroexthoxy)-5-bromopyridine; and 3-(2-ethylbutoxy)-5-bromopyridine, ESMS (M+H) 258.33/256.33.

As shown in step 2-iii of Scheme 2,3-chloroperoxybenzoic acid (9.426 g, 42.06 mmol) was added to 3-bromo-5-methoxypyridine (4.25 g, 21 mmol) in 200 mL of DCM at RT. The reaction was stirred overnight and the mixture was washed with 200 mL of 2 N NaOH and 2×200 mL brine. The organic phase was dried over MgSO$_4$, filtered and the volatiles removed under reduced pressure to provide 3-bromo-5-ethoxypyridine, 1-oxide (Compound 1002, 4.4 g): $^1$H NMR (CDCl$_3$): δ 8.05 (s, 1H), 7.9 (s, 1H), 7.0 (s, 1H), 4.12 (q, 2H), 1.45 (t, 3H).

As shown in step 2-iv of Scheme 2, phosphorous oxychloride (48.02 g, 403.6 mmol) was added to 3-bromo-5-ethoxypyridine, 1-oxide (4.4 g, 20.18 mmol) in 700 mL of DCM at RT. The reaction mixture was stirred at RT overnight. After the addition of brine, the organics were partitioned, dried over MgSO$_4$, filtered, and the filtrate concentrated under reduced pressure. The product was purified by filtering the concentrate through a pad of silica gel and eluting the pad with ethyl acetate. The volatiles were removed under reduced pressure to provide 5-bromo-2-chloro-3-ethoxypyridine (Compound 1003, 4.3 g, 85.6%): $^1$H NMR (CDCl$_3$) δ 8.1 (s, 1H), 7.32 (s, 1H), 4.15 (q, 2H), 1.6 (t, 3H).

As shown in step 2-v of Scheme 2, 40.51 mL of a 25% MeONa/MeOH solution was added to 5-bromo-2-chloro-3-ethoxypyridine (4.3 g, 17.27 mmol). The reaction mixture was refluxed for 2 hours. After cooling, ethyl acetate and brine were added to the mixture. The organic phase was dried with MgSO₄, filtered, and evaporated under reduced pressure. After purification via silica gel chromatography, 5-bromo-3-ethoxy-2-methoxypyridine (Compound 1004, 2.1 g, 50% yield) was obtained: ¹H NMR (CDCl₃) δ 7.8 (s, 1H), 7.15 (s, 1H), 4.1 (q, 2H), 4.0 (s, 3H), 1.5 (t, 3H). The following compounds were synthesized by an analogous procedure: 5-Bromo-3-isopropoxy-2-methoxypyridine: ¹H NMR (CDCl₃) δ 7.7 (s, 1H), 7.1 (s, 1H), 4.55-4.5 (m, 1H), 3.9 (s, 3H), 1.3 (d, 6H); 5-bromo-2-ethoxy-3-methoxypyridine: ESMS (M+H) 232, 234; 5-bromo-3-methoxy-2-propoxypyridine: ESMS (M+H) 246, 248; 5-bromo-2-isopropoxy-3-methoxypyridine: ESMS (M+H) 246, 248; 5-bromo-2-(2,2-difluoroethoxy)-3-methoxypyridine: ESMS (M+H) 268, 270; 5-bromo-2,3-diethoxypyridine: ESMS (M+H) 246, 248; 5-bromo-2-(2,2-difluoroethoxy)-3-ethoxypyridine: ESMS (M+H) 282, 284; 5-bromo-3-ethoxy-2-propoxypyridine: ESMS (M+H) 260, 262; 5-bromo-3-ethoxy-2-isopropoxypyridine: ESMS (M+H) 260, 262; 5-bromo-3-(2-fluoroethoxy)-2-methoxypyridine: ESMS (M+H) 250, 252; 5-bromo-2-methoxy-3-propoxypyridine: ESMS (M+H) 246, 248; 5-bromo-2-methoxy-3-(2-methoxyethoxy)pyridine: ESMS (M+H) 262, 264; 5-bromo-3-(2,2-difluoroethoxy)-2-methoxypyridine: ¹H NMR (CDCl₃) δ 7.9 (d, 1H), 7.2 (d, 1H), 6.1 (tt, 1H), 4.4 (q, 2H), 4.2 (td, 2H), 1.4 (t, 3H); 5-bromo-2-ethoxy-3-isopropoxypyridine: ¹H NMR (CDCl₃) δ 7.7 (d, 1H), 7.1 (d, 1H), 4.4 (m, 1H), 4.3 (q, 2H), 1.3 (m, 9H); 5-bromo-3-butoxy-2-methoxypyridine: ESMS (M+H) 260, 262; 5-bromo-2-methoxy-3-(2,2,2-trifluoroethoxy)pyridine: ESMS (M+H) 286, 288; and 5-bromo-2-ethoxy-3-(2,2,2-trifluoroethoxy)pyridine: ESMS (M+H) 300, 302.

Also prepared by a procedure analogous to that of step 2-v were 5-methoxy-3-bromopyridine, 2,3-dimethoxy-5-bromopyridine, 2,3-diethoxy-5-bromopyridine, 2-methoxy-3-propoxy-5-bromopyridine, and 2-methoxy-3-(2-methoxyethoxy)-5-bromo)pyridine.

(4.71 g, 30.9 mmol, obtained from Lancaster Synthesis, Inc.) and anhydrous potassium carbonate (2.56 g; 18.5 mmol). The reaction mixture was heated in an oil bath at 100° C. for 2 hours. Another equivalent of sodium chlorodifluoroacetate and 1.2 equiv. of potassium carbonate were added and heating continued for an additional 2.0 hours. After this time, the reaction was cooled and the volatiles removed under reduced pressure. The residue was partitioned between brine and ethyl acetate and the organics washed once more with brine, dried over Na₂SO₄, filtered, and the volatiles removed under reduced pressure. The product was purified by silica gel chromatography, eluting with a hexanes/DCM to DCM gradient, to produce 2-chloro-3-(difluoromethoxy)pyridine as a white solid (Compound 1006, 2.0 g, 72% yield): ESMS (M+H) 180; ¹H NMR (CDCl₃) δ 8.05 (m, 1H), 7.45 (m, 1H), 6.90 (m, 1H), 6.60 (t, 1H; J=75 Hz), 4.01 (s, 3H).

As shown in step 3-ii of Scheme 3, an excess of sodium metal was dissolved into 20 mL anhydrous methanol and 2-chloro-3-(difluoromethoxy)pyridine (2.0 g, 11.1 mmol) in anhydrous methanol was added. The reaction mixture was stirred in a sealed vessel at 100° C. for 6 hours. The volatiles were removed under reduced pressure and the residue was partitioned between EtOAc and brine. The brine was extracted with EtOAc and the combined organics were dried over Na₂SO₄, filtered, and the volatiles removed under reduced pressure. The product was purified by silica gel chromatography (DCM) to yield 3-(difluoromethoxy)-2-methoxypyridine as a colorless oil (Compound 1007, 1.1 g, 56% yield: ESMS (M+H) 176.

As shown in step 3-iii of Scheme 3,3-(difluoromethoxy)-2-methoxypyridine (270 mg, 1.54 mmol) was dissolved in 5 mL of DCM and BBr₃ (540 µL; 1275 mg; 4.10 mmol) in heptane was added. The reaction mixture was stirred for 10 minutes at RT under an atmosphere of nitrogen, brought to reflux, and then stirred an additional 4 hours. The mixture was cooled and water was added to quench the reaction. The pH Scheme 2

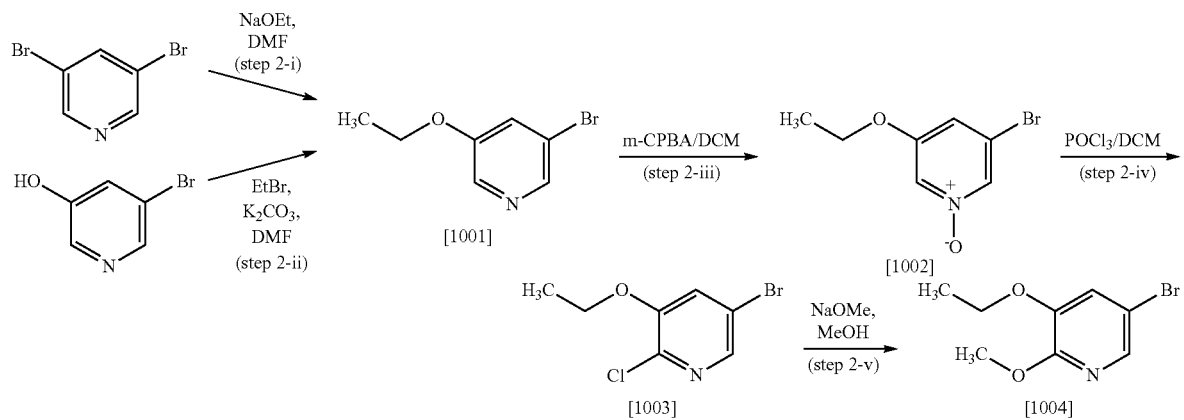

EXAMPLE 3

Preparation of
5-bromo-3-(difluoromethoxy)-2-methoxypyridine
(Compound 1010)

As shown in step 3-i of Scheme 3,2-chloro-3-hydroxypyridine (Compound 1005, 2.0 g, 15.4 mmol, obtained from Aldrich Chemical Co.) was dissolved in 40 mL of DMF and 5.0 mL of water along with sodium chlorodifluoroacetate was adjusted to 7-8 with sodium bicarbonate, the organics partitioned, and the aqueous layer saturated with NaCl and extracted twice more with DCM. The combined organics were dried over Na₂SO₄, filtered, and the volatiles removed under reduced pressure. The product was purified by silica gel chromatography (DCM to 5% MeOH/DCM gradient) to yield 3-(difluoromethoxy)pyridin-2-ol as a white solid (Compound 1008, 986 mg, 97% yield): ESMS (M+H) 162.

As shown in step 3-iv of Scheme 3,3-(difluoromethoxy) pyridin-2-ol (986 mg; 6.12 mmol) was dissolved in 25 mL of glacial acetic acid and sodium acetate (79 mg; 9.6 mmol) was added. The mixture was cooled in an ice bath and bromine (780 μL; 1.63 g; 10.22 mmol) in 10 mL of glacial acetic acid was added over 10 minutes. The reaction was stirred for 30 minutes at 10-15° C. The volatiles were removed under reduced pressure and the residue was partitioned between brine/saturated sodium carbonate solution and ethyl acetate. After the evolution of gas ceased, the organic and aqueous layers were separated and the aqueous solution extracted three additional times with EtOAc. The combined organics were dried over Na₂SO₄, filtered, and the volatiles removed under reduced pressure. The residue was purified twice by silica gel chromatography (first a DCM to 10% MeOH/DCM gradient then 1:1 EtOAc/hexanes) to provide 5-bromo-3-(difluoromethoxy)pyridin-2-ol as a light yellow powder (Compound 1009, 810 mg, 55% yield): ESMS (M+H) 241.9/243.9; ¹H NMR (CDCl₃) δ 13.2 (br m, 1H), 7.44 (d, 1H, J=2.1 Hz), 7.18 (d, 1H, J=2.1 Hz), 6.92 (t, 1H, J=75 Hz).

As shown in step 3-v of Scheme 3, 5-bromo-3-(difluoromethoxy)pyridin-2-ol (300 mg; 1.25 mmol) was dissolved in 5 mL of chloroform. Silver carbonate (690 mg; 2.5 mmol) and methyl iodide (780 μL; 1.77 g; 12.5 mmol) were added and the mixture stirred at RT overnight. The reaction mixture was filtered through diatomaceous earth, which was washed with additional CHCl₃. The filtrates were concentrated under reduced pressure to yield an oil which was purified by silica gel chromatography to yield 5-bromo-3-(difluoromethoxy)-2-methoxypyridine as a white solid (Compound 1010, 250 mg, 78% yield): ESMS (M+H) 254/256; ¹H NMR (CDCl₃) δ 8.08 (d, 1H, J=2.1 Hz), 7.56 (d, 1H, J=2.1 Hz), 6.60 (t, 1H, J=75 Hz), 3.98 (s, 3H).

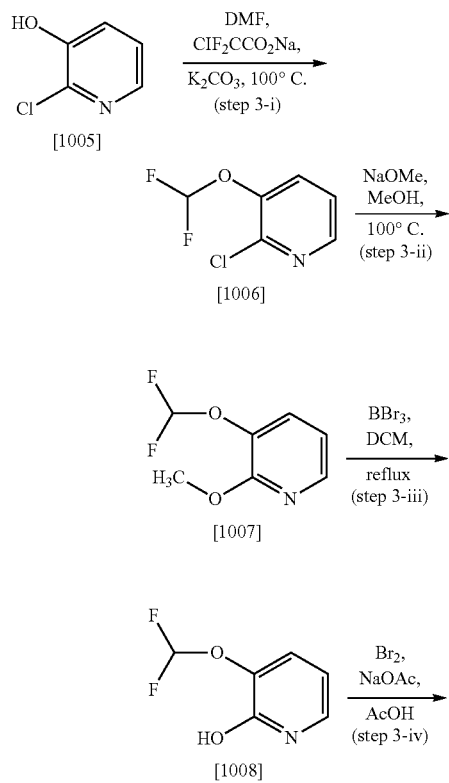

EXAMPLE 4

Preparation of 2,5-dibromo-3-ethoxypyridine (Compound 1015)

As shown in step 4-i of Scheme 4, 1,1'-carbonyldiimidazole (57.4 g, 354.2 mmol) was added to a solution of 2-amino-3-hydroxypyridine (26.0 g, 236.1 mmol, obtained from Aldrich Chemical Co.) in THF (400 mL). The resulting reaction mixture was stirred at 70° C. for 14 h. The reaction mixture was cooled to RT and concentrated under reduced pressure. The residue was dissolved in DCM (500 mL) and washed with 2 N NaOH (3×100 mL). The combined aqueous layers were cooled to 0° C. and acidified to a pH of 6 with 6 N HCl. The precipitate that was formed was collected in a fitted funnel, washed with cold water (100 mL), and dried under vacuum to afford oxazolo[4,5-b]pyridin-2(3H)-one (Compound 1011, 26.0 g, 81% yield): ESMS (M+H) 137; ¹H NMR (DMSO-d₆) δ 12.4 (br, 1H), 8.0 (d, 1H), 7.6 (d, 1H), 7.1 (dd, 1H).

As shown in step 4-ii of Scheme 4, bromine (10.8 mL, 210.1 mmol) was added dropwise over 20 min to a stirring solution of Compound 1011 (26.0 g, 191 mmol) in DMF (200 mL). The reaction mixture was stirred at RT for 14 h. The mixture was poured onto crushed ice and the precipitate that formed was collected in a fitted funnel. The solid was washed with water (200 mL) and dried under vacuum to afford 6-bromooxazolo[4,5-b]pyridine-2(3H)-one (Compound 1012, 37.0 g, 91% yield) as a light yellow solid: ESMS (M+H) 215, 217; ¹H NMR (DMSO-d₆) δ 12.6 (br, 1H), 8.2 (s, 1H), 8.0 (s, 1H).

As shown in step 4-iii of Scheme 20, Compound 1012 (34 g, 158.1 mmol) was diluted with 10% NaOH(aq) (500 mL), and the resulting mixture was stirred at 100° C. for 6 h. The reaction was cooled to 5° C., and 6 N HCl was added until a precipitate formed (ca. pH 10). The solid was collected in a fritted funnel, washed with water (200 mL), and dried under vacuum to afford 2-amino-5-bromo-3-hydroxypyridine (Compound 1013, 24.0 g, 80% yield) as a tan solid: ESMS (M+H) 189, 191; ¹H NMR (DMSO-d₆) δ 7.5 (s, 1H), 6.9 (s, 1H), 5.7 (br, 2H).

As shown in step 4-iv of Scheme 20, Compound 1013 (19.0 g, 100.5 mmol) was dissolved in DCM (90 mL), and iodoethane (9.0 mL, 110.6 mmol), Adogen® 464 (methyltrialkyl (C₈-C₁₀)ammonium chloride, 0.6 g), and 40% NaOH(aq) (90 mL) were added. The reaction was stirred at RT for 21 h. The DCM layer was separated, and the aqueous layer was diluted with water (100 mL) and extracted with DCM (2×100 mL). The combined organic extracts were dried over Na₂SO₄ and concentrated under reduced pressure. The crude product was purified on a silica plug eluting with 40% ethyl acetate/hexanes to afford 2-amino-5-bromo-3-ethoxypyridine (Compound 1014, 10.0 g, 46% yield) as a white solid: ESMS (M+H) 217, 219. $^1$H NMR (DMSO-$d_6$) δ 7.6 (s, 1H), 7.1 (s, 1H), 5.8 (br, 2H), 4.0 (q, 2H), 1.3 (t, 3H).

As shown in step 4-v of Scheme 4, Compound 1014 (10 g, 46.1 mmol) was diluted with 48% hydrobromic acid (90 mL, 530 mmol) and cooled to 0° C. Bromine (8.0 mL, 148 mmol) was added dropwise, followed by the addition of a 40 wt % solution of sodium nitrite (40.0 mL, 231 mmol). The dark black heterogeneous solution was stirred at 0° C. for 1 h. The reaction mixture was adjusted to a pH of 13 using 50% NaOH (aq), and the solids that formed were collected in a fritted funnel and washed with water (300 mL). The crude solid product was dissolved in DCM (500 mL), washed with 1 M $Na_2S_2O_3$ (50 mL) and brine (50 mL), dried over $Na_2SO_4$, and concentrated under reduced pressure to afford 2,5-dibromo-3-ethoxypyridine (Compound 1015, 10.0 g, 73% yield) as a light yellow solid: ESMS (M+H) 280, 282, 284; $^1$H NMR (DMSO-$d_6$) δ 8.1 (s, 1H), 7.8 (s, 1H), 4.2 (q, 2H), 1.4 (t, 3H).

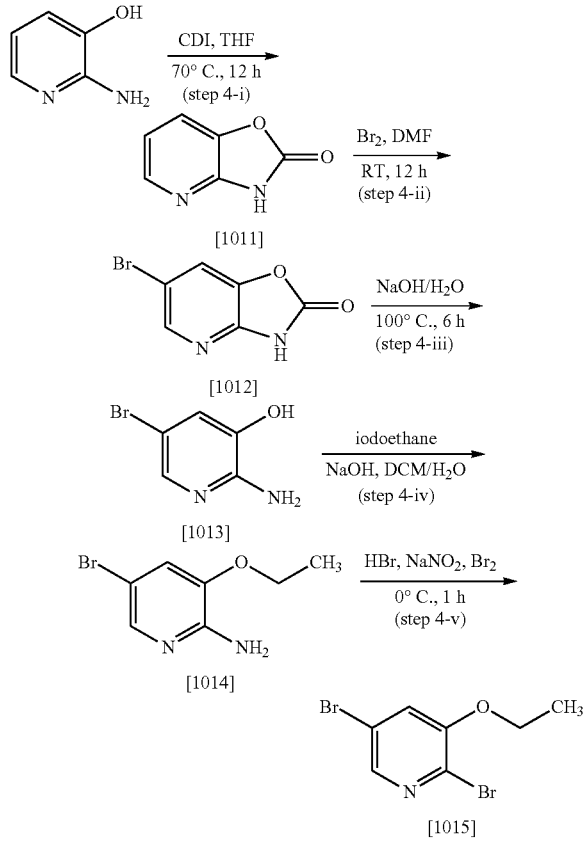

EXAMPLE 5

Preparation of 5-bromo-2-ethoxy-3-methoxypyridine (Compound 1016) and 5-bromo-2,3-dimethoxypyridine (Compound 1017)

As shown in step 5-i of Scheme 5, 5-bromo-2-chloro-3-methoxypyridine (1.0 g, 4.5 mmol, prepared in the same manner as Compound 1003 in Example 2 starting with 3-bromo-5-methoxypyridine) was treated with a sodium ethoxide/ethanol solution (5.05 mL, 21% w/v, 13.5 mmol) and the reaction mixture microwave irradiated at 100° C. for 20 minutes. Water was added and the ethanol evaporated under reduced pressure. The resulting aqueous solution was extracted with DCM and ether, followed by drying the combined extracts over MgSO4. After filtration, removal of the volatiles under reduced pressure provided 5-bromo-2-ethoxy-3-methoxypyridine (Compound 1016), 0.72 g, 69% yield): ESMS (M+H) 232.32/234.23. As shown in step 5-ii of Scheme 5, Compound 1017 (ESMS (M+H) 218.32/220.23) was prepared in the same manner as Compound 1016, using sodium methoxide in methanol instead of sodium ethoxide in ethanol.

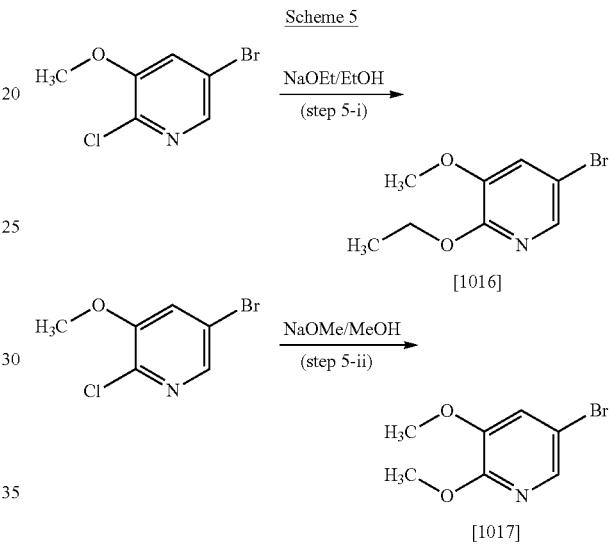

EXAMPLE 6

Preparation of 5-bromo-3-methoxy-2-methylpyridine (Compound 1021), 5-bromo-2-cyclopropyl-3-methoxypyridine (Compound 1022), and 5-bromo-2-isopropoxy-3-methoxypyridine (Compound 1023)

As shown in step 6-i of Scheme 6, calcium chloride (4.0 g, 35.7 mmol) was added to a stirring solution of 3-methoxy-2-nitropyridine (5.0 g, 32.5 mmol, obtained from AK Scientific, Inc.) in methanol (100 mL) and water (25 mL). The reaction mixture was warmed to 75° C. and iron powder (4.6 g, 81.1 mmol) was added carefully over 10 min. The resulting reaction mixture was stirred at 75° C. for another 2 h. The reaction mixture was cooled to RT and filtered through a pad of diatomaceous earth. The pad was rinsed with ethanol (400 mL) and the filtrate was evaporated under reduced pressure. The residue was suspended in ethyl acetate/water (1/1, 200 mL), the organic layer was separated, and the aqueous layer was extracted with ethyl acetate (3×100 mL). The combined organic extracts were washed with brine (60 mL), dried over $Na_2SO_4$, and concentrated under reduced pressure to afford 2-amino-3-methoxypyridine (Compound 1018, 3.6 g, 89% yield): ESMS (M+H) 125; $^1$H NMR (DMSO-$d_6$) δ 7.5 (d, 1H), 7.0 (d, 1H), 6.5 (dd, 1H), 5.6 (br, 2H), 3.75 (s, 3H).

As shown in step 6-ii of Scheme 6, bromine (6.3 mL, 120.8 mmol) was added dropwise to a stirring solution of Compound 1018 (15 g, 120.8 mmol) in acetic acid (150 mL) at RT.

The resulting reaction mixture was stirred at RT for 16 h. The reaction mixture was concentrated under reduced pressure, and the acetic acid was removed by azeotropic distillation with toluene (2×100 mL) under reduced pressure. The residue was cooled to 0° C. and neutralized with saturated sodium bicarbonate solution until a pH of 7 was achieved. The aqueous mixture was extracted with ethyl acetate (4×500 mL). The combined organic extracts were washed with brine (60 mL), dried over $Na_2SO_4$, and concentrated under reduced pressure. The residue was purified on a plug of silica, eluting with 50% ethyl acetate/hexanes to afford 2-amino-5-bromo-3-methoxypyridine (Compound 1019, 20.0 g, 81% yield): ESMS (M+H) 203, 205; $^1$H NMR (DMSO-$d_6$) δ 7.6 (s, 1H), 7.2 (s, 1H), 6.0 (br, 2H), 3.8 (s, 3H).

As shown in step 6-iii of Scheme 6, Compound 1019 (109.0 g, 536.8 mmol) was diluted with 48% hydrobromic acid (1.0 L, 6.2 mol), and the reaction mixture was cooled to 0° C. Bromine (89.0 mL, 1.72 mol) was added dropwise, followed by the addition of a 40 wt % solution of sodium nitrite (463.1 mL, 2.68 mol) over 40 min. The dark black heterogeneous mixture was stirred at 0° C. for 1 hour. The reaction mixture was adjusted to a pH of 13 with 50% NaOH (aq) and warmed to RT over 1 hour. Solids formed, which were collected on a fritted funnel and washed with water (3×1.0 L). The crude solid product was dissolved in DCM (2.0 L), washed with 1 M $Na_2S_2O_3$ (2×500 mL) and brine (500 mL), dried over $Na_2SO_4$, and concentrated under reduced pressure to afford 2,5-dibromo-3-methoxypyridine (Compound 1020, 126.0 g, 88% yield) as a light yellow solid: ESMS (M+H) 266, 268, 270; $^1$H NMR (DMSO-$d_6$) δ 8.1 (s, 1H), 7.8 (s, 1H), 3.9 (s, 3H).

As shown in step 6-iv of Scheme 6, Compound 1020 (5 g, 18.73 mmol) was dissolved in dry THF (94 mL) and Pd(PPh$_3$)$_4$ (2.16 g, 1.873 mmol) was added. The reaction mixture was cooled in an ice bath, and methylmagnesium bromide in 3/1 THF/toluene (17.4 mL, 1.4 M, 24.35 mmol) was slowly added. The ice bath was removed, and the reaction was heated to reflux. The reaction was stirred at reflux for 1 h and 3 mL of the methylmagnesium bromide solution were added. The reaction was stirred at reflux for another 20 min and 2 mL of the methylmagnesium bromide solution were added. The reaction was stirred at reflux for 1 h and cooled to RT. Ethyl ether and 1 N HCl were added, and the organic layer was separated and washed with 1 N HCl. The aqueous extracts were washed with ethyl ether three times. The aqueous layer was made basic with 2 N NaOH and extracted with ethyl acetate three times. The ethyl acetate extracts were combined and dried over $Na_2SO_4$, then concentrated under reduced pressure. The residue was purified via silica gel chromatography (0-25% ethyl acetate/hexanes) to afford 5-bromo-3-methoxy-2-methylpyridine (Compound 1021, 2.7 g, 71% yield): ESMS (M+H) 202, 204. 5-Bromo-2-ethyl-3-methoxypyridine was made by an analogous procedure: ESMS (M+H) 216, 218; 1H NMR (CDCl$_3$) δ 8.2 (d, 1H), 7.2 (d, 1H), 3.8 (s, 3H), 2.8 (q, 2H), 1.2 (t, 3H).

As shown in step 6-v of Scheme 6, Compound 1020 (3.6 g, 13.5 mmol), potassium cyclopropyl-trifluoro-boron (2.5 g, 16.9 mmol), and potassium phosphate (8.6 g, 40.5 mmol) were taken up in about 80 mL of a toluene/water mixture. The reaction mixture was flushed with nitrogen gas for 10 minutes and Pd(PPh$_3$)$_4$ (1.4 g, (1.21 mmol) was added. The reaction mixture was refluxed for 18 hours, resulting in a mixture of products by HPLC analysis. The reaction was cooled, diluted with EtOAc and saturated NaCl. The organics were separated, dried (MgSO$_4$), and concentrated under reduced pressure to provide a solid, which was purified by medium pressure silica gel chromatography (0-8% EtOAc/hexanes gradient) to give 5-bromo-2-cyclopropyl-3-methoxypyridine (Compound 1022, 0.54 g, 70% pure): ESMS (M+H) 227.9/229.9. This compound was used as is in subsequent reactions.

As shown in step 6-vi of Scheme 6, 2-propanol (287 μL, 3.75 mmol) in 1 mL DMF was added to a suspension of sodium hydride (187 mg/60% in mineral oil, 4.682 mmol) in 4 mL DMF at RT. The mixture was stirred for 30 minutes, then added to a stirring solution of 2,5-dibromo-3-methoxypyridine (500 mg, 1.873 mmol, Compound 1020) in 4 mL DMF at 60° C. The reaction was heated at 60° C. for 2 hours. After cooling to RT, water and ethyl acetate were added and the layers separated. The aqueous layer was extracted with ethyl acetate and the organics were combined, dried over MgSO$_4$, filtered, and concentrated under reduced pressure. The residue was adsorbed onto silica gel, which was eluted with ethyl acetate/hexanes (0-40%) to provide 5-bromo-2-isopropoxy-3-methoxypyridine (Compound 1023, 0.16 g, 35% yield): $^1$H NMR (CDCl$_3$) δ 7.77 (d, J=2.1 Hz, 1H), 7.13 (d, J=2.0 Hz, 1H), 5.35 (septet, J=6.2 Hz, 1H), 3.87 (s, 3H), 1.40 (d, J=6.2 Hz, 6H). 5-Bromo-3-methoxy-2-propoxypyridine and 5-bromo-2(2,2-difluoroethoxy)-3-methoxypyridine were prepared by an analogous procedure.

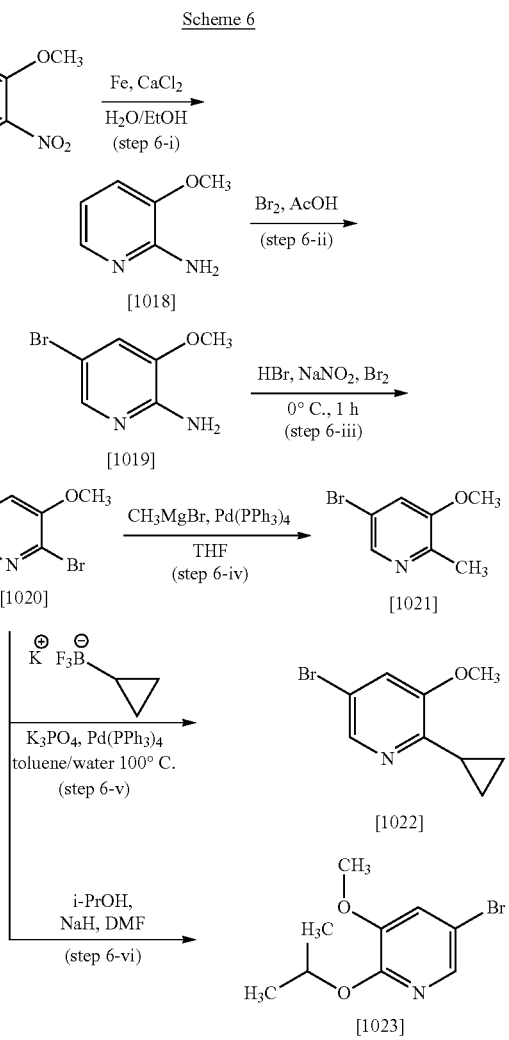

EXAMPLE 7

Preparation of 6-(5-methoxypyridin-3-yl)-N-(pyridin-3-yl)benzo[d]thiazol-2-amine (Compound 6)

As shown in step 7-i of Scheme 7,2,4-dibromo aniline (Aldrich Chemical Co. Cat. No. D3,840-5, 1.0 g; 4.0 mmols) and triethylamine (3.33 mL; 2.43 g; 24.0 mmols) was dissolved in 10 mL of dry p-dioxane under an atmosphere of nitrogen. The resulting solution was added dropwise over 10 minutes to a stirring solution of thiophosgene (920 μL; 1.38 g; 12.0 mmols) in 20 mL of dry p-dioxane. The reaction was stirred at RT for 1 hour under an atmosphere of nitrogen and then heated at 60° C. for 1 hour. The volatiles were removed under reduced pressure and the residue dissolved in a small amount of dioxane, which was also removed under reduced pressure. Dissolution in dioxane and solvent removal was repeated once more and the resulting 2,4-dibromo-1-isothiocyanatobenzene (Compound 1024) was dissolved in dry DMF and utilized as a stock solution for subsequent reactions.

As shown in step 7-ii of Scheme 7, to 2,4-dibromo-1-isothiocyanatobenzene (1.0 g; 3.43 mmol) in 10 mL of dry DMF was added 3-aminopyridine (321 mg; 3.40 mmol) in one portion. The reaction was stirred at RT for 12 hours in a sealed vessel. The reaction vessel was opened and purged with nitrogen gas for 3 minutes, followed by the addition of cesium carbonate (3.34 g; 6.80 mmol) and 10 mole % of tetrakistriphenylphosphine palladium (394 mg). The reaction vessel was sealed and heated for 5 minutes at 90° C. under microwave irradiation. After cooling, the mixture was filtered through a pad of diatomaceous earth and the volatiles removed under reduced pressure. The residue was triturated with diethyl ether to produce 6-bromo-N-(pyridin-3-yl)benzo[d]thiazol-2-amine (compound 1025, 98 mg, 76% yield), which was used in subsequent reactions without further purification: ESMS (M+H) 306, 308.

As shown in step 7-iii of Scheme 7,6-bromo-N-(pyridin-3-yl)benzo[d]thiazol-2-amine (200 mg, 0.65 mmol), 3-methoxy-5-(4,4,5,5-tetramethyl-1,3,2-dioxaborolan-2-yl)pyridine (230 mg; 0.98 mmols), and 1.0 mL of saturated sodium hydrogen carbonate solution were dissolved in 5 mL of DMA. The mixture was flushed with nitrogen gas 5 minutes, palladium dichloride (dppf) (10 mol %, 69 mg) was added, and the vial sealed. The mixture was heated under microwave irradiation at 100° C. for 10 minutes. After cooling, the solution was neutralizing with TFA and the solvent removed under reduced pressure. The resulting crude material purified via reversed phase HPCL using an acetonitrile/water gradient (containing 0.1% TFA). Fractions containing pure product were combined and lyophilized to provide 6-(5-methoxypyridin-3-yl)-N-(pyridin-3-yl)benzo[d]thiazol-2-amine (Compound 6, 33.2 mg, 60% yield) as a pale yellow powder: ESMS (M+H) 335.

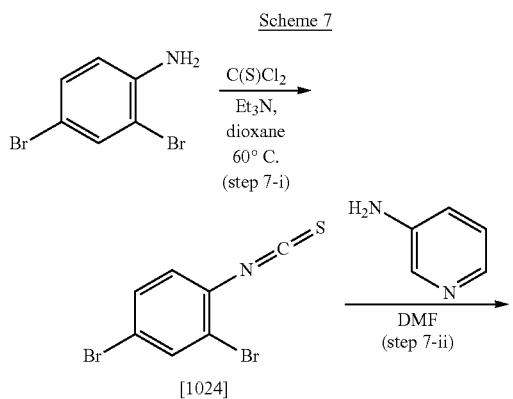

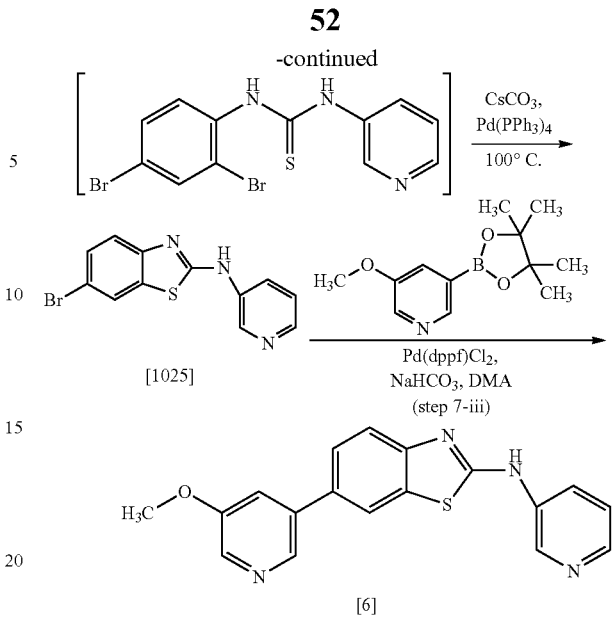

EXAMPLE 8

Preparation of 6-(5-methoxypyridin-3-yl)-N-(pyrazin-2-yl)benzo[d]thiazol-2-amine (Compound 1)

As shown in step 8-i of Scheme 8, N-(6-bromobenzo[d]thiazol-2-yl)acetamide [prepared from 2-amino-6-bromobenzthiazole (Aldrich Chemical Co.) and acetic anhydride, 1.5 g, 5.53 mmol] and 3-methoxy-5-(4,4,5,5-tetramethyl-1,3,2-dioxaborolan-2-yl)pyridine (1.95 g; 8.3 mmol) were dissolved in 45 mL of dry DMF and the mixture flushed with nitrogen gas for 10 minutes before the addition of PdCl$_2$(dppf) (400 mg; 055 mmol) and 16.6 mL of saturated sodium hydrogen carbonate solution (~3 equiv). The reaction was stirred under a nitrogen atmosphere at 110° C. for 1.0 hour. The reaction was cooled and the volatiles were removed under reduced pressure to yield a dark residue which was used in the next reaction as is.

As shown in step 8-ii of Scheme 8, the residue obtained from step 8-i was slurried in 50 mL of 2N HCl and heated to 60° C., resulting in the dissolution of most of the solid. The suspension was suctioned filtered through a hot pad of diatomaceous earth, which was washed with a small amount of warm 1N HCl. The filtrate was heated in an oil bath (100° C.) for 6.0 hours until complete hydrolysis of the acetyl was obtained (the repeated addition of small amounts of 12M HCl was required to drive the reaction to completion). The reaction mixture was cooled, suctioned filtered through a pad of diatomaceous earth, and the pH adjusted to 10, first with 50% NaOH and then sodium carbonate solution. A beige solid formed, which was filtered, washed with water, and dried under vacuum to provide 6-(5-methoxypyridin-3-yl)benzo[d]thiazol-2-amine (Compound 1026, 1.23 g. 86% yield): LCMS (M+H) 300.

As shown in step 8-iii of Scheme 8, of 6-(5-methoxypyridin-3-yl)benzo[d]thiazol-2-amine (250 mg; 0.97 mmol) was dissolved in 4.0 mL of dry DMA. Cesium carbonate (650 mg; 2.0 mmol] and 2-chloropyrazine (Aldrich Chemical Co. Cat. No. 13, 248-9, 250 mg; 2.35 mmol) were added and the mixture heated in a sealed tube under microwave irradiation at 200° C. for 15 minutes. After cooling, the volatiles were removed under reduced pressure and residue purified via reversed-phase HPLC using an acetonitrile/water gradient (0.1% TFA). Fractions containing pure product were combined and lyophilized to provide (Compound 1, 50 mg, 15% yield) as an off-white powder: LCMS (M+H) 336.

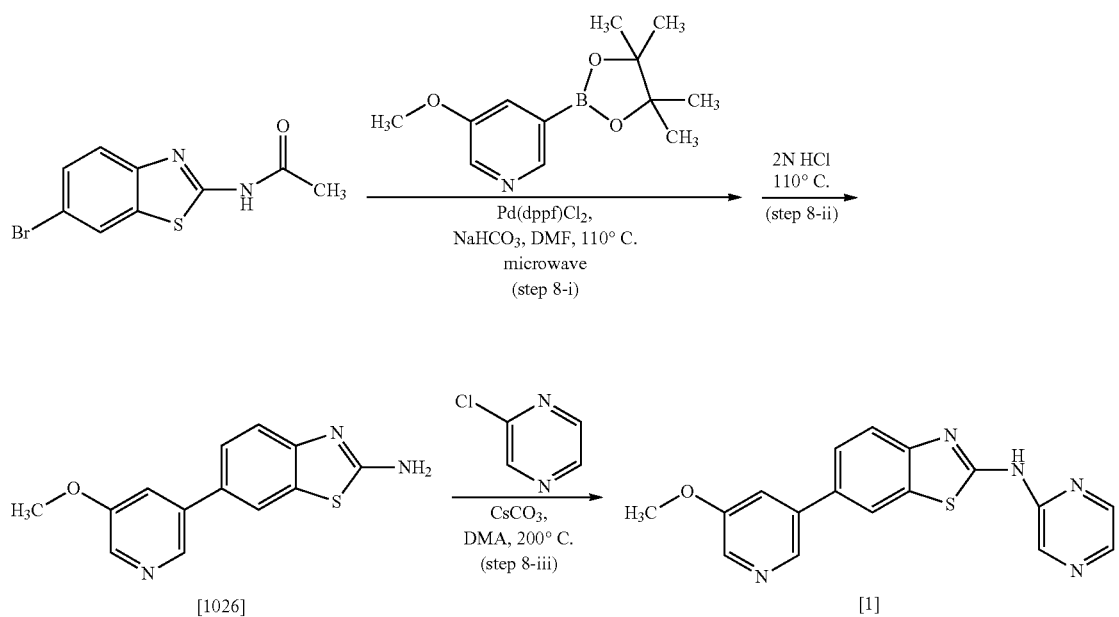

EXAMPLE 9

Preparation of 6-(5-methoxypyridin-3-yl)-N-(thiazol-2-yl)benzo[d]thiazol-2-amine (Compound 4)

As shown in step 9-i of Scheme 9, 6-bromo-2-chlorobenzo[d]thiazole (50 mg; 0.2 mmol), 2-aminothiazole (Acros Chemical Co., 50 mg; 0.45 mmol), and cesium carbonate (130 mg, 0.4 mmol) were dissolved in 1 mL of DMA. The reaction was heated under microwave irradiation at 110° C. for 10 minutes. After filtering the reaction mixture through a pad of diatomaceous earth, the volatiles were removed under reduced pressure and residue purified on silica gel, using ethyl acetate as the eluent. Fractions containing pure product were combined and the volatiles removed under reduced pressure. The resulting 6-bromo-N-(thiazol-2-yl)benzo[d]thiazol-2-amine (Compound 1027) was used as is in the next reaction.

Accordingly, as shown in step 9-ii of Scheme 9, 50 mg of Compound 1027 from step 9-i and 3-methoxy-5-(4,4,5,5-tetramethyl-1,3,2-dioxaborolan-2-yl)pyridine (53 mg, 0.4 mmol) were dissolved in 2.0 mL of DMA and 200 µL of saturated sodium hydrogen carbonate solution was added. The mixture was flushed with nitrogen gas for 3 minutes, and 10 mole % of $PdCl_2(dppf)$ (13 mg) was added. The reaction vessel was sealed and the mixture heated under microwave irradiation for 10 minutes at 110° C. After cooling, the volatiles were removed under reduced pressure and residue was purified by reversed-phase HPLC, eluting with an acetonitrile/water gradient (0.1% TFA). Fractions containing pure product were combined and lyophilized to provide 6-(5-methoxypyridin-3-yl)-N-(thiazol-2-yl)benzo[d]thiazol-2-amine (Compound 4, 12 mg, 40% yield) as a yellow powder: LCMS (M+H) 341.

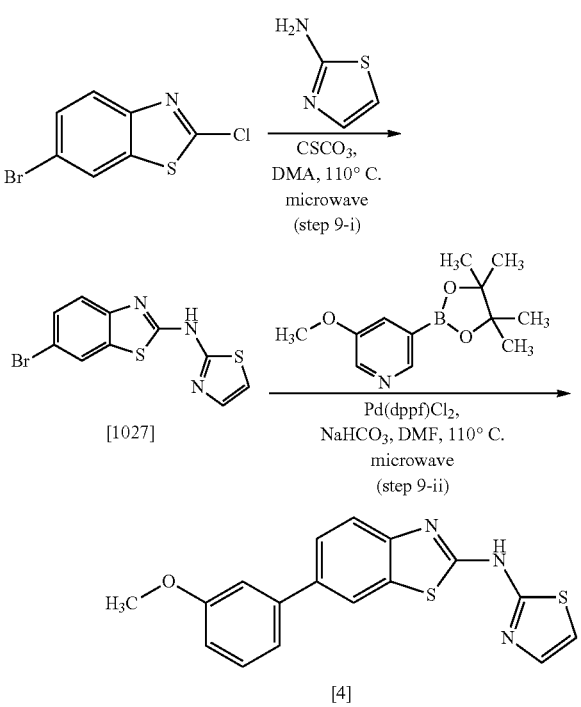

Table 2 provides analytical characterization data for certain compounds of formula I (blank cells indicate that the test was not performed). Compound numbers in Table 2 correspond to those depicted in Table 1.

TABLE 2

| Compound No. | ESMS (M + H) | ¹H NMR (300 MHz, unless indicated otherwise) NMR peaks given as δ values |
|---|---|---|
| 1 | 336.0 | (DMSO-d$_6$): 12.0(m, ex, 1H), 8.61(d, 1H), 8.55(d, 1H), 8.41(d, 1H), 8.39((d, 1H), 8.36(m, 1H), 8.28(d, 1H), 8.24(d, 1H). 7.78(m, 2H), 7.69(t, 1H). 3.94(s, 3H) |
| 2 | 350.0 | (DMSO-d$_6$): 8.67(d, 1H), 8.45(d, 1H), 8.41(s, 1H), 8.398(d, 1H), 8.15(s, 1H), 8.6(s, 1H), 7.92(dd, 1H), 7.83(d, 1H), 7.77(s, 1H), 3.98(s, 3HH), 2.54(s, 3H) |
| 3 | 355.0 | (CD$_3$CN-d$_3$): 8.57(d, 1H), 8.30(d, 1H), 8.09(d, 1H), 7.97(dd, 1H), 7.74(s, 1H), 7.69(d, 1H), 6.5(s, 1H), 3.93(s, 3H), 2.27(s, 3H) |
| 4 | 341.0 | (methanol-d$_4$): 8.86(d, 1H), 8.60(d, 1H). 8.50(m, 1H), 8.47(d, 1H), 8.04(dd, 1H), 7.84(d, 1H), 7.70(d, 1H), 7.30(d, 1H), 4.16(s, 3H) |
| 5 | 336.0 | (DMSO-d$_6$): 11.40 (br m, 1H) 9.11 (d, J = 2.3 Hz, 1H), 8.93 (d, J = 1.7 Hz, 1H), 8.45 (dt, J = 7.1, 2.1 Hz, 1H), 8.43 (s, 1H), 8.41 (d, J = 1.3 Hz, 1H), 8.39 (t, J = 1.4 Hz, 1H), 8.11 (d, J = 2.9 Hz, 1H), 8.09 (d, J = 8.5 Hz, 1H), 7.64 (dd, J = 5.0, 8.5 Hz, 1H), 3.97 (s, 3H) |
| 6 | 335.0 | (DMSO-d$_6$): 11.25 (br m, 1H), 9.23 (d, J = 2.4 Hz, 1H), 8.64 (d, J = 1.7 Hz, 1H), 8.44 (dd, J = 1.1, 5.1 Hz, 1H), 8.39 (d, J = 2.7 Hz, 1H), 8.37 (d, J = 1.4 Hz, 1H), 8.35(d, J = 1.7 Hz, 1H), 7.90-7.89 (m, 1H), 7.83 (d, J = 1.7 Hz, 1H), 7.75 (dd, J = 5.1, 8.5 Hz, 2H), 3.97 (s, 3H) |
| 7 | 382.0 | (DMSO-d$_6$): 8.63 (d, J = 1.7 Hz, 1H), 8.38 (d, J = 2.7 Hz, 1H), 8.35 (d, J = 1.6 Hz, 1H), 7.88 (t, J = 2.2 Hz, 1H), 7.83 (dd, J = 1.9, 8.5 Hz, 1H), 3.96 (s, 3H), 2.38 (m, 1H), 1.16-1.11 (m, 2H), 1.02-0.90 (m, 2H) |
| 8 | 342.0 | (DMSO-d$_6$): 9.07 (br. s, 1H), 8.62 (d, J = 1.5 Hz, 1H), 8.37 (s, 2H), 7.85-7.73 (m, 3H), 7.51 (m, ½H), 3.95 (d, J = 4.5 Hz, H), 2.09 (s, H) |
| 9 | 335.5 | |
| 10 | 366.0 | (DMSO-d$_6$): 11.98 (s, 1H), 8.62 (s, 1H), 8.39 (q, J = 1.4 Hz, 1H), 8.28 (s, 1H), 8.23 (d, J = 2.7 Hz, 1H), 8.05 (d, J = 2.0 Hz, 1H), 7.74 (s, 2H), 7.60 (d, J = 2.0 Hz, 1H), (d, J = 3.3 Hz, 6H) |
| 11 | 379.9 | |
| 12 | 380.2 | |
| 13 | 394.19 | |
| 14 | 324.00 | (CDCl$_3$, 400 MHz): 12.41 (s, exchanged with D2O, 1H), 10.95 (s, exchanged with D2O, 1H), 8.52 (s, 1H), 8.25-8.23 (m, 2H), 7.69-7.59 (series of m, 4H), 6.22 (s, 1H), 3.92 (s, 3H) |
| 15 | 338.00 | (CDCl$_3$, 400 MHz): 10.95 (s, exchanged with D2O, 1H), 8.52 (s, 1H), 8.25-8.23 (m, 2H), 7.69-7.59 (series of m, 4H), 6.22 (s, 1H), 3.91 (s, 3H), 3.88 (s, 3H) |
| 16 | 394.38 | (DMSO-d$_6$): 11.97 (s, 1H), 8.62 (s, 1H), 8.39 (q, J = 1.4 Hz, 1H), 8.26 (s, 1H), 8.23 (d, J = 2.7 Hz, 1H), 8.04 (d, J = 2.0 Hz, 1H), 7.72 (d, J = 1.4 Hz, 2H), 7.59 (d, J = 2.0 Hz, 1H), 4.79 (qn, J = 6.1 Hz, 1H), 3.90 (s, 3H), 1.32 (d, J = 6.0 Hz, 6H) |
| 17 | 351.38 | (DMSO-d$_6$): 11.93 (s, 1H), 8.61 (s, 1H), 8.38 (q, J = 1.4 Hz, 1H), 8.22 (d, J = 2.7 Hz, 1H), 8.19 (s, 1H), 7.90 (d, J = 1.9 Hz, 1H), 7.77-7.56 (m, 2H), 7.36 (d, J = 1.7 Hz, 1H), 5.78 (s, 2H), 3.89 (s, 3H) |
| 18 | 349.10 | (DMSO-d$_6$): 11.59 (br.s, exchanged with D2O, 1H), 8.55 (s, 1H), 8.35 (s, 1H), 8.26 (d, J = 3.6 Hz, 1H), 7.78-7.64 (m, 4H), 6.98 (d, J = 10.8 Hz, 1H), 6.90 (d, J = 9.6 Hz, 1H), 3.93 (s, 3H), 2.52 (s, 3H) |
| 19 | 379.20 | (DMSO-d$_6$): 11.53 (br.s, exchanged with D2O, 1H), 8.27 (s, 1H), 8.05 (s, 1H), 7.68-7.61 (m, 4H), 6.98 (d, J = 10.8 Hz, 1H), 6.89 (d, J = 9.6 Hz, 1H), 3.91 (s, 6H), 2.53 (s, 3H) |
| 20 | 354.10 | (DMSO-d$_6$): 12.43 (br.s, exchanged with D2O, 1H), 10.91 (br.s, exchanged with D2O, 1H), 8.14 (s, 1H), 8.01 (d, J = 2.4 Hz, 1H), 7.68-7.56 (m, 4H), 6.23 (s, 1H), 3.90 (s, 6H) |
| 21 | 368.10 | (DMSO-d$_6$): 10.9 (br.s, exchanged with D2O, 1H), 8.14 (s, 1H), 8.01 (s, 1H), 7.6-7.5 (m, 4H), 6.23 (s, 1H), 3.90 (s, 6H), 3.80 (s, 3H) |
| 22 | 410.20 | (DMSO-d$_6$): 11.94 (br.s, exchanged with D2O, 1H), 8.29 (s, 1H), 8.05 (d, J = 8.4 Hz, 2H), 7.84 (s, 1H), 7.72 (s, 2H), 7.61 (s, 1H), 4.63-4.56 (q, 2H), 3.91 (s, 6H), 1.48-1.44 (t, J = 6.9 Hz, 3H) |
| 23 | 396.30 | (DMSO-d$_6$): 10.89 (br.s, exchanged with D2O, 1H), 8.17 (d, J = 1.2 Hz, 1H), 8.02 (d, J = 1.8 Hz, 1H), 7.66-7.55 (series of m, 4H), 6.20 (d, J = 2.1 Hz, 1H), 4.02 (t, J = 6.6 Hz, 2H), 3.90(s, 3H), 3.89 (s, 3H), 1.88-1.76 (m, 2H), 0.89 (t, J = 7.5 Hz, 3H) |

TABLE 2-continued

| Compound No. | ESMS (M + H) | $^1$H NMR (300 MHz, unless indicated otherwise) NMR peaks given as δ values |
|---|---|---|
| 24 | 365.20 | (DMSO-$d_6$): 11.6 (br.s, exchanged with D2O, 1H), 8.37 (d, J = 4.2 Hz, 1H), 8.23 (s, 1H), 8.04 (d, J = 1.8 Hz, 1H), 7.80-7.52 (m, 1H), 7.68 (s, 2H), 7.59 (d, J = 2.1 Hz, 1H), 7.20 (d, J = 8.1 Hz, 1H), 7.04 (t, J = 5.7 Hz, 1H), 3.91 (s, 3H), 3.90 (s, 3H) |
| 25 | 366.20 | (DMSO-$d_6$): 12.04 (br.s, exchanged with D2O, 1H), 8.91 (s, 1H), 8.55 (d, J = 5.7 Hz, 1H), 8.30 (s, 1H), 8.05 (s, 1H), 7.76 (s, 2H), 7.60 (s, 1H), 7.23 (d, J = 5.4 Hz, 1H), 3.91 (s, 6H) |
| 26 | 396.20 | (DMSO-$d_6$): 11.97 (br.s, exchanged with D2O, 1H), 8.29 (s, 1H), 8.09 (d, J = 13.2 Hz, 2H), 7.87 (s, 1H), 7.73 (s, 2H), 7.62 (s, 1H), 4.14 (s, 3H), 3.91 (s, 6H) |
| 27 | 395.34 | (DMSO-$d_6$): d 11.15 (d, J = 0.8 Hz, 1H), 8.91 (d, J = 3.0 Hz, 1H), 8.81 (s, 1H), 8.71 (s, 0H) 1H impurity), 8.52-8.44 (m, 0H) 1H impurity), 8.40 (d, J = 3.0 Hz, 1H), 8.30 (d, J = 2.9 Hz, 0H) 1H impurity), 8.20-8.14 (m, 2H), 8.07 (s, 1H), 7.88 (d, J = 8.6 Hz, 1H), 7.79-7.74 (m, 0H) 1H impurity), 4.57 (q, J = 7.0 Hz, 2H), 4.08 (dd, J = 6.8, 13.8 Hz, 2H), 1.28 (dd, J = 2.3, 7.3 Hz, 6H) |
| 28 | 350.05 | (DMSO-$d_6$): d 12.08 (s, 1H), 8.62 (dd, J = 1.4, 7.9 Hz, 2H), 8.46 (d, J = 1.5 Hz, 1H), 8.41 (q, J = 1.4 Hz, 1H), 8.26 (d, J = 2.7 Hz, 1H), 8.10 (s, 1H), 7.90 (dd, J = 1.9, 8.5 Hz, 1H), 7.83-7.78 (m, 1H), 4.07 (s, 3H), 2.30 (s, 3H) |
| 29 | 365.25 | (DMSO-$d_6$): 9.34 (s, 1H), 8.56 (d, J = 8.4 Hz, 1H), 8.49 (d, J = 4.8 Hz, 1H), 8.27 (s, 1H), 8.05 (d, J = 2.0 Hz, 1H), 7.88 (dd, J = 5.4, 8.8 Hz, 1H), 7.76 (dd, J = 8.5, 10.9 Hz, 2H), 7.60 (d, J = 2.0 Hz, 1H), 3.91 (s, 3H), 3.90 (s, 3H) and 2.32 (s, 6H) |
| 30 | 385.20 | (DMSO-$d_6$): 12.27 (br.s, exchanged with D2O, 1H), 8.17 (s, 1H), 8.02 (d, J = 1.5 Hz, 1H), 7.70-7.57 (m, 4H), 7.10 (s, 1H), 3.91, 3.89 (2s, 6H) |
| 31 | 386.20 | (DMSO-$d_6$): 13.01 (br.s, exchanged with D2O, 1H), 8.21 (s, 1H), 8.03 (d, J = 1.8 Hz, 1H), 7.72-7.63 (m, 2H), 7.59-7.58 (d, J = 1.5 Hz, 1H), 3.91 (s, 6H), 2.61 (s, 3H) |
| 32 | 364.35 | (methanol-$d_4$): 8.58 (m, 2H), 8.40 (m, 1H), 8.36 (m, 1H), 8.23 (d, J = 3.0 Hz, 1H), 7.87 (m, 2H), 4.20 (s, 3H), 3.10 (q, J = 7.5 Hz, 2H), 2.70 (s, 3H, MsOH), 1.39 (t, J = 7.5 Hz, 3H) |
| 33 | 380.30 | (CDCl$_3$): 11.95 (br.s, exchanged with D2O, 1H), 8.55 (d, J = 5.1 Hz, 1H), 8.28 (s, 1H), 8.05 (s, 1H), 7.72 (s, 2H), 7.60 (s, 1H), 7.02 (d, J = 4.8 Hz, 1H), 3.91 (d, J = 2.4 Hz, 6H), 2.51 (s, 3H) |
| 34 | 380.30 | (DMSO-$d_6$): 11.93 (br.s, exchanged with D2O, 1H), 8.39 (s, 1H), 8.32 (s, 1H), 8.13 (s, 1H), 8.06 (d, J = 1.8 Hz, 1H), 7.73 (s, 2H), 7.61 (s, 1H), 3.91, 3.90 (2s, 6H), 2.50 (s, 3H) |
| 35 | 395.20 | (DMSO-$d_6$): 11.57 (br.s, exchanged with D2O, 1H), 8.26 (s, 1H), 8.04 (d, J = 1.2 Hz, 1H), 7.69-7.61 (m, 4H), 6.69 (d, J = 7.5 Hz, 1H), 6.40 (d, J = 8.1 Hz, 1H), 4.10 (s, 3H), 3.90 (s, 6H) |
| 36 | 366.20 | (DMSO-$d_6$): 12.02 (s, exchanged with D2O, 1H), 8.71 (d, J = 4.8 Hz, 2H), 8.27 (s, 1H), 8.04 (s, 1H), 7.72 (s, 2H), 7.59 (s, 1H), 7.14 (t, J = 5.6 Hz, 1H), 3.91 (s, 3H), 3.90 (s, 3H) |
| 37 | 367.00 | (DMSO-$d_6$): 12.10 (s, exchanged with D2O, 1H), 8.64 (s, 1H), 8.44-8.41 (d, J = 9.3 Hz, 2H), 8.27 (s, 1H), 8.06 (s, 2H), 7.94 (s, 1H), 3.93, 3.92 (2 s, 6H) |
| 38 | 381.10 | (DMSO-$d_6$): 12.11 (s, exchanged with D2O, 1H), 8.64 (s, 1H), 8.43 (d, J = 1.5 Hz, 2H), 8.28 (d, J = 2.7 Hz, 1H), 8.06 (s, 2H), 7.93 (s, 1H), 4.43-4.36 (m, 2H), 3.91 (s, 3H), 1.38-1.33 (t, J = 7.2 Hz, 3H) |
| 39 | 395.10 | (DMSO-$d_6$): 12.10 (s, exchanged with D2O, 2H), 8.64 (s, 1H), 8.44 (d, J = 7.5 Hz, 2H), 8.28 (d, J = 2.4 Hz, 1H), 8.05 (s, 2H), 7.94 (s, 1H), 4.78 (m, 1H), 3.92 (s, 3H), 1.33-1.31(d, J = 6.0 Hz, 6H) |
| 40 | 366.10 | (DMSO-$d_6$): 10.96 (s, exchanged with D2O, 1H), 8.92-8.91 (d, J = 2.1 Hz, 1H), 8.41-8.27 (m, 3H), 8.01 (s, 2H), 7.90 (s, 1H), 7.45-7.41 (m, 1H), 3.93-3.91 (2s, 6H) |
| 41 | 380.2 | (DMSO-$d_6$): 10.98 (s, exchanged with D2O, 1H), 8.94 (s, 1H), 8.41-8.30 (m, 3H), 8.03 (s, 2H), 7.92 (s, 1H), 7.48-7.43 (m, 1H), 4.42 (d, J = 6.9 Hz, 2H), 3.93 (s, 3H), 3.16 (t, J = 7.2 Hz, 3H) |
| 42 | 394.2 | (DMSO-$d_6$): 10.95 (s, exchanged with D2O, 1H), 8.92-8.91 (d, J = 2.1 Hz, 1H), 8.39-8.27 (m, 3H), 7.99 (s, 2H), 7.88 (s, 1H), 7.45-7.41 (m, 1H), 4.43-4.36 (m, 2H), 4.18-4.16 (m, 2H), 1.41-1.33 (m, 6H) |

TABLE 2-continued

| Compound No. | ESMS (M + H) | ¹H NMR (300 MHz, unless indicated otherwise) NMR peaks given as δ values |
|---|---|---|
| 43 | 394.2 | (DMSO-$d_6$): 10.95 (s, exchanged with D2O, 1H), 8.92-8.91 (d, J = 2.7 Hz, 1H), 8.41-8.27 (m, 3H), 8.00 (s, 2H), 7.90-7.89 (d, J = 1.8 Hz, 1H), 7.45-7.41 (m, 1H), 4.79-4.75 (m, 1H), 3.92 (s, 3H), 1.33-1.30 (m, 6H) |
| 44 | 374.00 | (DMSO-$d_6$): 11.11 (exchanged by D2O, 1H), 9.57 (s, 1H), 8.99 (s, 1H), 8.93 (d, J = 2.4 Hz, 1H), 8.77 (s, 1H), 8.34-8.23 (m, 2H), 8.09 (J = 8.4 Hz, 1H), 7.45-7.41 (m, 2H) |
| 45 | 334.05 | (DMSO-$d_6$): 10.82 (s, 1H), 8.82 (s, 1H), 8.56 (s, 1H), 8.40 (s, 1H), 8.28 (s, 1H), 7.83 (d, J = 7.7 Hz, 2H), 7.75 (d, J = 7.8 Hz, 1H), 7.39 (s, 2H), 7.06 (s, 1H) and 4.05 (s, 3H) ppm |
| 46 | 390.29 | |
| 47 | 376.28 | (DMSO-$d_6$): 10.67 (s, 1H), 8.78 (s, 1H), 8.52 (s, 1H), 8.36 (s, 1H), 8.20 (s, 1H), 7.84 (d, J = 5.6 Hz, 1H), 7.71 (d, J = 7.2 Hz, 3H), 7.26 (d, J = 7.1 Hz, 2H), 4.03 (s, 3H), 2.89 (d, J = 4.8 Hz, 1H) and 1.21 (d, J = 6.2 Hz, 6H) ppm |
| 48 | 392.10 | (DMSO-$d_6$): 10.45 (s, 1H), 8.66 (s, 1H), 8.41 (d, J = 2.5 Hz, 1H), 8.29 (d, J = 1.7 Hz, 1H), 7.96 (s, 1H), 7.79 (dd, J = 8.5, 10.4 Hz, 1H), 7.66 (t, J = 4.2 Hz, 3H), 6.95 (d, J = 9.0 Hz, 2H), 4.57 (qn, J = 6.0 Hz, 1H), 3.98 (s, 3H) and 1.27 (d, J = 6.0 Hz, 6H) ppm |
| 49 | 352.10 | (DMSO-$d_6$): 10.67 (s, 1H), 8.65 (d, J = 1.6 Hz, 1H), 8.39 (d, J = 2.6 Hz, 1H), 8.31 (d, J = 1.8 Hz, 1H), 7.92 (d, J = 1.9 Hz, 1H), 7.85-7.77 (m, 3H), 7.71 (d, J = 8.4 Hz, 1H), 7.24 (dd, J = 2.2, 15.6 Hz, 2H), 3.97 (s, 3H), 2.73 (s, H), 2.54 (s, H), 2.50 (qn, J = 1.8 Hz, H), 2.27 (d, J = 2.0 Hz, H), 0.20 (s, H), −0.00 (TMS) and −0.20 (s, H) ppm |
| 50 | 414.20 | (DMSO-$d_6$): 10.81 (s, 1H), 8.65 (d, J = 1.6 Hz, 1H), 8.38 (d, J = 2.7 Hz, 1H), 8.33 (d, J = 1.7 Hz, 1H), 8.05 (s, 1H), 7.91 (s, 1H), 7.86-7.72 (m, 3H), 7.58-7.45 (m, 2H), 7.27-7.20 (m, 1H), 6.45 (s, 1H), 3.95 (s, 3H) and 3.93 (s, 3H) ppm |
| 51 | 376.10 | |
| 52 | 401.30 | |
| 53 | 359.10 | |
| 54 | 390.10 | (DMSO-$d_6$): 10.59 (s, 1H), 8.66 (s, 1H), 8.40 (d, J = 2.5 Hz, 1H), 8.31 (d, J = 1.6 Hz, 1H), 7.94 (s, 1H), 7.80-7.75 (m, 2H), 7.69 (d, J = 8.0 Hz, 1H), 7.32 (t, J = 7.9 Hz, 2H), 7.10 (d, J = 7.7 Hz, 1H), 3.98 (s, 3H) and 1.30 (s, 9H) ppm |
| 55 | 391.20 | |
| 56 | 362.10 | (DMSO-$d_6$): 10.48 (s, 1H), 8.65 (d, J = 1.7 Hz, 1H), 8.39 (d, J = 2.7 Hz, 1H), 8.30 (d, J = 1.7 Hz, 1H), 7.94 (d, J = 2.0 Hz, 1H), 7.78-7.71 (m, 2H), 7.40 (s, 2H), 6.71 (s, 1H), 3.97 (s, 3H) and 2.28 (s, 6H) ppm |
| 57 | 394.10 | (DMSO-$d_6$): 10.60 (s, 1H), 8.64 (d, J = 1.6 Hz, 1H), 8.38 (d, J = 2.6 Hz, 1H), 8.31 (d, J = 1.7 Hz, 1H), 7.91 (s, 1H), 7.81-7.71 (m, 2H), 7.03 (d, J = 2.2 Hz, 1H), 6.24 (t, J = 2.2 Hz, 1H), 3.97 (s, 3H) and 3.77 (s, 6H) ppm |
| 58 | 426.20 | (DMSO-$d_6$): 10.73 (s, 1H), 8.64 (d, J = 1.7 Hz, 1H), 8.39 (d, J = 2.6 Hz, 1H), 8.31 (d, J = 1.7 Hz, 1H), 7.92 (s, 1H), 7.78 (dd, J = 1.9, 8.4 Hz, 1H), 7.63 (dd, J = 8.6, 14.2 Hz, 2H), 7.50-7.34 (m, 4H), 7.20 (t, J = 7.4 Hz, 1H), 7.10 (dd, J = 1.1, 7.6 Hz, 2H), 6.67 (dd, J = 1.5, 8.0 Hz, 1H) and 3.97 (s, 3H) ppm |
| 59 | 400.10 | |
| 60 | 378.10 | (DMSO-$d_6$): 10.61 (s, 1H), 8.64 (d, J = 1.7 Hz, 1H), 8.38 (d, J = 2.6 Hz, 1H), 8.31 (d, J = 1.7 Hz, 1H), 7.90 (s, 1H), 7.81-7.71 (m, 2H), 7.52 (s, 1H), 7.30-7.26 (m, 2H), 6.66-6.61 (m, 1H), 4.05 (q, J = 7.0 Hz, 2H), 3.97 (s, 3H) and 1.36 (t, J = 6.9 Hz, 3H) ppm |
| 61 | 401.30 | |
| 62 | 420.00 | |
| 63 | 433.10 | |
| 64 | 495.10 | |
| 65 | 377.10 | |
| 66 | 348.20 | (DMSO-$d_6$): 10.50 (s, 1H), 8.55 (d, J = 1.7 Hz, 1H), 8.29-8.25 (m, 2H), 7.75-7.66 (m, 4H), 7.19 (m, 3H), 3.93 (s, 3H), 2.54 (s, H), 2.50 (qn, J = 1.7 Hz, H) and 2.29 (s, 3H) ppm |
| 67 | 392.10 | |
| 68 | 405.10 | |
| 69 | 390.10 | |
| 70 | 405.10 | |

TABLE 2-continued

| Compound No. | ESMS (M + H) | ¹H NMR (300 MHz, unless indicated otherwise) NMR peaks given as δ values |
|---|---|---|
| 71 | 405.10 | |
| 72 | 391.50 | |
| 73 | 364.10 | |
| 74 | 432.00 | |
| 75 | 419.10 | (DMSO-$d_6$): 10.35 (s, 1H), 8.53-8.49 (m, 1H), 8.26-8.21 (m, 2H), 7.74-7.61 (m, 5H), 6.99 (d, J = 9.1 Hz, 2H), 3.92 (s, 3H), 3.77-3.74 (m, 4H) and 3.07 (m, 4H) ppm |
| 76 | 401.00 | |
| 77 | 433.10 | |
| 78 | 424.10 | |
| 79 | 412.00 | |
| 80 | 469.00 | |
| 81 | 350.20 | |
| 82 | 335.90 | |
| 83 | 382.50 | (DMSO-$d_6$): 10.16 (d, J = 5.8 Hz, 1H), 8.65 (d, J = 1.5 Hz, 1H), 8.39 (d, J = 2.6 Hz, 1H), 8.28 (d, J = 1.8 Hz, 1H), 8.11 (t, J = 9.2 Hz, 1H), 7.94 (s, 1H), 7.76 (dd, J = 1.8, 8.5 Hz, 1H), 7.63 (d, J = 8.4 Hz, 1H), 6.99 (dd, J = 2.7, 12.8 Hz, 1H), 6.88-6.84 (m, 1H), 3.97 (s, 3H) and 3.77 (s, 3H) ppm |
| 84 | 391.70 | (DMSO-$d_6$): d 10.41 (s, 1H), 8.63 (d, J = 1.7 Hz, 1H), 8.37 (d, J = 2.7 Hz, 1H), 8.26 (d, J = 1.7 Hz, 1H), 7.90-7.84 (m, 1H), 7.77-7.64 (m, 4H), 6.96 (dd, J = 2.2, 6.9 Hz, 2H), 4.01-3.90 (m, 5H), 1.73 (td, J = 13.9, 7.1 Hz, 2H), 1.02 (dd, J = 7.3, 13.1 Hz, 3H) |
| 85 | 391.90 | |
| 86 | 372.90 | |
| 87 | 378.00 | |
| 88 | 390.60 | (DMSO-$d_6$): 10.52 (s, 1H), 9.92 (s, 1H), 8.54 (s, 1H), 8.28-8.24 (m, 1H), 7.75-7.65 (m, 4H), 7.57 (d, J = 9.0 Hz, 1H), 7.26 (s, 1H), 7.10 (d, J = 6.5 Hz, 1H), 6.92 (s, 1H), 3.92 (s, 3H) and 2.03 (s, 3H) ppm |
| 89 | 349.10 | (DMSO-$d_6$): 10.64 (s, 1H), 8.55 (d, J = 1.4 Hz, 1H), 8.29-8.27 (m, 2H), 7.80-7.66 (m, 4H), 7.19 (d, J = 8.7 Hz, 2H), 3.93 (s, 3H) and −0.20 (s, H) ppm |
| 90 | 350.10 | |
| 91 | 364.00 | |
| 92 | 378.60 | |
| 93 | 364.00 | |
| 94 | 417.70 | |
| 95 | 391.70 | (DMSO-$d_6$): 10.45 (s, 1H), 8.65 (d, J = 1.7 Hz, 1H), 8.40 (d, J = 2.6 Hz, 1H), 8.29 (d, J = 1.7 Hz, 1H), 7.94 (s, 1H), 7.79-7.66 (m, 2H), 7.53-7.49 (m, 1H), 7.11 (dd, J = 2.6, 8.7 Hz, 1H), 6.92-6.85 (m, 1H), 4.24 (dd, J = 5.0, 9.3 Hz, 4H) and 3.97 (s, 3H) ppm |
| 96 | 374.70 | |
| 97 | 378.50 | |
| 98 | 373.40 | |
| 99 | 374.50 | |
| 100 | 374.40 | |
| 101 | 372.70 | |
| 102 | 374.18 | (DMSO-$d_6$): 9.29 (d, J = 1.9 Hz, 1H), 9.05 (s, 1H), 8.97 (s, 1H), 8.61-8.55 (m, 3H), 7.95 (dd, J = 1.8, 8.5 Hz, 1H), 7.87 (d, J = 8.5 Hz, 1H), 7.29 (d, J = 5.8 Hz, 1H), 2.29 (s, 6H) |
| 103 | 388.23 | (DMSO-$d_6$): 9.29 (s, 1H), 8.96 (s, 1H), 8.54-8.53 (m, 2H), 7.92 (dd, J = 1.9, 8.4 Hz, 1H), 7.85-7.69 (m, 2H), 7.56 (d, J = 9.0 Hz, 1H), 2.61 (s, 3H), 2.29 (s, 6H) |
| 104 | 370.21 | (CDCl$_3$): 8.42(d, 1H), 8.3(d, 1H), 8.15(d, 1H), 7.7(d, 1H), 7.5(d, 1H), 7.4(dd, 2H), 7.3(m, 1H), 3.9(s, 3H) |
| 105 | 373.21 | (DMSO-$d_6$): 12.20 (d, J = 12.4 Hz, 1H), 9.29 (s, 1H), 8.99 (s, 1H), 8.71 (d, J = 7.2 Hz, 2H), 8.55 (d, J = 7.3 Hz, 2H), 8.23 (d, J = 6.2 Hz, 2H), 8.02-7.95 (m, 2H), 2.31 (s, 3H) |
| 106 | 373.32 | (DMSO-$d_6$): 11.39 (s, 1H), 9.33 (s, 1H), 9.27 (s, 1H), 8.96 (s, 1H), 8.58-8.46 (m, 4H), 7.93-7.77 (m, 3H), 2.32 (s, 4H) |
| 107 | 376.17 | (DMSO-$d_6$): 10.35 (s, 1H), 9.23 (s, 1H), 8.92 (s, 1H), 8.47 (s, 1H), 8.31 (d, J = 1.6 Hz, 1H), 8.05 (s, 1H), 7.81-7.78 (m, 1H), 7.62 (d, J = 8.4 Hz, 1H), 7.53 (s, 1H), 3.86 (s, 3H), 2.32 (s, 4H) |

TABLE 2-continued

| Compound No. | ESMS (M + H) | $^1$H NMR (300 MHz, unless indicated otherwise) NMR peaks given as δ values |
|---|---|---|
| 108 | 458.16 | (DMSO-$d_6$): 9.25 (s, 1H), 8.96 (d, J = 12.4 Hz, 1H), 8.66 (s, 1H), 8.49 (s, 1H), 8.37 (d, J = 1.8 Hz, 1H), 8.04 (dd, J = 2.6, 9.4 Hz, 1H), 7.83 (d, J = 8.4 Hz, 1H), 7.68 (d, J = 8.5 Hz, 1H), 7.18-7.12 (m, 1H), 3.74 (d, J = 4.8 Hz, 4H), 3.49 (d, J = 4.1 Hz, 4H), 2.29 (s, 9H) and 0.00 (s, H) |
| 109 | 388.12 | (DMSO-$d_6$): 10.15 (s, 1H), 9.23 (s, 1H), 8.91 (s, 1H), 8.47 (s, 1H), 8.28 (d, J = 12.2 Hz, 1H), 8.22 (d, 1H), 7.77 (t, 2H), 7.61 (d, 1H), 6.51 (d, J = 9.5 Hz, 1H) and 5.80 (s, 2H) |
| 110 | 434.23 | (DMSO-$d_6$): 8.68 (s, 1H), 8.47-8.38 (m, 2H), 7.97 (s, 1H), 7.90-7.82 (m, 2H), 7.74 (d, J = 8.4 Hz, 1H), 7.27 (d, J = 8.2 Hz, 1H), 7.07-6.98 (m, 1H), 3.96 (s, 3H), 3.51 (t, J = 7.1 Hz, 2H), 3.31-3.26 (m, 2H), 2.34 (s, 3H), 1.24 (t, J = 6.9 Hz, 3H), 1.08-1.04 (m, 3H) |
| 111 | 376.15 | (DMSO-$d_6$): 9.23 (s, 1H), 8.98 (s, 1H), 8.48 (s, 1H), 8.33 (s, 1H), 7.90-7.55 (m, 3H), 7.46 (d, J = 1.9 Hz, 1H), 6.37 (d, J = 12.5 Hz, 1H), 3.74 (d, J = 6.7 Hz, 3H), 2.35 (s, 6H) |
| 112 | 390.32 | (DMSO-$d_6$): 9.26 (s, 1H), 8.95 (s, 1H), 8.51 (s, 1H), 8.41 (d, J = 1.7 Hz, 1H), 7.99 (d, J = 4.9 Hz, 2H), 7.80-7.10 (m, 5H), 6.22 (d, J = 2.0 Hz, 1H), 4.10 (q, J = 7.2 Hz, 2H) and 1.41 (t, J = 7.2 Hz, 3H) |
| 113 | 433.35 | (DMSO-$d_6$): 9.24 (d, J = 1.6 Hz, 1H), 8.94 (s, 1H), 8.50 (s, 1H), 8.31 (d, J = 1.7 Hz, 1H), 8.13 (s, 1H), 7.82 (dd, J = 1.9, 8.5 Hz, 1H), 7.68-7.61 (m, 2H), 4.80 (s, 2H) and 2.64 (s, 3H) |
| 114 | 420.33 | (DMSO-$d_6$): 10.50 (m, 1H), 9.25 (s, 1H), 8.94 (s, 1H), 8.48 (s, 1H), 8.31 (s, 1H), 8.07 (s, 1H), 7.80 (d, J = 8.0 Hz, 1H), 7.64-7.58 (m, 2H), 4.27 (t, J = 5.0 Hz, 2H), 3.70 (t, J = 4.9 Hz, 2H) and 3.25 (s, 3H) ppm |
| 115 | 420.12 | (DMSO-$d_6$): 14.05 (m, 1h), 11.00 (m, 1H), 9.24 (d, J = 11.3 Hz, 1H), 8.94 (s, 1H), 8.54 (s, 1H), 8.38 (s, 1H), 7.82 (d, J = 8.2 Hz, 1H), 7.71-7.64 (m, 3H), 6.30 (d, J = 2.0 Hz, 1H) and 4.90 (m, 2H) |
| 116 | 446.10 | (DMSO-$d_6$): 10.50 (m, 1H), 9.24 (s, 1H), 8.93 (s, 1H), 8.48 (s, 1H), 8.31 (d, J = 1.7 Hz, 1H), 8.06 (s, 1H), 7.80 (dd, J = 1.9, 8.4 Hz, 1H), 7.64-7.57 (m, 2H), 4.21-4.12 (m, 3H), 3.76 (t, J = 6.6 Hz, 1H), 3.65 (dd, J = 6.9, 14.6 Hz, 1H), 1.94-1.90 (m, 1H), 1.85-1.70 (m, 2H) and 1.63-1.60(m, 1H) |

Biological Assay of Compounds of the Invention

EXAMPLE 10

PI3K Inhibition Assay

Using a Biomek FX from Beckman Coulter, 1.5 μL of each of ten 2.5-fold serial dilutions of a compound of the invention in 100% DMSO was added to an individual well (hereafter, "test well") in a 96 well polystyrene plate [Corning, Costar Item No. 3697]. One test well also contained 1.5 μL of DMSO with no compound. Another well contained an inhibitor in DMSO at a concentration known to completely inhibit the enzyme, (hereafter "background well"). Using a Titertek Multidrop, 50 μL of Reaction Mix [100 mM HEPES pH 7.5, 50 mM NaCl, 10 mM DTT, 0.2 mg/mL BSA, 60 μM phosphatidylinositol(4,5)-bisphosphate diC16 (PI(4,5)$P_2$; Avanti Polar Lipids, Cat. No. 840046P) and PI3K isoform of interest (see Table 3 for isoform concentrations)] was added to each well. To initiate the reaction, 50 μL of ATP Mix [20 mM $MgCl_2$, 6 μM ATP (100 μCi/μmole $^{33}$P-ATP)] was added each well, followed by incubating the wells for 30 min. at 25° C. Final concentrations in each well were 50 mM HEPES 7.5, 10 mM $MgCl_2$, 25 mM NaCl, 5 mM DTT, 0.1 mg/mL BSA, 30 μM PI(4,5)$P_2$, 3 μM ATP, and the PI3K isoform of interest (see Table 3). Final compound concentrations in each well ranged from 10 μM to 1 nM.

TABLE 3

| PI3K Isoform Concentrations | PI3K-α | PI3K-β | PI3K-γ | PI3K-δ |
|---|---|---|---|---|
| Enzyme concentration in Reaction Mix | 4 nM | 20 nM | 4 nM | 4 nM |
| Final enzyme concentration | 2 nM | 10 nM | 2 nM | 2 nM |

After incubation, the reactions in each well were quenched by addition of 50 μL of stop solution [30% TCA/Water, 10 mM ATP]. Each quenched reaction mixture was then transferred to a 96 well glass fiber filter plate [Corning, Costar Item No. 3511]. The plate was vacuum-filtered and washed three times with 150 μL of 5% TCA/water in a modified Bio-Tek Instruments ELX-405 Auto Plate Washer. 50 μL of scintillation fluid was added to each well and the plate read on a Perkin-Elmer TopCount™ NXT liquid scintillation counter to obtain $^{33}$P-counts representing inhibition values.

The value for the background well was subtracted from the value obtained for each test well and the data were fit to the competitive tight binding Ki equation described by Morrison and Stone, *Comments Mol. Cell. Biophys.* 2: 347-368, 1985.

Each of compounds 1 to 116 has a $K_i$ of less than 1.5 micromolar for PI3Kγ. Each of compounds 1-6, 8-44, 55, 63, 70-72, 79-82, 89, 94, 96, 102-104, 107, 109-110, and 113-116 has a $K_i$ of less than 0.1 micromolar for PI3Kγ. In one example, compound 110 has a $K_i$ of 0.003 micromolar.

Each of compounds 1-43, 45-47, 49-52, 55, 57, 60, 63-65, 70-73, 75, 77, 79-83, and 85-116 has a $K_i$ of less than 1.5 micromolar for PI3Kα. Each of compounds 1, 2, 4, 10-17, 19-31, 33-41, 43, 81-82, 91, 96, 99, 102, 110, and 112-116 has a $K_i$ of less than 0.1 micromolar for PI3Kα. In one example, compound 37 has a $K_i$ of 0.002 micromolar.

All publications and patents cited in this specification are herein incorporated by reference as if each individual publication or patent were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:
1. A compound having the formula:

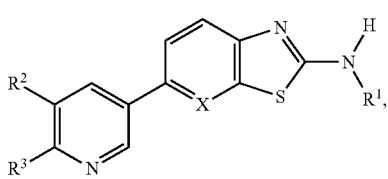

(I)

or a pharmaceutically acceptable salt thereof, wherein:
X is N or CH;
$R^1$ is selected from an optionally substituted pyridine, pyrimidine, pyrazine, pyridazine, thiazole, pyrazole, or thiadiazole ring, wherein each of said rings is optionally substituted with 1, 2, or 3 independent occurrences of $R^{1a}$;
$R^{1a}$ is chloro, fluoro, $C_{1-6}$ aliphatic, $C_{3-6}$ cycloaliphatic, —C(O)$R^{1b}$, —C(O)N($R^{1b}$)$_2$, —C(O)O($R^{1b}$), —S(O)$R^{1b}$, —S(O)$_2$N($R^{1b}$)$_2$, —N($R^{1b}$)$_2$, —N($R^{1b}$)C(O)$R^{1b}$, —N($R^{1b}$)S(O)$_2$$R^{1b}$, —O$R^{1b}$—S$R^{1b}$, or a 5-6 membered heteroaryl or heterocyclyl having up to 3 atoms selected from nitrogen, oxygen, or sulfur, wherein each of said aliphatic or cycloaliphatic is optionally substituted with 1, 2, 3, or 4, occurrences of $J^R$;
each $J^R$ is independently fluoro, oxo, —C(O)$R^{1b}$, —C(O)N($R^{1b}$)$_2$, —C(O)O($R^{1b}$), —N($R^{1b}$)$_2$, —N($R^{1b}$)C(O)$R^{1b}$, —O$R^{1b}$, —S$R^{1b}$, phenyl, or a 5-6 membered heteroaryl or heterocyclyl having up to 4 atoms selected from nitrogen, oxygen, or sulfur, wherein said phenyl, heteroaryl, or heterocyclyl or $J^R$ is optionally substituted with 1 or 2 $R^{1c}$ groups;
each $R^{1b}$ is independently selected from hydrogen, $C_{1-4}$aliphatic, $C_{3-6}$cycloaliphatic, phenyl, benzyl, wherein each of said aliphatic, cycloaliphatic, phenyl, or benzyl of $J^{R1}$ is optionally substituted with up to three $R^{1c}$ groups;
each $R^{1c}$ is independently selected from chloro, fluoro, oxo, $C_{1-2}$alkyl, $C_{1-2}$alkyl substituted with 1-3 fluorine atoms, $C_{3-6}$cycloalkyl, —OH, —O$C_{1-2}$alkyl, or —O$C_{1-2}$alkyl substituted with 1-3 fluorine atoms;
$R^2$ is hydrogen, fluoro, chloro, $C_{1-6}$aliphatic, —O$C_{1-6}$aliphatic, $C_{3-6}$cycloaliphatic, —O$C_{3-6}$cycloaliphatic, cyano, —NH$_2$, —NH$C_{1-6}$aliphatic, —NH$C_{3-6}$cycloaliphatic, —NHS(O)$_2$$C_{1-6}$aliphatic, —NHS(O)$_2$$C_{3-6}$cycloaliphatic, —NHS(O)$_2$phenyl, —NHS(O)$_2$benzyl, —NHS(O)$_2$heteroaryl, —S(O)$_2$$C_{1-6}$aliphatic, —S(O)$_2$$C_{3-6}$cycloaliphatic, —S(O)$_2$phenyl, —S(O)$_2$benzyl, —S(O)$_2$heteroaryl, —S(O)$_2$NH$C_{1-6}$aliphatic, —S(O)$_2$NH$C_{3-6}$cycloaliphatic, —S(O)$_2$NHphenyl, —S(O)$_2$NHbenzyl, or —S(O)$_2$NHheteroaryl, wherein said heteroaryl of $R^2$ is a 5- or 6-membered ring having 1, 2, or 3 atoms selected from N, O, or S, and wherein said aliphatic, cycloaliphatic, phenyl, benzyl, or heteroaryl of $R^2$ is optionally substituted with 1, 2, or 3 $R^{2a}$ groups;

each $R^{2a}$ is selected from chloro, fluoro, oxo, $C_{1-2}$alkyl, $C_{1-2}$alkyl substituted with 1-3 fluorine atoms, $C_{3-6}$cycloalkyl, —OH, —O$C_{1-2}$alkyl, or —O$C_{1-2}$alkyl substituted with 1-3 fluorine atoms; and $R^3$ is hydrogen, fluoro, chloro, $C_{1-3}$aliphatic, cyclopropyl, —O$C_{1-3}$aliphatic, NH$_2$, or NH$C_{1-3}$aliphatic, wherein said aliphatic of $R^3$ is optionally substituted with up to 3 occurrences of fluoro.

2. The compound according to claim 1, or a pharmaceutically acceptable salt thereof, wherein X is N.

3. The compound according to claim 1, or a pharmaceutically acceptable salt thereof, wherein $R^1$ is selected from

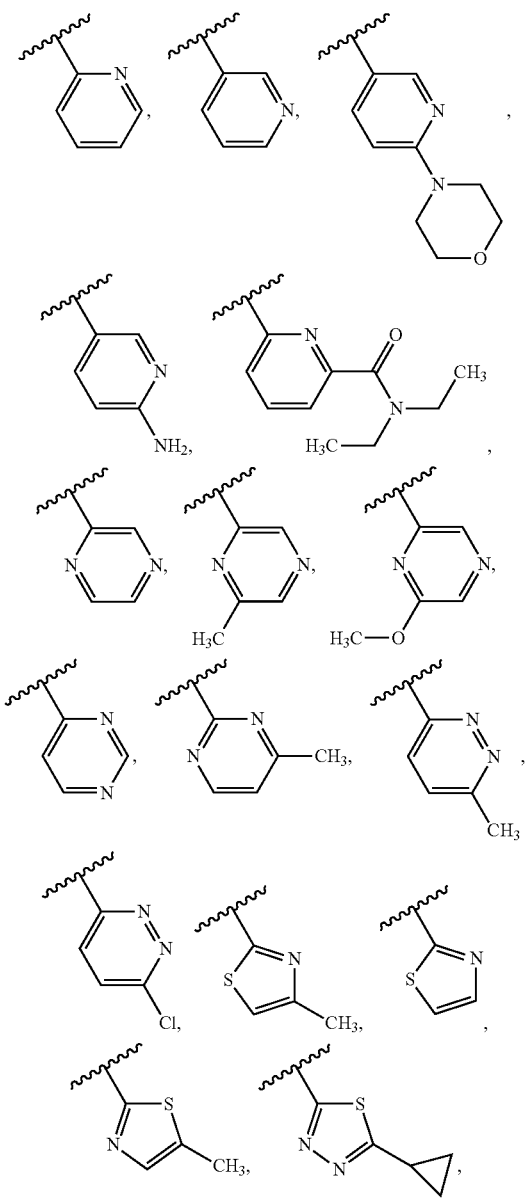

-continued

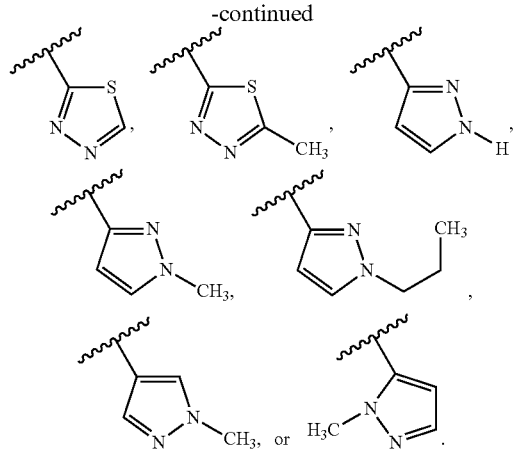

4. The compound according to claim 1, or a pharmaceutically acceptable salt thereof, wherein each of $R^2$ and $R^3$ is a $C_{1-3}$aliphatic or —$OC_{1-3}$alkyl optionally substituted with up to three $R^{2a}$ groups.

5. The compound according to claim 1, wherein $R^2$ is —$OC_{1-3}$alkyl.

6. The compound according to claim 1, wherein $R^2$ is —$CF_3$.

7. The compound according to claim 1, or a pharmaceutically acceptable salt thereof, wherein

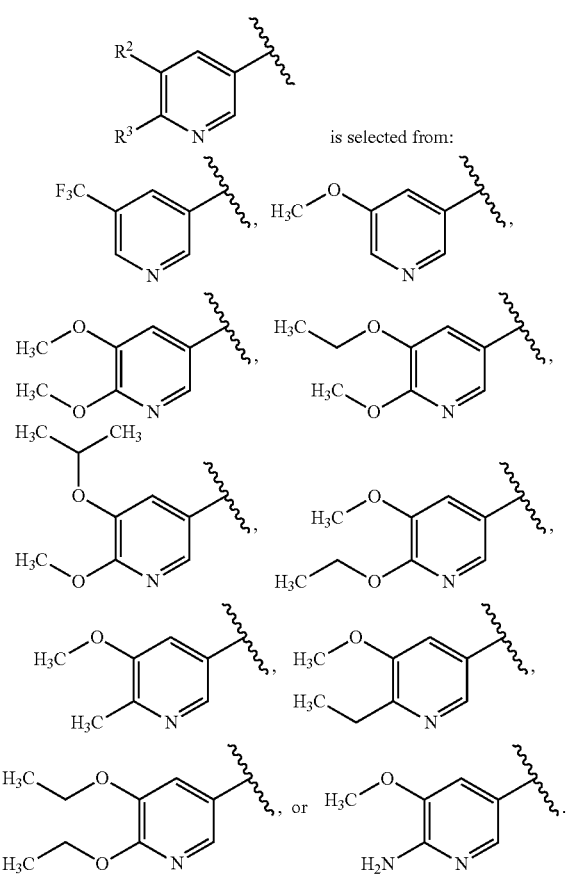

8. The compound according to claim 1, or a pharmaceutically acceptable salt thereof, wherein said compound is selected from:

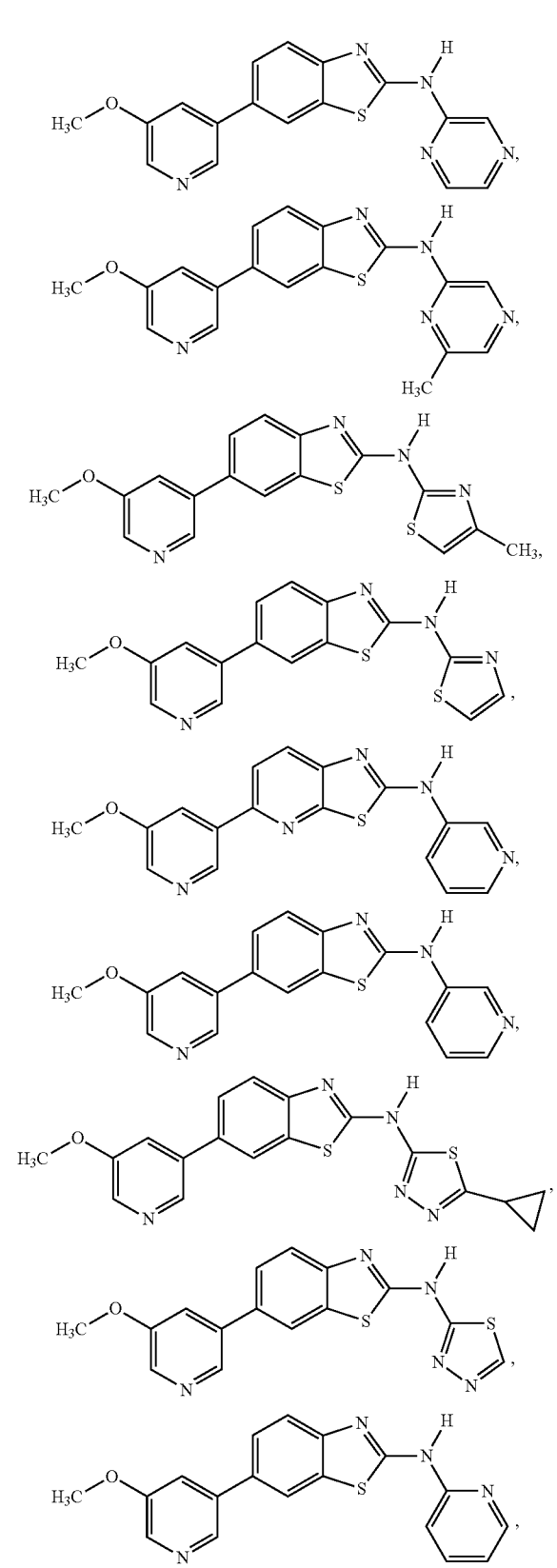

-continued
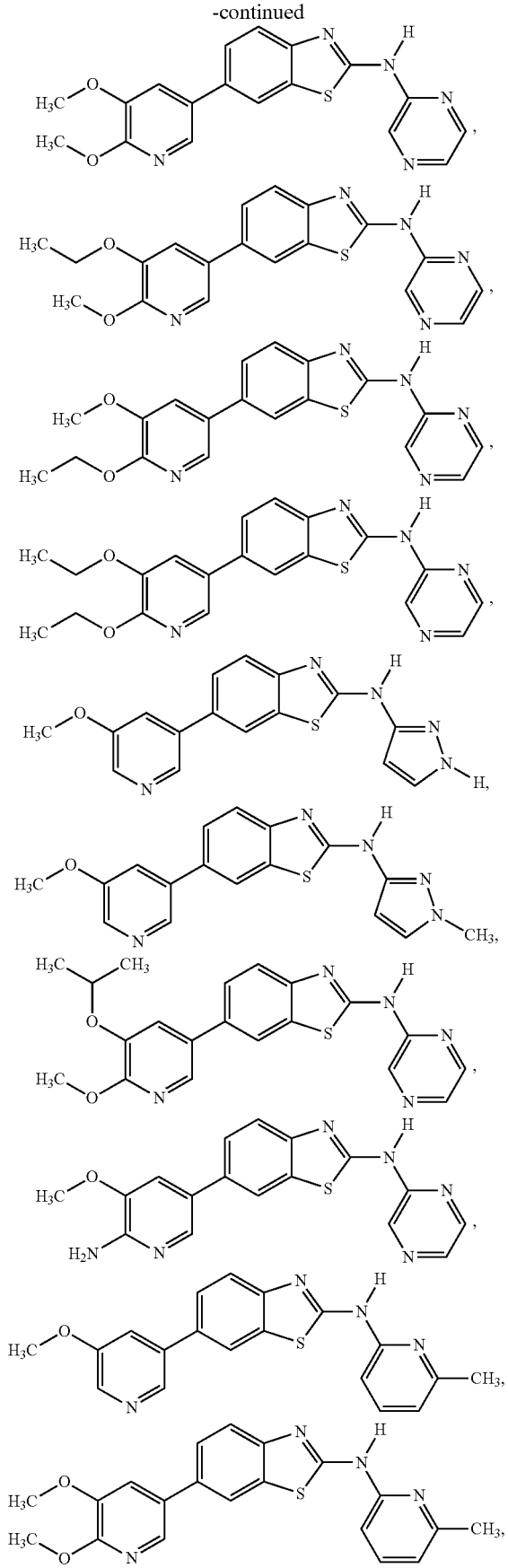
-continued
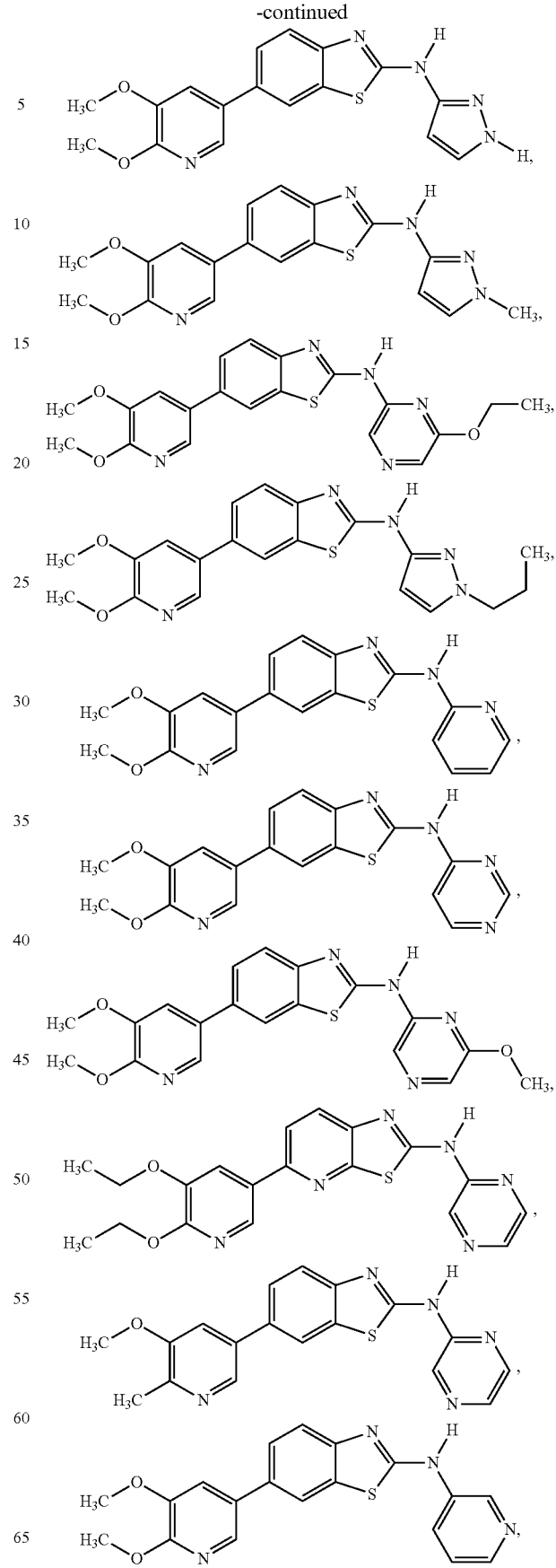

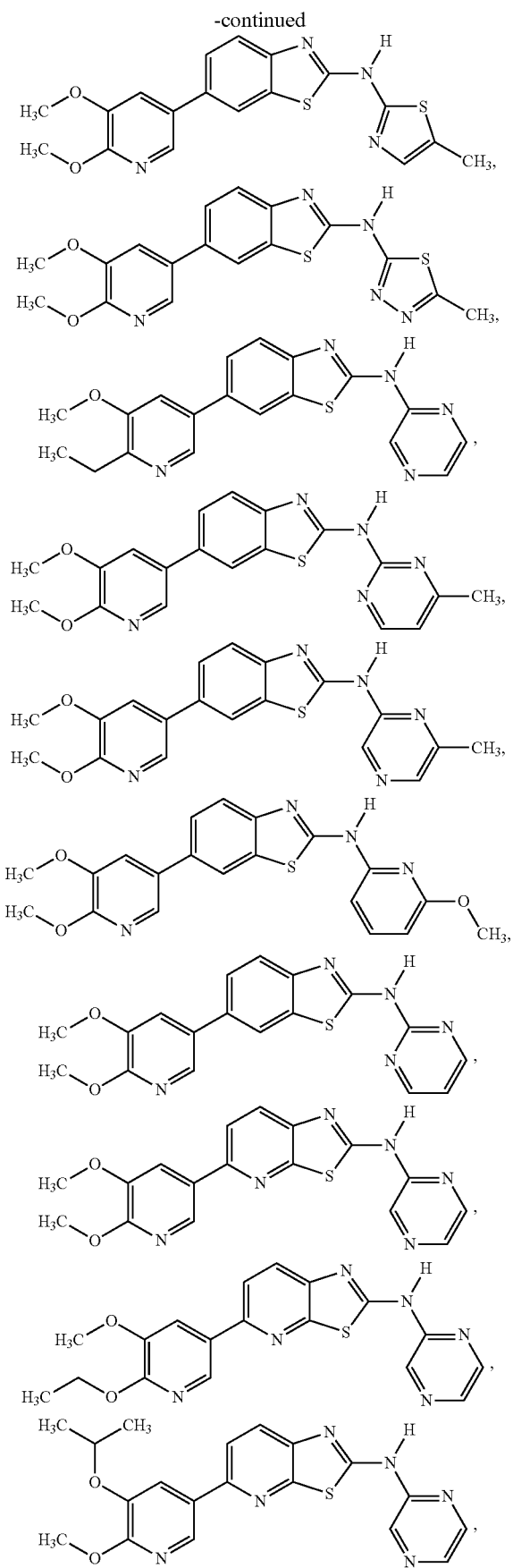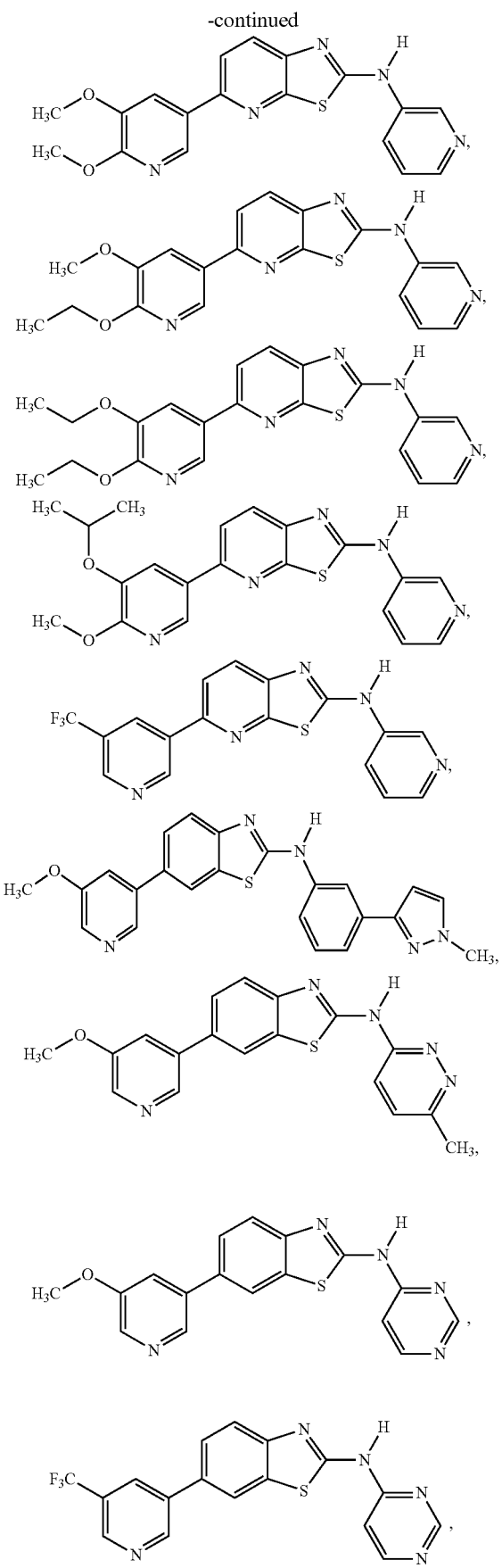

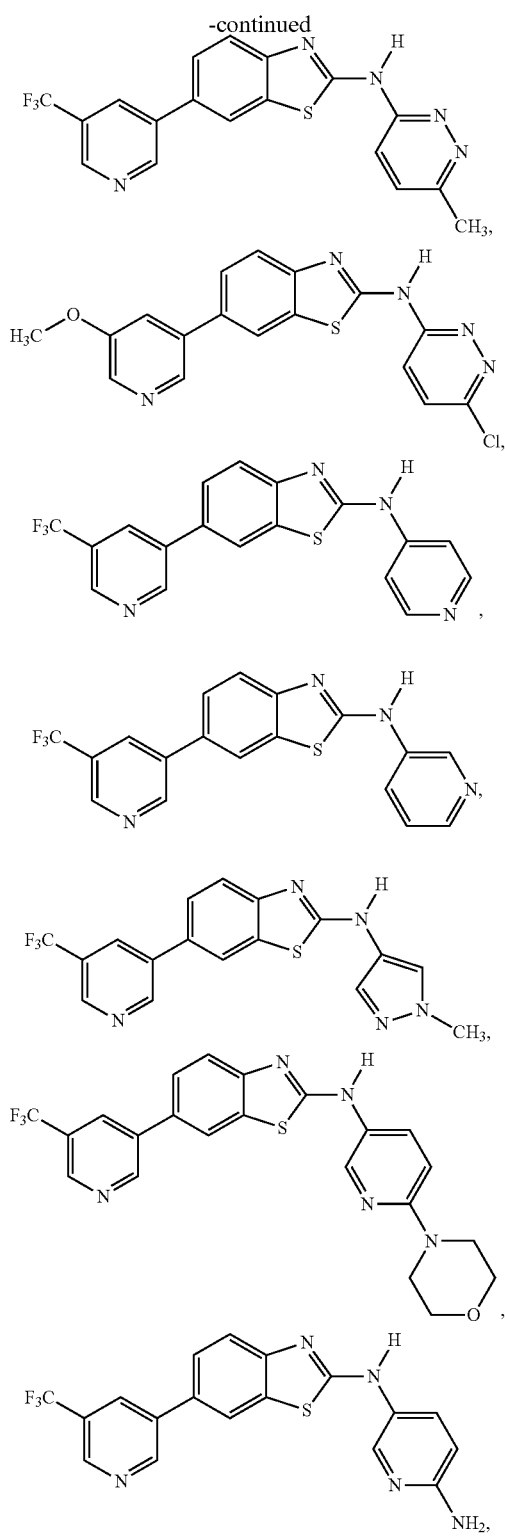
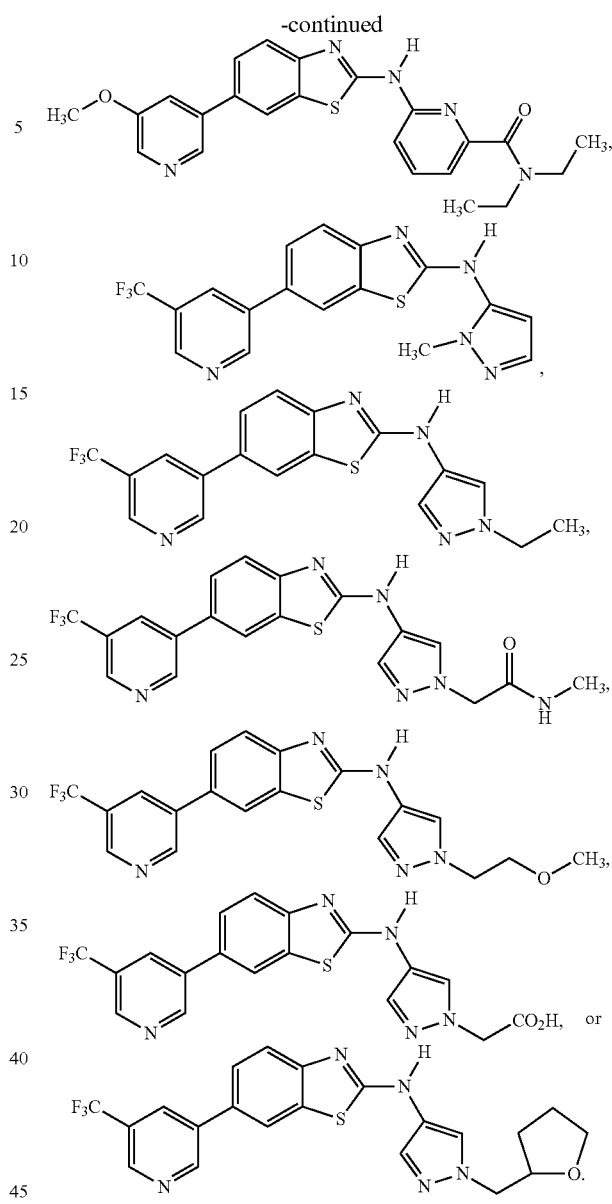

9. A pharmaceutical composition comprising a compound according to claim 1 and a pharmaceutically acceptable carrier, adjuvant, or vehicle.

10. The composition according to claim 9, additionally comprising a therapeutic agent selected from an agent for treating multiple sclerosis, an anti-inflammatory agent, an immunomodulatory agent, or an immunosuppressive agent.

11. A method of inhibiting PI3K-gamma kinase activity in a biological sample comprising contacting said biological sample with a compound according to claim 1 or a composition according to claim 9.

* * * * *